US012618050B2

(12) United States Patent
Li et al.

(10) Patent No.: US 12,618,050 B2
(45) Date of Patent: May 5, 2026

(54) ENGINEERED POLYPEPTIDES THAT EXHIBIT INCREASED CATALYTIC EFFICIENCY FOR UNNATURAL COFACTORS AND USES THEREOF

(71) Applicant: The Regents of the University of California, Oakland, CA (US)

(72) Inventors: Han Li, Irvine, CA (US); Justin B. Siegel, Davis, CA (US); Youtian Cui, Davis, CA (US); Wai Shun Mak, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 848 days.

(21) Appl. No.: 17/297,976

(22) PCT Filed: Dec. 10, 2019

(86) PCT No.: PCT/US2019/065553
§ 371 (c)(1),
(2) Date: May 27, 2021

(87) PCT Pub. No.: WO2020/123563
PCT Pub. Date: Jun. 18, 2020

(65) Prior Publication Data
US 2022/0090027 A1 Mar. 24, 2022

Related U.S. Application Data

(60) Provisional application No. 62/852,936, filed on May 24, 2019, provisional application No. 62/777,725, filed on Dec. 10, 2018.

(51) Int. Cl.
*C12N 9/04* (2006.01)
*C12N 9/02* (2006.01)

(52) U.S. Cl.
CPC ........... *C12N 9/0006* (2013.01); *C12N 9/001* (2013.01)

(58) Field of Classification Search
CPC .............................. C12N 9/0006; C12N 9/001
See application file for complete search history.

(56) References Cited

U.S. PATENT DOCUMENTS

2005/0026250 A1 2/2005 Zhao et al.
2005/0095619 A1 5/2005 Davis et al.
(Continued)

FOREIGN PATENT DOCUMENTS

WO 2003066816 A2 8/2003
WO 2017004709 A1 1/2017
WO WO-2018115422 A1 * 6/2018 ............. C12N 15/52

OTHER PUBLICATIONS

Nowak et al (ACS Catalysis 2017 7 (8), 5202-5208) (Year: 2017).*
(Continued)

*Primary Examiner* — David W Berke-Schlessel
(74) *Attorney, Agent, or Firm* — Gavrilovich, Dodd & Lindsey LLP

(57) ABSTRACT

Provided are engineered polypeptides having dehydrogenase activity that exhibit increased catalytic efficiency for nicotinamide-based unnatural cofactors relative to wild-type or parent polypeptides that encode a dehydrogenase that utilizes nicotinamide adenine dinucleotide or nicotinamide adenine dinucleotide phosphate. Also provided are cell-free and whole cell biotransformation systems for converting a substrate into a product using a redox reaction with a re-cycled unnatural cofactor that utilizes an engineered polypeptide that has dehydrogenase activity and which exhibits increased catalytic efficiency for nicotinamide-based unnatural cofactor.

7 Claims, 17 Drawing Sheets

Specification includes a Sequence Listing.

NAD⁺

NMN⁺

░ NMN⁺ Moiety

░ AMP Moiety

(56) References Cited

U.S. PATENT DOCUMENTS

| | | |
|---|---|---|
| 2011/0250663 A1 | 10/2011 | Schirmer et al. |
| 2013/0203130 A1 | 8/2013 | Wittmann et al. |
| 2016/0028101 A1 | 1/2016 | Zhang et al. |
| 2016/0153012 A1 | 6/2016 | Marliere |
| 2018/0042241 A1 | 2/2018 | Asolkar et al. |

OTHER PUBLICATIONS

Wang et al., "Synthetic Cofactor-Linked Metabolic Circuits for Selective Energy Transfer." ACS Catalysis 7:1977-1983 (2017).

Wildeman et al., "Biocatalytic Reductions: From Lab Curiosity to "First Choice"." Accounts of Chemical Research 40:1260-1266 (2007).

Yadav et al., "The future of metabolic engineering and synthetic biology: towards a systematic practice." Metabolic engineering 14:233-241 (2012).

Yamamoto et al., "Crystal structure of glucose dehydrogenase from Bacillus megaterium IWG3 at 1.7 A resolution." Journal of biochemistry 129:303-312 (2001).

Yoshisumi et al., "Cloning, sequence analysis, and expression in Escherichia coli of the gene encoding monovalent cation-activated levodione reductase from Corynebacterium aquaticum M-13." Bioscience, biotechnology, and biochemistry 65:830-836 (2001).

Zhang et al., "Development of a High-Throughput, In Vivo Selection Platform for NADPH-Dependent Reactions Based on Redox Balance Principles." ACS synthetic biology (2018).

Akhtar et al., "Carboxylic acid reductase is a versatile enzyme for the conversion of fatty acids into fuels and chemical commodities." Proceedings of the National Academy of Sciences of the United States of America 110:87-92 (2013).

Bennet et al., "Absolute metabolite concentrations and implied enzyme active site occupancy in Escherichia coli." Nature chemical biology 5:593-599 (2009).

Campbell et al., "Enzymatic biofuel cells utilizing a biomimetic cofactor." Chemical communications 48:1898-1900 (2012).

Chaparro-Riggers et al., "Comparison of Three Enoate Reductases and their Potential Use for Biotransformations." Advanced Synthesis & Catalysis 349:1521-1531 (2007).

Farrauto, R.J. "Industrial Catalysis: A Practical Guide." In: Kent J.A. (eds) Kent and Riegel's Handbook of Industrial Chemistry and Biotechnology. Springer, Boston, MA. (2007).

Fasan et al., "Tuning P450 Enzymes as Oxidation Catalysts." ACS Catalysis 2:647-666 (2012).

Finn et al. "HMMER web server: 2015 update." Nucleic Acids Res 43:W30-38 (2015).

Flores et al., "A modified consensus approach to mutagenesis inverts the cofactor specificity of Bacillus stearothermophilus lactate dehydrogenase." Protein Engineering, Design and Selection 18:369-377 (2005).

Gazzaniga et al., "Microbial NAD metabolism: lessons from comparative genomics." Microbiology and molecular biology reviews : MMBR 73:529-541 (2009).

Gordon et al., "Computational design of an alpha-gliadin peptidase." Journal of the American Chemical Society 134:20513-20520 (2012).

Grozio et al., "Slc12a8 is a nicotinamide mononucleotide transporter." Nature Metabolism 1:47-57 (2019).

Hiall et al., "Asymmetric whole-cell bioreduction of an $\alpha,\beta$-unsaturated aldehyde (citral): competing prim-alcohol dehydrogenase and C—C lyase activities." Tetrahedron: Asymmetry 17:3058-3062 (2006).

Hilt et al., "Glucose dehydrogenase from Bacillus subtilis expressed in Escherichia coli. I: Purification, characterization and comparison with glucose dehydrogenase from Bacillus megaterium." Biochimica et biophysica acta 1076:298-304 (1991).

Kataoka et al., "Old Yellow Enzyme from Candida macedoniensis catalyzes the stereospecific reduction of the C=C pond of ketoisophorone." Bioscience, biotechnology, and biochemistry 66:2651-2657 (2002).

Keasling et al., "Manufacturing Molecules Through Metabolic Engineering." Science 330:1355-1358 (2010).

Klefner et al., "Foldit Standalone: a video game-derived protein structure manipulation interface using Rosetta." Bioinformatics 33:2765-2767 (2017).

Knaus et al., "Better than Nature: Nicotinamide Biomimetics That Outperform Natural Coenzymes." Journal of the American Chemical Society 138:1033-1039 (2016).

Knox et al., "Virtual cofactors for an Escherichia coli nitroreductase enzyme: relevance to reductively activated brodrugs in antibody directed enzyme prodrug therapy (ADEPT)." Biochemical pharmacology 49:1641-1647 (1995).

Kulig et al., "Biochemical characterization of an alcohol dehydrogenase from Ralstonia sp." Biotechnology and bioengineering 110:1838-1848 (2013).

Kunjapur et al., "Microbial engineering for aldehyde synthesis." Applied and environmental microbiology 81:1892-1901 (2015).

Au et al., "Prokaryotic nanocompartments form synthetic organelles in a eukaryote." Nature communications 9:1311 (2018).

Lee et al., "Systems strategies for developing industrial microbial strains." Nat Biotechnol 33:1061-1072 (2015).

Liang et al., "Selection of an endogenous 2,3-butanediol pathway in Escherichia coli by fermentative redox balance." Metabolic engineering 39:181-191 (2017).

Lo et al., "Biomimetic NAD(+) models for tandem cofactor regeneration, horse liver alcohol dehydrogenase recognition of 1,4-NADH derivatives, and chiral synthesis." Angewandte Chemie 41:478-481 (2002).

Lobo et al., "Amperometric biosensors based on NAD(P)-dependent dehydrogenase enzymes." Electroanalysis 9:191-202 (2005).

Machado et al., "A selection platform for carbon chain elongation using the CoA-dependent pathway to produce inear higher alcohols." Metabolic engineering 14:504-511 (2012).

Mak et al., "Integrative genomic mining for enzyme function to enable engineering of a non-natural biosynthetic pathway." Nature communications 6:10005 (2015).

Mampel et al., "Coping with complexity in metabolic engineering." Trends in biotechnology 31:52-60 (2013).

Mansoorabadi et al., "The diverse roles of flavin coenzymes-nature's most versatile thespians." The Journal of organic chemistry 72:6329-6342 (2007).

Marinescu et al., "beta-nicotinamide mononucleotide (NMN) production in Escherichia coli." Scientific reports 8:12278 (2018).

Martinez et al., "Oxidoreductases on their way to industrial biotransformations." Biotechnology advances 35:815-831 (2017).

Muller et al., "Stereospecific Alkyne Reduction: Novel Activity of Old Yellow Enzymes." Angewandte Chemie International Edition 46:3316-3318 (2007).

Nowak et al., "Enzymatic Reduction of Nicotinamide Biomimetic Cofactors Using an Engineered Glucose Dehydrogenase: Providing a Regeneration System for Artificial Cofactors." ACS Catalysis 7:5202-5208 (2017).

Okamoto et al., "Efficient In Situ Regeneration of NADH Mimics by an Artificial Metalloenzyme." ACS Catalysis 6: 3553-3557 (2016).

Paddon et al., "Semi-synthetic artemisinin: a model for the use of synthetic biology in pharmaceutical development." Nature Reviews Microbiology 12:355 (2014).

Pandit et al., "Redesigning metabolism based on orthogonality principles." Nature communications 8:15188 (2017).

Paul et al., "Mimicking nature: synthetic nicotinamide cofactors for C horizontal lineC bioreduction using enoate reductases." Organic letters 15:180-183 (2013).

Paul et al., "Nonenzymatic Regeneration of Styrene Monooxygenase for Catalysis." ACS Catalysis 5:2961-2965 (2015).

Pohlmann et al., "Genome sequence of the bioplastic-producing "Knallgas" bacterium Ralstonia eutropha H16." Nat Biotechnol 24:1257-1262 (2006).

Race et al., "Structural and mechanistic studies of Escherichia coli nitroreductase with the antibiotic nitrofurazone. Reversed binding orientations in different redox states of the enzyme." The Journal of biological chemistry 280:13256-13264 (2005).

Richter et al., "De Novo Enzyme Design Using Rosetta3." PloS one 6:e19230 (2011).

(56) References Cited

OTHER PUBLICATIONS

Rocchitta et al., "Enzyme Biosensors for Biomedical Applications: Strategies for Safeguarding Analytical Performances in Biological Fluids." Sensors (Basel, Switzerland) 16:780 (2016).

Rodriguez et al., "Toward aldehyde and alkane production by removing aldehyde reductase activity in *Escherichia coli*." Metabolic engineering 25:227-237 (2014).

Rollin et al. "New biotechnology paradigm: cell-free biosystems for biomanufacturing." Green Chemistry 15:1708-1719 (2013).

Ryan et al., "Engineering cytochrome P450 enzymes for improved activity towards biomimetic 1,4-NADH cofactors." Chembiochem : a European journal of chemical biology 9:2579-2582 (2008).

Schewe et al., "Improvement of P450(BM-3) whole-cell biocatalysis by integrating heterologous cofactor regeneration combining glucose facilitator and dehydrogenase in *E. coli*." Applied microbiology and biotechnology 78:55-65 (2008).

Shiue et al., "Improving product yields on D-glucose in *Escherichia coli* via knockout of pgi and zwf and feeding of supplemental carbon sources." Biotechnology and bioengineering 112:579-587 (2015).

Siegel et al., "Computational protein design enables a novel one-carbon assimilation pathway." Proceedings of the National Academy of Sciences of the United States of America 112:3704-3709 (2015).

Song et al., "High-resolution comparative modeling with RosettaCM.". Structure 21:1735-1742 (2013).

Sorci et al., "Nicotinamide mononucleotide synthetase is the key enzyme for an alternative route of NAD biosynthesis in Francisella tularensis." Proceedings of the National Academy of Sciences of the United States of America 106:3083-3088 (2009).

Copenheaver, Blaine R. International Search Report and Written Opinion for PCT/US2019/065553. Mar. 10, 2020.

Fuentealba et al., "Determinants of Cofactor Specificity for the Glucose-6-Phosphate Dehydrogenase from *Escherichia coli*; Simulation, Kinetics and Evolutionary Studies," PLoS One 11(3):e0152403, pp. 1-22 (Mar. 24, 2016).

* cited by examiner

| Substrate a | Product b | Enzyme | Conversion (%) |
|---|---|---|---|
| 1 | | XenA | >99 |
| 2 | | XenA | 76 ± 2 |
| 3 | | XenA | 49 ± 3 |
| 4 | | OYE3 | >99 |
| 5 | | NfsB | 92 ± 1 |
| 6 cytochrome *c* (oxidized) | cytochrome *c* (reduced) | P450 BM3* | >99 |

ENGINEERED POLYPEPTIDES THAT EXHIBIT INCREASED CATALYTIC EFFICIENCY FOR UNNATURAL COFACTORS AND USES THEREOF

CROSS REFERENCE TO RELATED APPLICATIONS

This application claims priority to U.S. Provisional Application Ser. No. 62/777,725, filed Dec. 10, 2018 and to U.S. Provisional Application Ser. No. 62/852,936, filed May 24, 2019, the disclosures of which are incorporated herein by reference in their entirety.

STATEMENT OF GOVERNMENT SUPPORT

This application is a U.S. National Stage Application filed under 35 U.S.C. § 371 and claims priority to International Application No. PCT/US2019/065553, filed Dec. 10, 2019, which application claims priority to U.S. Provisional Application Ser. No. 62/777,725, filed Dec. 10, 2018 and to U.S. Provisional Application Ser. No. 62/852,936, filed May 24, 2019, the disclosures of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Dec. 10, 2019, is named Sequence_ST25.txt and is 74,131 bytes in size.

TECHNICAL FIELD

Provided herein are engineered polypeptides that exhibit increased catalytic efficiency for unnatural cofactors and uses of said polypeptides in engineered unnatural redox cofactor systems for whole-cell biomanufacturing and in cell-free applications.

BACKGROUND

Oxidoreductases are some of the best-established enzymatic tools for chemical synthesis due to their versatile functionality, broad substrate ranges, and high regio- and enantio-selectivity. Large-scale industrial processes using oxidoreductases to install the desired chiral centers have been developed, which feature lower cost, high product yield, mild reaction conditions, and environmental friendliness compared to their chemical catalyst-mediated counterparts. Oxidoreductases utilize cofactors which must be regenerated with each product molecule. An efficient redox cofactor recycling system is an indispensable component of an economically viable oxidoreductase process, owing to the formidable cost of using electron donors NAD(P)H at stoichiometric amounts. To this end, various methods have been employed to regenerate the reduced cofactors. Among them, formate dehydrogenases (FDHs) and glucose dehydrogenases (GDHs) are most widely used because they consume inexpensive substrates to reduce NAD(P)$^+$ in a virtually irreversible way.

SUMMARY

Enzymatic biotransformation is a convenient way to manufacture chiral chemicals. Typically, an enzymatic biotransformation requires an enzyme, such as oxidoreductase, and a redox cofactor system to mediate the regeneration of the enzyme. These cofactors are expensive to use in vitro and difficult to control in vivo. Although simple and efficient redox cofactor analogs, also known as biomimetics, have been synthesized, native enzymes seem to display low activities towards these simple unnatural cofactor analogs. A potentially elegant solution is to utilize unnatural cofactors which operate in an orthogonal manner to naturally occurring cofactors.

Provided herein is the development of an unnatural redox cofactor system that utilizes a nicotinamide-based unnatural cofactor (e.g., NMN$^+$). The key enzyme in the system is a computationally designed glucose dehydrogenase (GDH) with a 107-fold cofactor specificity switch towards the nicotinamide-based unnatural cofactor over NAD(P)$^+$. It is demonstrated herein that this system can be used to support diverse redox chemistries in vitro with high total turnover number (~39,000); to specifically channel reducing power in *Escherichia coli* whole cells from glucose to a pharmaceutical intermediate; levodione, and to sustain the high metabolic flux required for the central carbon metabolism to support growth.

Accordingly, the disclosure provides for computationally designed engineered polypeptides and proteins that efficiently regenerate unnatural cofactors to support diverse redox chemistries, including for applications, like the synthesis of compounds, chiral compounds in particular, and in vitro biotransformations. Additionally, the disclosure provides for unnatural redox cofactor systems, comprising said engineered polypeptides for efficient whole-cell biomanufacturing and other applications.

In a particular embodiment, the disclosure provides for an engineered polypeptide that exhibits increased catalytic efficiency for an unnatural cofactor than a wild-type or parent polypeptide sequence, wherein the engineered polypeptide comprises one or more introduced amino acid substitutions in comparison to the wild-type or parent polypeptide sequence, and wherein the one or more amino acid substitutions increases electrostatic complementarity between the engineered polypeptide and the unnatural cofactor. In a further embodiment of the foregoing embodiment, the engineered polypeptide encodes an oxidoreductase. In yet a further embodiment of any of the foregoing embodiments, the engineered polypeptide encodes a dehydrogenase. In yet a further embodiment of any of the foregoing embodiments, the unnatural cofactor is a nicotinamide-based unnatural cofactor. In yet a further embodiment of any of the foregoing embodiments, the nicotinamide-based unnatural cofactor is selected from nicotinamide mononucleotide (NMN$^+$), 1-phenyl-1,4,-dihydronicotinamide (PNA$^+$), 1-benzyl-1,4-dihydronicotinamide (BNA$^+$), 1-(4-hydroxyphenyl)1,4-dihydronicotinamide (HPNA$^+$), 1-methyl-1,4-dihydronicotinamide (MNA$^+$), nicotinamide flucytosine dinucleotide (NFCD$^+$), nicotinamide mononucleoside (NR$^+$), 1-butyl-1, 4,5,6-tetrahydropyridine-3-carboxamide, 1-(1-benzyl-1,4,5, 6-tetrahydropyridin-3-yl) ethenone, 1-benzyl-1,4-dihydropyridine-3-carboxylic acid, and 1-benzyl-1,4,5,6-tetrahydropyridine-3-carbonitrile. In yet a further embodiment of any of the foregoing embodiments, the nicotinamide-based unnatural cofactor is nicotinamide mononucleotide (NMN$^+$). In yet a further embodiment of any of the foregoing embodiments, the engineered polypeptide reduces the unnatural cofactor by extracting electrons from an inexpensive feedstock. In yet a further embodiment of any of the foregoing embodiments, the inexpensive feedstock is glucose. In yet a further embodiment of any of the foregoing embodiments, the engineered polypeptide has at least 100-fold more catalytic activity for the unnatural cofactor than the wild-type or parent polypeptide. In yet a further embodiment of any of the foregoing embodiments, the engineered polypeptide has 1000-fold or more catalytic activity for the unnatural cofactor than the wild-type or parent polypeptide. In yet a further embodiment of any of the foregoing embodiments, the engineered polypeptide comprises a sequence that has at least 80% sequence identity to SEQ ID NO:1 or to a sequence of WP_003246720.1, EHA28975.1, WP_119899028.1, CDH98271.1, WP_038427366.1, WP_095431766.1, WP_041340171.1, WP_032726518.1, AXV60254.1, WP_044161863.1, WP_014478842.1, WP_003225027.1, OTQ88242.1, WP_059291954.1, WP_010333037.1, KIU10883.1, WP_105991496.1, WP_095010766.1, ANW06331.1, PTU26434.1, WP_103749790.1, WP_077671287.1, WP_019713327.1, WP_014475815.1, AAA22463.1, WP_071581042.1, AGE62243.1, WP_103031562.1, WP_003240219.1, WP_071578344.1, WP_024714517.1, KJJ40202.1, WP_010330813.1, WP_064814593.1, WP_100741417.1, WP_087993024.1, WP_039075845.1, WP_070081367.1, WP_061522816.1, WP_098080985.1, WP_082998974.1, WP_088461430.1, WP_025284235.1, WP_061573960.1, WP_104678928.1, WP_061669578.1, WP_099744414.1, WP_065521908.1, WP_065980712.1, WP_106360802.1, WP_061184372.1, WP_073536545.1, WP_053403598.1, WP_000287801.1, WP_088119901.1, WP_000287802.1, WP_054768130.1, WP_061654990.1, WP_097824161.1, WP_098487332.1, WP_053485906.1, WP_000287797.1, WP_098607945.1, WP_043068355.1, WP_078417142.1, WP_048520053.1, WP_098671912.1, WP_098487331.1, WP_045294049.1, SUV21072.1, or WP_097856719.1. In yet a further embodiment of any of the foregoing embodiments, the engineered polypeptide comprises a sequence that has at least 90% sequence identity to SEQ ID NO:1 or to a sequence of WP_003246720.1, EHA28975.1, WP_119899028.1, CDH98271.1, WP_038427366.1, WP_095431766.1, WP_041340171.1, WP_032726518.1, AXV60254.1, WP_044161863.1, WP_014478842.1, WP_003225027.1, OTQ88242.1, WP_059291954.1, WP_010333037.1, KIU10883.1, WP_105991496.1, WP_095010766.1, ANW06331.1, PTU26434.1, WP_103749790.1, WP_077671287.1, WP_019713327.1, WP_014475815.1, AAA22463.1, WP_071581042.1, AGE62243.1, WP_103031562.1, WP_003240219.1, WP_071578344.1, WP_024714517.1, KJJ40202.1, WP_010330813.1, WP_064814593.1, WP_100741417.1, WP_087993024.1, WP_039075845.1, WP_070081367.1, WP_061522816.1, WP_098080985.1, WP_082998974.1, WP_088461430.1, WP_025284235.1, WP_061573960.1, WP_104678928.1, WP_061669578.1, WP_099744414.1, WP_065521908.1, WP_065980712.1, WP_106360802.1, WP_061184372.1, WP_073536545.1, WP_053403598.1, WP_000287801.1, WP_088119901.1, WP_000287802.1, WP_054768130.1, WP_061654990.1, WP_097824161.1, WP_098487332.1, WP_053485906.1, WP_000287797.1, WP_098607945.1, WP_043068355.1, WP_078417142.1, WP_048520053.1, WP_098671912.1, WP_098487331.1, WP_045294049.1, SUV21072.1, or WP_097856719.1. In yet a further embodiment of any of the foregoing embodiments, the engineered polypeptide comprises a sequence that has at least 98% sequence identity to SEQ ID NO:1 or to a sequence of WP_003246720.1, EHA28975.1, WP_119899028.1, CDH98271.1, WP_038427366.1, WP_095431766.1, WP_041340171.1, WP_032726518.1, AXV60254.1, WP_044161863.1, WP_014478842.1, WP_003225027.1, OTQ88242.1, WP_059291954.1, WP_010333037.1, KIU10883.1, WP_105991496.1, WP_095010766.1, ANW06331.1, PTU26434.1, WP_103749790.1, WP_077671287.1, WP_019713327.1, WP_014475815.1, AAA22463.1, WP_071581042.1, AGE62243.1, WP_103031562.1, WP_003240219.1, WP_071578344.1, WP_024714517.1, KJJ40202.1, WP_010330813.1, WP_064814593.1, WP_100741417.1, WP_087993024.1, WP_039075845.1, WP_070081367.1, WP_061522816.1, WP_098080985.1, WP_082998974.1, WP_088461430.1, WP_025284235.1, WP_061573960.1, WP_104678928.1, WP_061669578.1, WP_099744414.1, WP_065521908.1, WP_065980712.1, WP_106360802.1, WP_061184372.1, WP_073536545.1, WP_053403598.1, WP_000287801.1, WP_088119901.1, WP_000287802.1, WP_054768130.1, WP_061654990.1, WP_097824161.1, WP_098487332.1, WP_053485906.1, WP_000287797.1, WP_098607945.1, WP_043068355.1, WP_078417142.1, WP_048520053.1, WP_098671912.1, WP_098487331.1, WP_045294049.1, SUV21072.1, or WP_097856719.1. In yet a further embodiment of any of the foregoing embodiments, the engineered polypeptide comprises one of more of the following amino acid substitutions in comparison to SEQ ID NO:1: I195R, A93K, Y39Q, and/or S17E. In yet a further embodiment of any of the foregoing embodiments, the engineered polypeptide has the same sequence as SEQ ID NO:1 except for a I195R substitution (SEQ ID NO:2), except for a A93K substitution (SEQ ID NO:3), except for a Y39Q substitution (SEQ ID NO:4), except for a S17E substitution (SEQ ID NO:5), except for I195R, A93K, Y39Q substitutions (SEQ ID NO:6), or except for I195R, A93K, Y39Q, S17E substitutions (SEQ ID NO:7).

In a particular embodiment, the disclosure provides a cell-free biotransformation system for converting a substrate into a product using a redox reaction with a re-cycled unnatural cofactor, comprising: a feedstock; a substrate; an engineered polypeptide as disclosed herein; and one or more enzymes that can catalyze the transformation of the substrate into a product by using electrons from the unnatural cofactor, wherein the feedstock and substrate may be the same. In a further embodiment of the foregoing embodiment, the one or more enzymes are oxidoreductases. In yet a further embodiment of any of the foregoing embodiments, the one or more enzymes are selected from the groups consisting of alcohol dehydrogenase (NAD) (EC 1.1.1.1), alcohol dehydrogenase (NADP) (EC 1.1.1.2), homoserine dehydrogenase (EC 1.1.1.3), aminopropanol oxidoreductase (EC 1.1.1.4), diacetyl reductase (EC 1.1.1.5), glycerol dehydrogenase (EC 1.1.1.6), propanediol-phosphate dehydrogenase (EC 1.1.1.7), glycerol-3-phosphate dehydrogenase (NAD$^+$) (EC 1.1.1.8), D-xylulose reductase (EC 1.1.1.9), L-xylulose reductase (EC 1.1.1.10), lactate dehydrogenase (EC 1.1.1.27), malate dehydrogenase (EC 1.1.1.37), isocitrate dehydrogenase (EC 1.1.1.42), HMG-CoA reductase EC (1.1.1.88), glucose oxidase (EC 1.1.3.4), L-gulonolactone oxidase (EC 1.1.3.8), thiamine oxidase (EC 1.1.3.23), xanthine oxidase (EC 1.1.3.32), acetaldehyde dehydrogenase EC (1.2.1.10), glyceraldehyde 3-phosphate dehydrogenase (EC 1.2.1.12), pyruvate dehydrogenase (EC 1.2.1.51), oxoglutarate dehydrogenase (EC 1.2.4.2), biliverdin reductase (EC 1.3.1.24), protoporphyrinogen oxidase (EC 1.3.3.4), monoamine oxidase (EC 1.4.3.4), dihydrofolate reductase (EC 1.5.1.3), methylenetetrahydrofolate reductase (EC 1.5.1.20), sarcosine oxidase (EC 1.5.3.1), dihydrobenzophenanthridine oxidase (EC 1.5.3.12), urate oxidase (EC 1.7.3.3), nitrite reductase (EC 1.7.99.3), nitrate reductase (EC 1.7.99.4), glutathione reductase (EC 1.8.1.7), thiore-doxin reductase (EC 1.8.1.9), sulfite oxidase (EC 1.8.3.1), cytochrome c oxidase (EC 1.9.3.1), coenzyme Q-cy-tochrome c reductase (EC 1.10.2.2), catechol oxidase (EC 1.10.3.1), and laccase (EC 1.10.3.2), cytochrome c peroxi-dase (EC 1.11.1.5), catalase (EC 1.11.1.6), myeloperoxidase (EC 1.11.1.7), thyroid peroxidase (EC 1.11.1.8), glutathione peroxidase (EC 1.11.1.9), 4-hydroxyphenylpyruvate dioxy-genase (EC 1.13.11.27), *Renilla*-luciferin 2-monooxygenase (EC 1.13.12.5), cypridina-luciferin 2-monooxygenase (EC 1.13.12.6), Firefly luciferase (EC 1.13.12.7), watasenia-luciferin 2-monooxygenase (EC 1.13.12.8), oplophorus-lu-ciferin 2-monooxygenase EC (1.13.12.13), aromatase (EC 1.14.14.1), CYP2D6 (EC 1.14.14.1), CYP2E1 (EC 1.14.14.1), CYP3A4 (EC 1.14.14.1), cytochrome P450 oxi-dase, nitric oxide synthase (EC 1.14.13.39), phenylalanine hydroxylase (EC 1.14.16.1), tyrosinase (EC 1.14.18.1), superoxide dismutase (EC 1.15.1.1), nitrogenase (EC 1.18.6.1), and deiodinase (EC 1.97.1.10). In yet a further embodiment of any of the foregoing embodiments, the one or more enzymes are selected from an enoate reductase XenA from *Pseudomonas putida*, a glucose dehydrogenase from *Bacillus megaterium*, an enoate reductase OYE3 from *Saccharomyces cerevisiae*, and/or a nitro reductase NfsB from *Escherichia coli*. In yet a further embodiment of any of the foregoing embodiments, the unnatural cofactor is selected from nicotinamide mononucleotide (NMN$^+$), 1-phenyl-1,4,-dihydronicotinamide (PNA$^+$), 1-benzyl-1,4-dihydronicotinamide (BNA$^+$), 1-(4-hydroxyphenyl)1,4-di-hydronicotinamide (HPNA$^+$), 1-methyl-1,4-dihydronicoti-namide (MNA$^+$), nicotinamide flucytosine dinucleotide (NFCD$^+$), nicotinamide mononucleoside (NR$^+$), 1-butyl-1, 4,5,6-tetrahydropyridine-3-carboxamide, 1-(1-benzyl-1,4,5, 6-tetrahydropyridin-3-yl) ethenone, 1-benzyl-1,4-dihydro-pyridine-3-carboxylic acid, and 1-benzyl-1,4,5,6-tetrahydropyridine-3-carbonitrile. In yet a further embodiment of any of the foregoing embodiments, the feedstock is glucose.

In a certain embodiment, the disclosure also provides for a whole-cell biomanufacturing system for converting a substrate into a product using a redox reaction with a re-cycled unnatural cofactor, comprising: a feedstock; a substrate; a recombinant microorganism that has been engi-neered to express an engineered polypeptide disclosed herein; and wherein the recombinant microorganism expresses one or more enzymes that can catalyze the trans-formation of the substrate into a product by using electrons from the unnatural cofactor, wherein the feedstock and substrate may be the same. In a further embodiment of the foregoing embodiment, the recombinant microorganism is recombinant bacteria or recombinant yeast. In yet a further embodiment of any of the foregoing embodiments, the recombinant bacteria is recombinant *Escherichia coli*. In yet a further embodiment of any of the foregoing embodiments, the recombinant microorganism has been modified by intro-ducing mutation(s) that disrupts one or more metabolic or enzymatic pathways of the recombinant microorganism, introducing one or polypeptides that results in overexpres-sion of one or more metabolic or enzymatic pathways of the recombinant microorganism, introducing one or more muta-tions that results in shunting metabolites from one metabolic or enzymatic pathway to another pathway in the recombi-nant microorganism, introducing feedback mechanisms to either repress or activate enzymatic or metabolic pathways in the recombinant microorganism, or any combination of the foregoing. In yet a further embodiment of any of the foregoing embodiments, the recombinant microorganism comprises mutation(s) to disrupt genes of the Embden-Meyerhof-Parnas and/or the pentose phosphate pathway. In yet a further embodiment of any of the foregoing embodi-ments, the recombinant microorganism comprises mutation(s) which disrupts the expression of the zwf, gnd, and/or pgi genes. In yet a further embodiment of any of the foregoing embodiments, the recombinant microorganism comprises one or more polypeptides that overexpress genes associated with the Entner-Doudroff pathway. In yet a further embodiment of any of the foregoing embodiments, the recombinant microorganism comprises polypeptide(s) that enhance the expression of a glucose facilitator, a glu-conate kinase, and/or a glutamate dehydrogenase. In yet a further embodiment of any of the foregoing embodiments, the one or more enzymes are oxidoreductases. In yet a further embodiment of any of the foregoing embodiments, the one or more enzymes are selected from the groups consisting of alcohol dehydrogenase (NAD) (EC 1.1.1.1), alcohol dehydrogenase (NADP) (EC 1.1.1.2), homoserine dehydrogenase (EC 1.1.1.3), aminopropanol oxidoreductase (EC 1.1.1.4), diacetyl reductase (EC 1.1.1.5), glycerol dehy-drogenase (EC 1.1.1.6), propanediol-phosphate dehydroge-nase (EC 1.1.1.7), glycerol-3-phosphate dehydrogenase (NAD$^+$) (EC 1.1.1.8), D-xylulose reductase (EC 1.1.1.9), L-xylulose reductase (EC 1.1.1.10), lactate dehydrogenase (EC 1.1.1.27), malate dehydrogenase (EC 1.1.1.37), isoci-trate dehydrogenase (EC 1.1.1.42), HMG-CoA reductase EC (1.1.1.88), glucose oxidase (EC 1.1.3.4), L-gulonolactone oxidase (EC 1.1.3.8), thiamine oxidase (EC 1.1.3.23), xan-thine oxidase (EC 1.1.3.32), acetaldehyde dehydrogenase EC (1.2.1.10), glyceraldehyde 3-phosphate dehydrogenase (EC 1.2.1.12), pyruvate dehydrogenase (EC 1.2.1.51), oxo-glutarate dehydrogenase (EC 1.2.4.2), biliverdin reductase (EC 1.3.1.24), protoporphyrinogen oxidase (EC 1.3.3.4), monoamine oxidase (EC 1.4.3.4), dihydrofolate reductase (EC 1.5.1.3), methylenetetrahydrofolate reductase (EC 1.5.1.20), sarcosine oxidase (EC 1.5.3.1), dihydrobenzo-phenanthridine oxidase (EC 1.5.3.12), urate oxidase (EC 1.7.3.3), nitrite reductase (EC 1.7.99.3), nitrate reductase (EC 1.7.99.4), glutathione reductase (EC 1.8.1.7), thiore-doxin reductase (EC 1.8.1.9), sulfite oxidase (EC 1.8.3.1), cytochrome c oxidase (EC 1.9.3.1), coenzyme Q-cy-tochrome c reductase (EC 1.10.2.2), catechol oxidase (EC 1.10.3.1), and laccase (EC 1.10.3.2), cytochrome c peroxi-dase (EC 1.11.1.5), catalase (EC 1.11.1.6), myeloperoxidase (EC 1.11.1.7), thyroid peroxidase (EC 1.11.1.8), glutathione peroxidase (EC 1.11.1.9), 4-hydroxyphenylpyruvate dioxy-genase (EC 1.13.11.27), renilla-luciferin 2-monooxygenase (EC 1.13.12.5), cypridina-luciferin 2-monooxygenase (EC 1.13.12.6), Firefly luciferase (EC 1.13.12.7), watasenia-luciferin 2-monooxygenase (EC 1.13.12.8), oplophorus-lu-ciferin 2-monooxygenase EC (1.13.12.13), aromatase (EC 1.14.14.1), CYP2D6 (EC 1.14.14.1), CYP2E1 (EC 1.14.14.1), CYP3A4 (EC 1.14.14.1), cytochrome P450 oxi-dase, nitric oxide synthase (EC 1.14.13.39), phenylalanine hydroxylase (EC 1.14.16.1), tyrosinase (EC 1.14.18.1), superoxide dismutase (EC 1.15.1.1), nitrogenase (EC 1.18.6.1), and deiodinase (EC 1.97.1.10). In yet a further embodiment of any of the foregoing embodiments, the one or more enzymes are selected from an enoate reductase XenA from *Pseudomonas putida*, a glucose dehydrogenase from *Bacillus megaterium*, an enoate reductase OYE3 from *Saccharomyces cerevisiae*, and/or a nitro reductase NfsB from *Escherichia coli*. In yet a further embodiment of any of the foregoing embodiments, the unnatural cofactor is selected from nicotinamide mononucleotide (NMN$^+$), 1-phenyl-1,4,-dihydronicotinamide (PNA$^+$), 1-benzyl-1,4- dihydronicotinamide (BNA$^+$), 1-(4-hydroxyphenyl)1,4-dihydronicotinamide (HPNA$^+$), 1-methyl-1,4-dihydronicotinamide (MNA$^+$), nicotinamide flucytosine dinucleotide (NFCD$^+$), nicotinamide mononucleoside (NR$^+$), 1-butyl-1,4,5,6-tetrahydropyridine-3-carboxamide, 1-(1-benzyl-1,4,5,6-tetrahydropyridin-3-yl) ethenone, 1-benzyl-1,4-dihydropyridine-3-carboxylic acid, and 1-benzyl-1,4,5,6-tetrahydropyridine-3-carbonitrile. In yet a further embodiment of any of the foregoing embodiments, the unnatural cofactor is NMN$^+$. In yet a further embodiment of any of the foregoing embodiments, the feedstock is glucose.

In a particular embodiment, the disclosure also provides for an engineered polypeptide having dehydrogenase activity that exhibits increased catalytic efficiency for a nicotinamide-based unnatural cofactor relative to a wild-type or parent polypeptide that encodes a dehydrogenase, wherein the engineered polypeptide comprises 1, 2, 3, 4, 5, 6, 7, or 8 introduced amino acid substitutions in comparison to the sequence of the wild-type or parent polypeptide, wherein the introduced amino acid substitutions increase electrostatic complementarity between the engineered polypeptide and the unnatural cofactor, wherein the nicotinamide-based unnatural cofactor is a cofactor that is not normally utilized by the dehydrogenase encoded by the wild-type or parent polypeptide to catalyze a reaction, and wherein the cofactor normally utilized by the wild-type or parent polypeptide is nicotinamide adenine dinucleotide (NAD$^+$) or nicotinamide adenine dinucleotide phosphate (NADP$^+$). In yet a further embodiment of the foregoing embodiment, the engineered polypeptide comprises 3, 4, 5, or 6 introduced amino acid substitutions in comparison to the sequence of the wild-type or parent polypeptide. In yet a further embodiment of any of the foregoing embodiments, the engineered polypeptide comprises 3 or 4 introduced amino acid substitutions in comparison to the sequence of the wild-type or parent polypeptide. In yet a further embodiment of any of the foregoing embodiments, the introduced amino acid substitution(s) promote the formation of hydrogen bonds between the engineered polypeptide and the nicotinamide-based unnatural cofactor. In yet a further embodiment of any of the foregoing embodiments, the introduced amino acid substitutions promote the formation of hydrogen bonds between the engineered polypeptide and the nicotinamide-based unnatural cofactor in same binding site as the natural cofactor binds to the wild-type or parent polypeptide. In yet a further embodiment of any of the foregoing embodiments, the engineered polypeptide further comprises 1, 2, 3, 4, 5, 6, 7, or 8 additional amino acid substitutions in comparison to the wild-type or parent polypeptide, wherein the additional amino acid substitutions disrupt electrostatic complementarity between the engineered polypeptide and NAD$^+$ or NADP$^+$. In yet a further embodiment of any of the foregoing embodiments, the additional amino acid substitution(s) disrupt hydrogen bond formation between the engineered polypeptide and NAD$^+$ or NADP$^+$. In yet a further embodiment of any of the foregoing embodiments, the dehydrogenase is selected from the group consisting of alcohol dehydrogenase (NAD), alcohol dehydrogenase (NADP), homoserine dehydrogenase, glucose dehydrogenase, glycerol dehydrogenase, propanediol-phosphate dehydrogenase, glycerol-3-phosphate dehydrogenase (NAD$^+$), lactate dehydrogenase, malate dehydrogenase, isocitrate dehydrogenase, acetaldehyde dehydrogenase, glyceraldehyde 3-phosphate dehydrogenase, pyruvate dehydrogenase, oxoglutarate dehydrogenase, and formate dehydrogenase. In yet a further embodiment of any of the foregoing embodiments, the dehydrogenase is a glucose dehydrogenase. In yet a further embodiment of any of the foregoing embodiments, the dehydrogenase is a glucose dehydrogenase from a bacterial species selected from the group consisting of *Bacillus megaterium, Bacillus subtilis, Gluconobacter suboxydans, Halobacterium mediterranei, Thermoplasma acidophilum,* and *Sulfolobus solfataricus.* In yet a further embodiment of any of the foregoing embodiments, the dehydrogenase is a glucose dehydrogenase from *Bacillus subtilis,* preferably wherein the glucose dehydrogenase from *Bacillus subtilis* comprises the polynucleotide sequence of SEQ ID NO:25 and/or comprises the polypeptide sequence of SEQ ID NO:1. In yet a further embodiment of any of the foregoing embodiments, the nicotinamide-based unnatural cofactor is selected from the group consisting of nicotinamide mononucleotide (NMN$^+$), 1-phenyl-1,4,-dihydronicotinamide (PNA$^+$), 1-benzyl-1,4-dihydronicotinamide (BNA$^+$), 1-(4-hydroxyphenyl)1,4-dihydronicotinamide (HPNA$^+$), 1-methyl-1,4-dihydronicotinamide (MNA$^+$), nicotinamide flucytosine dinucleotide (NFCD$^+$), nicotinamide mononucleoside (NR$^+$), 1-butyl-1,4,5,6-tetrahydropyridine-3-carboxamide, 1-(1-benzyl-1,4,5,6-tetrahydropyridin-3-yl) ethenone, 1-benzyl-1,4-dihydropyridine-3-carboxylic acid, and 1-benzyl-1,4,5,6-tetrahydropyridine-3-carbonitrile. In yet a further embodiment of any of the foregoing embodiments, the nicotinamide-based unnatural cofactor is nicotinamide mononucleotide (NMN$^+$). In yet a further embodiment of any of the foregoing embodiments, the engineered polypeptide has 100-fold or more catalytic activity towards the unnatural cofactor than the wild-type or parent polypeptide. In yet a further embodiment of any of the foregoing embodiments, the engineered polypeptide has 1000-fold or more catalytic activity towards the unnatural cofactor than the wild-type or parent polypeptide. In yet a further embodiment of any of the foregoing embodiments, the engineered polypeptide has a decrease of 30-fold or more in catalytic activity towards the natural cofactor than the wild-type or parent polypeptide. In yet a further embodiment of any of the foregoing embodiments, the engineered polypeptide has a decrease of 30-fold or more for NAD$^+$, and/or wherein the engineered polypeptide has a decrease of 1500-fold or more for NAD$^+$. In yet a further embodiment of any of the foregoing embodiments, the engineered polypeptide comprises a sequence that has at least 80% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:11, SEQ ID NO:12, SEQ ID NO:17, or SEQ ID NO:22, or comprises a sequence that has at least 80% sequence identity to a dehydrogenase polypeptide sequence having a UniProtKB/Swiss-Prot accession number of Q1JUP4.1, P11411.4, O57693.1, A4QB65.1, Q6L047.1, Q00796.4, Q97U30.1, O95479.2, P40047.4, Q8GAK7.1, O68282.1, O34425.1, P00367.2, P94527.1, P0DOV9.1, P56201.2, P77674.1, P27867.4, Q8CFX1.2, Q64442.3, Q7CRQ0.2, P07846.1, Q58D31.3, Q2MF22.1, Q2MFP3.1, Q2MF72.1, Q4R0W1.1, Q6L743.1, Q8GAK6.1, Q02912.1, Q52472.1, O93715.1, D4GS48.1, Q70KF0.1, Q53U21.1, Q5UY95.1, Q4R639.3, P00349.4, Q5R5F3.1, A6ZR27.1, P0DMQ6.1, D4GST8.1, Q7JK39.1, P46367.2, P96789.3, Q91100.1, Q9FWA3.1, Q9SH69.1, Q9FFR3.1, P31072.1, Q94KU2.1, P70718.1, Q2R480.1, P21577.4, Q6LZC3.1, Q9DCD0.3, P41574.1, Q8VXQ9.1, P41572.1, Q94KU1.1, P85968.1, P41581.1, P41573.1, O60037.1, P41576.2, P52207.1, P41580.1, P41579.1, P41578.1, P41577.1, P41575.1, P41583.1, P41582.1, P52208.1, Q17761.2, Q8TA03.1, Q89AX5.1, P78812.2, P57208.1, P12013.1, Q9Z8I3.1, P37754.1, O13287.1, Q977U7.1, Q05213.2, P86199.1, C8VP36.1, P50199.1, D4GP29.1, D4GP41.1, P40332.2, Q06539.4, P0DOV5.1, P22144.1, A0QQJ4.2, Q9FZ42.1, Q75KH3.2, Q9MA93.1, O80713.1, Q5KTS5.1, F4J300.1, F4J2Z7.1, Q9SCU0.1, Q703W7.1, P13203.4, Q53TZ2.1, Q7LYI9.1, Q97U21.1, Q6L1C8.1, Q97UH6.2, A8MAG0.1, D2RW30.1, A8M8R2.2, F0QYK7.2, F0QUB3.1, A4YGA7.1, D2S1F7.1, Q5V3L1.2, Q9HS17.1, D1YUK8.1, Q0W5A6.1, Q00612.3, P05370.3, P54996.1, P97324.3, P41571.1, P12646.2, Q29492.3, P11412.4, O55044.3, P31867.1, Q876L8.1, Q27638.1, Q7YS37.3, Q27464.1, Q43727.2, P07999.2, G4N708.1, D7UTD0.1, G4MZI3.1, Q9FY99.2, Q9LK23.1, Q9FJI5.1, Q8L743.2, P11410.2, Q43839.1, P29686.2, P37830.1, Q43793.1, P15588.1, P39484.1, P39483.1, P39482.1, Q64FW2.3, Q5FUK8.1, Q89AI7.1, P57405.1, Q9X0N9.1, Q9Z8U6.1, P77809.1, O14137.1, Q5FPE5.1, Q557D2.1, Q8SR89.1, Q93ZW0.1, Q42919.1, O24357.1, O00091.2, P41764.2, Q9ZKB2.1, P40288.1, O84188.1, P39485.1, P36959.1, P10528.1, P12310.2, P80869.2, P46336.1, Q24625.1, Q25537.1, Q25019.1, or Q23711.1. In yet a further embodiment of any of the foregoing embodiments, the engineered polypeptide comprises a sequence that has at least 90% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:11, SEQ ID NO:12, SEQ ID NO:17, or SEQ ID NO:22. In yet a further embodiment of any of the foregoing embodiments, the engineered polypeptide comprises a sequence that has at least 95% sequence identity to SEQ ID NO:1, SEQ ID NO:2, SEQ ID NO:3, SEQ ID NO:4, SEQ ID NO:5, SEQ ID NO:6, or SEQ ID NO:7. In yet a further embodiment of any of the foregoing embodiments, the engineered polypeptide comprises a sequence that has at least 98% sequence identity to SEQ ID NO:6, or SEQ ID NO:7. In yet a further embodiment of any of the foregoing embodiments, the engineered polypeptide comprises the sequence of SEQ ID NO:6, or SEQ ID NO:7 except that the sequence comprises 1, 2, 3, 4, 5, 6, 7, 8, 9, or 10 conservative amino acid substitutions, wherein the conservative amino acid substitutions do not significantly affect the dehydrogenase activity of the engineered polypeptide, and/or do not significantly affect the structural stability of the protein encoded by the engineered polypeptide. In yet a further embodiment of any of the foregoing embodiments, the engineered polypeptide comprises the sequence of SEQ ID NO:6, or SEQ ID NO:7 except that the sequence comprises 1, 2, 3, 4, or 5 conservative amino acid substitutions, wherein the conservative amino acid substitutions do not significantly affect the dehydrogenase activity of the engineered polypeptide and do not significantly affect the structural stability of the protein encoded by the engineered polypeptide. In yet a further embodiment of any of the foregoing embodiments, the engineered polypeptide comprises the sequence of SEQ ID NO:6, or SEQ ID NO:7.

In a certain embodiment, the disclosure also provides an expression vector comprising a polynucleotide sequence encoding an engineered polypeptide disclosed herein. In a further embodiment of the foregoing embodiment, the expression vector comprises the polynucleotide sequence of SEQ ID NO:25, except that the polynucleotide sequence has the following substitutions: the 'tat' triplet codon of bps 115 to 177 of SEQ ID NO:25 is replaced with a triplet codon selected from 'caa' or 'cag'; the 'gcc' triplet codon of bps 277 to 279 of SEQ ID NO:25 is replaced with a triplet codon selected from 'aaa' or 'aag'; the 'atc' triplet codon of bps 583 to 585 of SEQ ID NO:25 is replaced with a triplet codon selected from the group consisting of 'aga', 'agg', 'cgt', 'cgc', 'cga' and 'cgg'; and optionally, the 'agc' triplet codon of bps 49 to 51 of SEQ ID NO:25 is replaced with a triplet codon selected from 'gaa' or 'gag'. In yet a further embodiment of any of the foregoing embodiments, the expression vector is a cell-free expression vector or a microbial expression vector.

In a particular embodiment, the disclosure further provides a cell-free biotransformation system for converting a substrate into a product using a redox reaction with a re-cycled unnatural cofactor, comprising: a feedstock; a substrate; an engineered polypeptide of the disclosure, or an expression vector comprising a polynucleotide sequence encoding an engineered polypeptide disclosed herein; and one or more enzymes that can catalyze the transformation of the substrate into a product by using electrons from a nicotinamide-based unnatural cofactor, wherein the feedstock and substrate may be the same. In a further embodiment of the foregoing embodiment, the one or more enzymes are oxidoreductases, reductases, dehydrogenases, oxidases, monooxygenases, synthases, and hydroxylases. In yet a further embodiment of any of the foregoing embodiments, the one or more enzymes are selected from the group consisting of alcohol dehydrogenase (NAD), alcohol dehydrogenase (NADP), homoserine dehydrogenase, aminopropanol oxidoreductase, diacetyl reductase, glycerol dehydrogenase, propanediol-phosphate dehydrogenase, glycerol-3-phosphate dehydrogenase (NAD$^+$), D-xylulose reductase, L-xylulose reductase, lactate dehydrogenase, malate dehydrogenase, isocitrate dehydrogenase, HMG-CoA reductase EC, glucose oxidase, L-gulonolactone oxidase, thiamine oxidase, xanthine oxidase, acetaldehyde dehydrogenase, glyceraldehyde 3-phosphate dehydrogenase, pyruvate dehydrogenase, oxoglutarate dehydrogenase, biliverdin reductase, protoporphyrinogen oxidase, monoamine oxidase, dihydrofolate reductase, methylenetetrahydrofolate reductase, sarcosine oxidase, dihydrobenzophenanthridine oxidase, urate oxidase, nitrite reductase, nitrate reductase, glutathione reductase, thioredoxin reductase, sulfite oxidase, cytochrome c oxidase, coenzyme Q-cytochrome c reductase, catechol oxidase, laccase, cytochrome c peroxidase, catalase, myeloperoxidase, thyroid peroxidase, glutathione peroxidase, 4-hydroxyphenylpyruvate dioxygenase, renilla-luciferin 2-monooxygenase, cypridina-luciferin 2-monooxygenase, Firefly luciferase, watasenia-luciferin 2-monooxygenase, oplophorus-luciferin 2-monooxygenase EC, aromatase, CYP2D6, CYP2E1, CYP3A4, cytochrome P450 oxidase, nitric oxide synthase, phenylalanine hydroxylase, tyrosinase, superoxide dismutase, nitrogenase, and deiodinase. In yet a further embodiment of any of the foregoing embodiments, the one or more enzymes are selected from an enoate reductase XenA from *Pseudomonas putida*, a glucose dehydrogenase from *Bacillus megaterium*, an enoate reductase OYE3 from *Saccharomyces cerevisiae*, and/or a nitro reductase NfsB from *Escherichia coli*. In yet a further embodiment of any of the foregoing embodiments, the cell-free biotransformation system further comprises an unnatural cofactor selected from the group consisting of nicotinamide mononucleotide (NMN$^+$), 1-phenyl-1,4,-dihydronicotinamide (PNA$^+$), 1-benzyl-1,4-dihydronicotinamide (BNA$^+$), 1-(4-hydroxyphenyl)1,4-dihydronicotinamide (HPNA$^+$), 1-methyl-1,4-dihydronicotinamide (MNA$^+$), nicotinamide flucytosine dinucleotide (NFCD$^+$), nicotinamide mononucleoside (NR$^+$), 1-butyl-1,4,5,6-tetrahydropyridine-3-carboxamide, 1-(1-benzyl-1,4,5,6-tetrahydropyridin-3-yl) ethenone, 1-benzyl-1,4-dihydropyridine-3-carboxylic acid, and 1-benzyl-1,4,5,6-tetrahydropyridine-3-carbonitrile. In yet a further embodiment of any of the foregoing embodiments, the unnatural cofactor is NMN$^+$. In yet a further embodiment of any of the foregoing embodiments, the substrate and feedstock are glucose.

In a particular embodiment, the disclosure provides a whole-cell biomanufacturing system for converting a substrate into a product using a redox reaction with a re-cycled unnatural cofactor, comprising: a feedstock; a substrate; a recombinant microorganism that has been engineered to express an engineered polypeptide disclosed herein, or an expression vector comprising a polynucleotide sequence encoding an engineered polypeptide disclosed herein; and wherein the recombinant microorganism expresses one or more enzymes that can catalyze the transformation of the substrate into a product by using electrons from a nicotinamide-based unnatural cofactor, wherein the feedstock and substrate may be the same. In a further embodiment of the foregoing embodiment, the recombinant microorganism is a recombinant bacterium or a recombinant yeast. In yet a further embodiment of any of the foregoing embodiments, the recombinant microorganism is recombinant *Escherichia coli*. In yet a further embodiment of any of the foregoing embodiments, the recombinant microorganism has been modified by: introducing mutation(s) that disrupts one or more metabolic or enzymatic pathways of the recombinant microorganism; introducing one or polypeptides that results in overexpression of one or more metabolic or enzymatic pathways of the recombinant microorganism; introducing one or more mutations that results in shunting metabolites from one metabolic or enzymatic pathway to another pathway in the recombinant microorganism; introducing feedback mechanisms to either repress or activate enzymatic or metabolic pathways in the recombinant microorganism; or any combination of the foregoing. In yet a further embodiment of any of the foregoing embodiments, the recombinant microorganism comprises mutation(s) to disrupt genes of the Embden-Meyerhof-Parnas and/or the pentose phosphate pathway. In yet a further embodiment of any of the foregoing embodiments, the recombinant microorganism comprises mutation(s) which disrupts the expression of the zwf, gnd, and/or pgi genes. In yet a further embodiment of any of the foregoing embodiments, the recombinant microorganism comprises one or more polypeptides that overexpress genes associated with the Entner-Doudroff pathway. In yet a further embodiment of any of the foregoing embodiments, the recombinant microorganism comprises polypeptide(s) that enhance the expression of a glucose facilitator, a gluconate kinase, and/or a glutamate dehydrogenase. In yet a further embodiment of any of the foregoing embodiments, the one or more enzymes are oxidoreductases, reductases, dehydrogenases, oxidases, monooxygenases, synthases, and hydroxylases. In yet a further embodiment of any of the foregoing embodiments, the one or more enzymes are selected from the group consisting of alcohol dehydrogenase (NAD), alcohol dehydrogenase (NADP), homoserine dehydrogenase, aminopropanol oxidoreductase, diacetyl reductase, glycerol dehydrogenase, propanediol-phosphate dehydrogenase, glycerol-3-phosphate dehydrogenase (NAD$^+$), D-xylulose reductase, L-xylulose reductase, lactate dehydrogenase, malate dehydrogenase, isocitrate dehydrogenase, HMG-CoA reductase EC, glucose oxidase, L-gulonolactone oxidase, thiamine oxidase, xanthine oxidase, acetaldehyde dehydrogenase, glyceraldehyde 3-phosphate dehydrogenase, pyruvate dehydrogenase, oxoglutarate dehydrogenase, biliverdin reductase, protoporphyrinogen oxidase, monoamine oxidase, dihydrofolate reductase, methylenetetrahydrofolate reductase, sarcosine oxidase, dihydrobenzophenanthridine oxidase, urate oxidase, nitrite reductase, nitrate reductase, glutathione reductase, thioredoxin reductase, sulfite oxidase, cytochrome c oxidase, coenzyme Q-cytochrome c reductase, catechol oxidase, laccase, cytochrome c peroxidase, catalase, myeloperoxidase, thyroid peroxidase, glutathione peroxidase, 4-hydroxyphenylpyruvate dioxygenase, renilla-luciferin 2-monooxygenase, cypridina-luciferin 2-monooxygenase, Firefly luciferase, watasenia-luciferin 2-monooxygenase, oplophorus-luciferin 2-monooxygenase EC, aromatase, CYP2D6, CYP2E1, CYP3A4, cytochrome P450 oxidase, nitric oxide synthase, phenylalanine hydroxylase, tyrosinase, superoxide dismutase, nitrogenase, and deiodinase. In yet a further embodiment of any of the foregoing embodiments, the one or more enzymes are selected from an enoate reductase XenA from *Pseudomonas putida*, a glucose dehydrogenase from *Bacillus megaterium*, an enoate reductase OYE3 from *Saccharomyces cerevisiae*, and/or a nitro reductase NfsB from *Escherichia coli*. In yet a further embodiment of any of the foregoing embodiments, the whole-cell biomanufacturing system further comprises an unnatural cofactor selected from the group consisting of nicotinamide mononucleotide (NMN$^+$), 1-phenyl-1,4,-dihydronicotinamide (PNA$^+$), 1-benzyl-1,4-dihydronicotinamide (BNA$^+$), 1-(4-hydroxyphenyl)1,4-dihydronicotinamide (HPNA$^+$), 1-methyl-1,4-dihydronicotinamide (MNA$^+$), nicotinamide flucytosine dinucleotide (NFCD$^+$), nicotinamide mononucleoside (NR$^+$), 1-butyl-1,4,5,6-tetrahydropyridine-3-carboxamide, 1-(1-benzyl-1,4,5,6-tetrahydropyridin-3-yl) ethenone, 1-benzyl-1,4-dihydropyridine-3-carboxylic acid, and 1-benzyl-1,4,5,6-tetrahydropyridine-3-carbonitrile. In yet a further embodiment of any of the foregoing embodiments, the unnatural cofactor is NMN$^+$. In yet a further embodiment of any of the foregoing embodiments, the substrate and the feedstock are glucose.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the disclosure and, together with the detailed description, serve to explain the principles and implementations of the invention.

FIG. 13A-F demonstrates that GDH Ortho selectively provides reducing power for levodione production in *E. coli* whole cells. (A) GDH derives reducing power from glucose, which can support the biotransformation enzymes LVR, XenA, and ADH to convert ketoisophorone (KIP) into phorenol, levodione, and 4-hydroxyisophorone (HIP), respectively. (B-D) KIP conversion using resting *E. coli* cells expressing GDH and individual conversion enzymes (LVR, XenA, or ADH). Wild-type GDH (GDH wt) supported all three conversion reactions, while GDH Ortho specifically facilitated the conversion of KIP to levodione that was catalyzed by an NMNH-utilizing enzyme, XenA. (E-F) KIP conversion using resting *E. coli* cells expressing GDH and all three conversion enzymes (LVR, XenA, and ADH) simultaneously. Total product composition switched towards levodione production when GDH Ortho was expressed instead of GDH wt. The error bars represent one standard deviation above the mean of triplicate experiments. XenA, enoate reductase from *Pseudomonas putida*. LVR, levodione reductase from *Corynebacterium aquaticum*. ADH, alcohol dehydrogenase from *Ralstonia* sp.

DETAILED DESCRIPTION

Figure 1A:
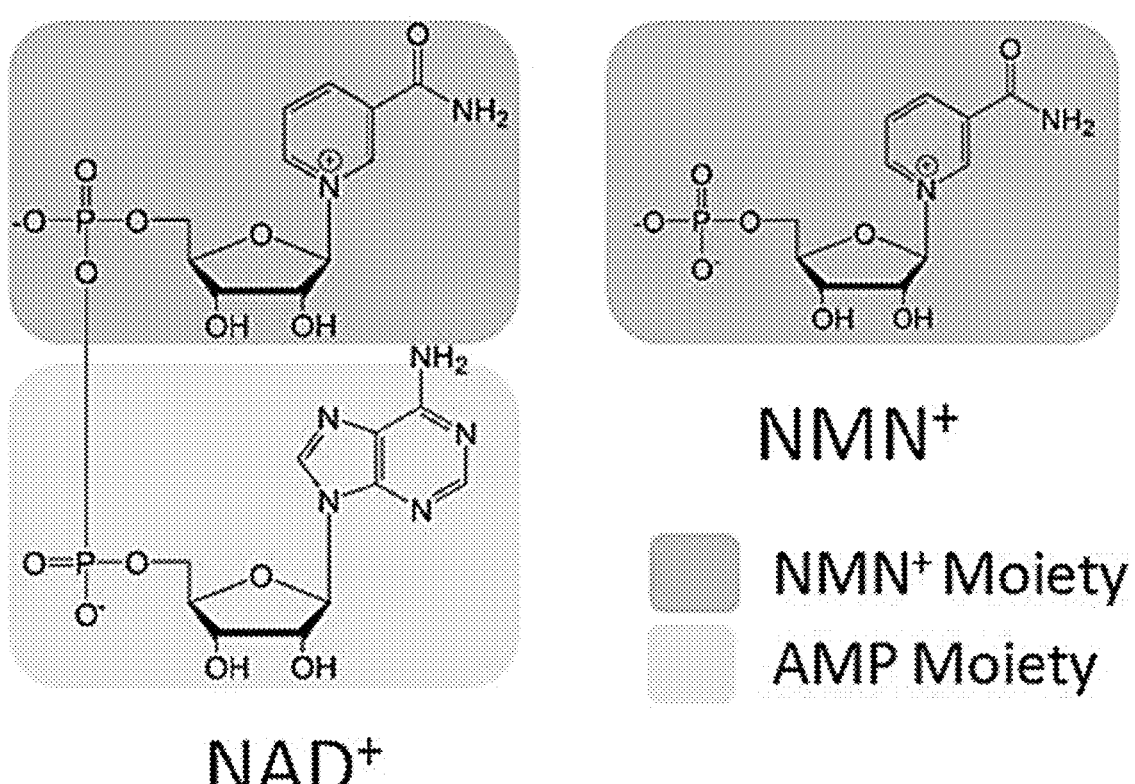
FIG. 1A-B presents (A) the structure of the natural redox cofactor NAD$^+$ and the unnatural redox cofactor nicotinamide mononucleotide (NMN$^+$). (B) Sliced representation of the NAD$^+$/NMN$^+$ binding pocket. Wild-type GDH (GDH WT) interacts with both the NMN$^+$ moiety (blue) and the AMP moiety (yellow) of NAD$^+$. The GDH Triple has an engineered positively charged region (black dashed lines) for the monophosphate of NMN$^+$ to anchor in a catalytically relevant conformation.

As used herein and in the appended claims, the singular forms "a," "an," and "the" include plural referents unless the context clearly dictates otherwise. Thus, for example, reference to "a polynucleotide" includes a plurality of such polynucleotides and reference to "the oxidoreductase" includes reference to one or more oxidoreductases, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned herein are incorporated by reference in full for the purpose of describing and disclosing methodologies that might be used in connection with the description herein. Moreover, with respect to any term that is presented in one or more publications that is similar to, or identical with, a term that has been expressly defined in this disclosure, the definition of the term as expressly provided in this disclosure will control in all respects.

Biomanufacturing, the synthesis of chemicals from renewable resources by engineered microbes, holds promise to transform the current fossil fuel-based chemical industry for a sustainable future. Although numerous fuels, pharmaceuticals, and commodities have been biomanufactured, the vast majority of these processes failed to proceed beyond lab scale because the productivity, titer, and yield are still low. This problem highlights the existence of a knowledge gap in the understanding of cell metabolism. This knowledge gap exists largely due to the extraordinary complexity of metabolic systems.

To overcome the complexity problem, one solution is to insulate the much simpler, engineered pathways in an orthogonal metabolic system which operates in parallel to the hosts' complex native metabolism. Catabolism and anabolism are the most universal orthogonal metabolic systems in nature. These two seemingly opposing processes coexist without interference largely because they each have a designated redox cofactor, $NAD^+$ and $NADP^+$, respectively. Therefore, it's been hypothesized that a third, orthogonal metabolic system can be established if one can introduce an unnatural redox cofactor inside the cells.

In addition to their applications in vivo, unnatural redox cofactors have also been explored as more cost-effective alternatives to $NAD(P)^+$ during in vitro biotransformation, where purified enzymes are used to manufacture chemicals. The majority of industrial biotransformation processes developed to date involve installing specific chiral centers using oxidoreductase enzymes, which require redox cofactors. Analogs of $NAD(P)^+$ with smaller sizes and simpler structures are more stable, easier to synthesize, and have faster mass transfer rate, which may greatly reduce the cost of in vitro biotransformation.

Enzymatic biotransformation has been regarded as a feasible solution to manufacture chiral chemicals in an affordable and environmentally friendly manner. In such processes, natural redox cofactors NAD(P)H are regenerated in situ by coupled enzymatic reactions. Recent studies have explored opportunities to replace the expensive and unstable natural redox cofactors with their simpler analogs. Compared to the natural redox cofactors, these unnatural cofactors typically retain the catalytically-essential nicotinamide moiety, but they are smaller in size and easier to synthesize. In addition to lowering costs, they also offer important advantages including higher stability and a faster diffusion rate. However, despite numerous efforts, two major roadblocks still remain which have impeded the widespread utilization of unnatural cofactors. First, most native enzymes have very low activities towards the simpler NAD(P)H analogs, which limits the scope of chemistry accessible. Second, an efficient and facile method to regenerate the reduced unnatural cofactors has been elusive. Ideally, such a method should also be "plug-in ready" to the existing biotransformation processes. Moreover, shifting enzymes' cofactor preference toward unnatural redox cofactors remains a challenging task.

Until recently, in situ regeneration of unnatural cofactors had relied on transition-metal catalysts, which has suffered from mutual inhibitory effects between the catalysts and the enzymes, and relatively low total turnover number (TTN). The recent development of an artificial metalloenzyme which utilizes a biotinylated iridium catalyst greatly enhanced the TTN to ~2000, albeit the synthesis of the metalloprotein catalyst is relatively complex. In 2017, the first enzymatic regeneration system for the unnatural cofactors through engineering the *Sulfolobus solfataricus* GDH (Ss GDH) was developed. However, the catalytic efficiency of the engineered enzyme was still low ($k_{cat}/K_m$ was ~5.17× $10^{-3}$ $mM^{-1}$ $s^{-1}$ for the cofactor 3-carbamoyl-1-phenethylpyridin-1-ium chloride). In fact, all efforts to date aiming at engineering non-flavin enzymes to accept simpler unnatural cofactors have met with limited success. These results suggest that shifting enzymes' cofactor preference toward simpler unnatural cofactors remains a challenging task. Accordingly, the main hurdle facing this protein engineering problem is a fundamental one: the binding affinity of proteins to ligands generally reduces as the size of ligands decreases, since fewer chemical grips are available in the ligands for interaction.

Figure 1B:
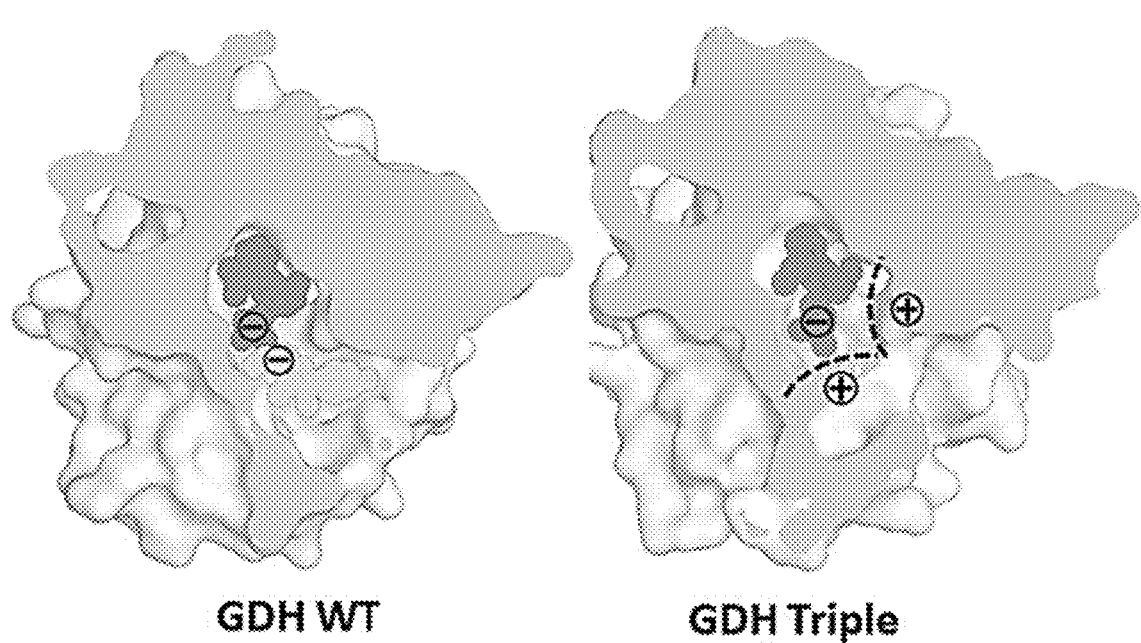

The disclosure provides a technical solution to foregoing problems by employing computational approaches to design novel interactions between the enzyme and the unnatural cofactor. In particular, the studies presented herein demonstrate that the glucose dehydrogenase from *Bacillus subtilis* (Bs GDH) could be reprogrammed to use nicotinamide mononucleotide (NMN$^+$) as efficiently as its natural redox cofactor (e.g., see FIG. 1). Compared to the wild type enzyme, the engineered polypeptide of the disclosure was found to have a $k_{cat}/K_M$ of ~0.51 mM$^{-1}$ s$^{-1}$ towards NMN$^+$, which corresponds to a ~1000-fold improvement. This represents the largest specificity switch towards non-natural nicotinamide cofactors achieved to date. The strength of computational design is highlighted in the discovery of two coupled pairwise mutations in which each mutation alone had a deleterious effect but act synergistically when combined. Coupled with an enoate reductase, the engineered polypeptides of the disclosure supported C═C double bond reduction with industrially relevant activity (~0.10 s$^{-1}$ initial turnover frequency) and robustness (TTN ~39,000). By exploring other enzymes with NMN(H)-utilizing capability, the engineered polypeptides disclosed herein supported C≡C triple bond reduction, nitro reduction, and supplied electrons to cytochrome P450.

Further demonstrated herein are whole cell experiments with *E. coli* which demonstrate that NMN$^+$ can mediate orthogonal reducing power delivery from glucose to the production of a pharmaceutical intermediate, levodione, while keeping other NAD(P)H-dependent competing reactions inactive. Additionally, it was demonstrated herein that the NMN$^+$-specific Bs GDH can support growth of *E. coli* on glucose. As such, the engineered polypeptide disclosed herein represents the first engineered enzyme capable of using an unnatural redox cofactor with sufficiently high flux to sustain life-essential central metabolism in vivo. Accordingly, the methodologies developed herein are generally applicable for the development of new enzymes that use non-natural redox cofactors, including in both cell free systems and whole cell systems.

Previous efforts to reprogram the nicotinamide coenzyme specificity have mainly been between NAD$^+$ and NADP$^+$. While these advances have shed light on how to modulate the specificity between natural nicotinamide compounds, redesigning a binding pocket towards use of a non-natural cofactor pose different, and a substantial number of challenges. To re-engineer the binding pocket, computational protein engineering tools were used in the studies presented herein to engineer various binding pockets with the desired specificity and affinity while maintaining the overall structural integrity of the protein. The computationally designed polypeptides presented herein, provides for the largest specificity switch towards a non-natural cofactor achieved to date.

Given the catalytic roles of the nicotinamide ring and its surrounding residues, a majority of the mutational candidates presented herein comprise residues that could form novel interactions with the negatively charged phosphate of NMN$^+$ or similarly negatively charged groups in other coenzymes. Therefore, polar and basic amino acids will be one of the main sources of engineering opportunities for the polypeptides presented herein. In particular, it is postulated herein that modifications and basic amino acids will impart or increase activity of the genetically modified proteins of the disclosure towards NMN$^+$ in any nicotinamide dependent oxidoreductase. The disclosure provides for a diverse ensemble of oxidoreductase scaffolds that can be modified to incorporate hydrogen bond donating amino acids that can bind with NMN$^+$. Thus, the disclosure provides for a large panel of genetically engineered enzymes that are capable of harboring NMN$^+$ for catalysis.

For in vitro biotransformation, supplying redox cofactors represents a major cost. In general, there may exist a trade-off between the cost of the cofactors and their catalytic activity. The high structural complexity of the natural cofactors affords optimal protein interaction but also attributes to high synthesis cost ($4500/kg for NADP$^+$ and $1500/kg for NAD$^+$). On the other hand, several previously explored unnatural cofactors, which have simple benzyl or aliphatic moieties attached to the nicotinamide, feature very low cost (less than $100/kg), but suffer from being less efficiently utilized by engineered enzymes. The unnatural cofactor NMN$^+$ used in the Examples presented herein therefore provides an improvement over the state of the art, by being substantially simpler and less expensive than natural cofactors ($250/kg for NMN$^+$), while still preserving the ribose phosphate group for enzymes to recognize (e.g., see FIG. 1).

Besides in vitro biotransformation, unnatural cofactors have also been suggested as important tools for building orthogonal metabolism in vivo. For in vivo metabolic engineering and synthetic biology, it is a long-standing challenge to make the artificial systems more independent of the hosts' metabolic background. For example, NAD(P)$^+$-dependent enzymes are superior biosensors for environmental monitoring and diagnostic applications, because they recognize an extremely broad range of chemicals with high sensitivity. However, they have a common drawback: their output signal, NAD(P)H generation or consumption, will be interfered with by the host's natural metabolism if they are used in vivo. Therefore, the NAD(P)$^+$-dependent biosensors have mainly been used in vitro as purified enzymes, which is not economical, stable, or scalable. This limitation may be overcome by using an orthogonal redox cofactor to relay the redox signals. Since NMN$^+$ is a naturally occurring metabolite in bacteria, yeasts, and mammalian cells, the methods and genetically modified proteins presented can be used to establish NMN(H)-based orthogonal electron circuits in vivo.

Further provided herein, are recombinant *E. coli* cells which have been engineered to require an NMN$^+$-based redox balance for growth. This growth phenotype may enable high-throughput selection, which can open opportunities for engineering NMN$^+$-dependent enzymes through directed evolution, or optimizing NMN$^+$-dependent pathways in vivo in a combinatorial manner. Similar redox balance-based, high-throughput selection platforms have been established for the two natural redox cofactors NAD$^+$ and NADP$^+$.

To increase the reaction rate of NMN$^+$-dependent whole-cell biotransformation, improving the catalytic efficiencies of the NMN$^+$-dependent enzymes, can be achieved as mentioned above, by computer modeling and testing. Further, engineering pathways for efficient NMN$^+$ biosynthesis and transportation that can be used to minimize and ultimately eliminate the need for NMN$^+$ supplementation. Such methods include, the use of bicistronic expression of recombinant nicotinamide phosphoribosyl transferase (Nampt) and phosphoribosyl pyrophosphate (PRPP) synthetase in the presence of nicotinamide (NAM) and lactose for producing NMN, as described in Marinescu et al. (*Scientific Reports* 8:12278 (2018)); or by modulating the activity of the Slc12a8 gene which encodes a NMN specific transporter, as described in Grozio et al. (Nature Metabolism, 1:47-57 (2019)).

Accordingly, current use of oxidoreductases with unnatural cofactors are limited by at least the following: (1) native enzymes have very low activity towards unnatural cofactors; (2) unnatural cofactors are small, and binding affinity of proteins to ligands reduces as the size the ligand is reduced; (3) current unnatural cofactors are not efficient; and (4) currently, there are no methods for regenerating the unnatural cofactors. The disclosure provides a technical solution to the above drawbacks by creating new and innovative polypeptides and proteins that can be used to recycle unnatural cofactors, such as NMN$^+$ to NMN(H), in an efficient manner. By doing so, the polypeptides and proteins of the disclosure can be coupled with other enzymes (e.g., oxidoreductases) to drive a diverse range of biotransformation chemistries. In particular, the disclosure provides for computationally redesigning the interactions between an enzyme (e.g., *Bacillus subtilis* glucose hydrogenase) and an unnatural cofactor (e.g., nicotinamide mononucleotide, NMN$^+$), by introducing novel interactions to increase electrostatic complementarity (binding) between the enzyme and cofactor while leaving important pieces unaltered (e.g., nicotinamide ring binding and catalytic residues). As shown in the Examples presented herein, a new enzyme was created that had a 1000-fold increase in catalytic efficiency over the wild-type enzyme towards NMN$^+$ (kcat/KM of ~0.51 mM$^{-1}$ s$^{-1}$). The techniques and methods of the disclosure can similarly be used to create additional enzymes to efficiently recycle unnatural cofactors by redesigning the interactions between the enzyme and an unnatural cofactor (e.g., NMN$^+$ or another unnatural cofactor). The disclosure further provides for a coupled enzymatic biotransformation system that can be used to perform a diverse range of biotransformation chemistries using synthetic biochemistry. Synthetic biochemistry, in which complex biochemical conversions are performed cell-free using a mixture of enzymes, affords potential advantages over traditional metabolic engineering techniques including: a higher level of flexibility in pathway design; greater control over component optimization; more rapid design-build-test cycles; and freedom from cell toxicity of intermediates or products. In particular, a cell-free system disclosed herein comprises a polypeptide of the disclosure that efficiently recycles an unnatural cofactor and one or more enzymes that utilizes the unnatural cofactor in converting substrates into desired products.

As will be described in more detail below, the disclosure provides for the generation and expression of novel polypeptides encoding enzymes that utilize unnatural cofactors many times more efficiently than the corresponding wild-type enzymes. In one embodiment, novel polypeptides have been engineered to more efficiently utilize the unnatural cofactor NMN$^+$. The polypeptides have been engineered from wild type or native polypeptides, such as the polypeptides presented in Table 1, to include specific amino acid substitutions at certain residues. While these polypeptides will be described in more detail below, it should be understood that polypeptides of the disclosure may also contain one or more modified amino acids. The presence of modified amino acids may advantageously increase efficiencies in the utilization of unnatural cofactors over polypeptides that do not contain said modified amino acids. Amino acid(s) are modified, for example, co-translationally or post-translationally during recombinant production (e.g., N-linked glycosylation at N—X—S/T motifs during expression in mammalian cells) or modified by synthetic means. Accordingly, a "mutant", "variant" or "modified" protein, enzyme, polynucleotide, gene, or cell, means a protein, enzyme, polynucleotide, gene, or cell, that has been altered or derived, or is in some way different or changed, from a parent protein, enzyme, polynucleotide, gene, or cell. A mutant or modified protein or enzyme is usually, although not necessarily, expressed from a mutant polynucleotide or gene.

As used herein, a "natural cofactor" refers to a non-protein chemical compound or metallic ion that is normally required for an enzyme's activity as a catalyst. Natural cofactors can be either loosely or tightly bound to the enzyme and can directly participate in the reaction. For example, NAD$^+$ or NADP$^+$ are natural cofactors for glucose dehydrogenase that are required for the enzyme's activity. In direct contrast, NMN$^+$ is not a natural cofactor for glucose dehydrogenase, and therefore is not required for the enzyme's in vivo activity.

As used herein, an "unnatural cofactor" refers to a chemical compound or metallic ion that is not normally required or associated with a particular enzyme's activity as a catalyst, but by the result of mutations or other changes, the enzyme's activity towards the unnatural cofactor can be greatly enhanced. For example, NMN$^+$ is not a natural cofactor for glucose dehydrogenase, but by introducing mutations into the polypeptide sequence for glucose dehydrogenase, the glucose dehydrogenase's activity towards NMN$^+$ can be greatly enhanced.

As used herein, a "mutation" means any process or mechanism resulting in a mutant protein, enzyme, polynucleotide, gene, or cell. This includes any mutation in which a protein, enzyme, polynucleotide, or gene sequence is altered, and any detectable change in a cell arising from such a mutation. Typically, a mutation occurs in a polynucleotide or gene sequence, by point mutations, deletions, or insertions of single or multiple nucleotide residues. A mutation includes polynucleotide alterations arising within a protein-encoding region of a gene as well as alterations in regions outside of a protein-encoding sequence, such as, but not limited to, regulatory or promoter sequences. A mutation in a gene can be "silent", i.e., not reflected in an amino acid alteration upon expression, leading to a "sequence-conservative" variant of the gene. This generally arises when one amino acid corresponds to more than one codon.

Non-limiting examples of a modified amino acid include a glycosylated amino acid, a sulfated amino acid, a prenlyated (e.g., farnesylated, geranylgeranylated) amino acid, an acetylated amino acid, an acylated amino acid, a pegylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols on CD-ROM (Humana Press, Towata, N.J.).

Recombinant methods for producing and isolating modified polypeptides of the disclosure are described herein. In addition to recombinant production, the polypeptides may be produced by direct peptide synthesis using solid-phase techniques (e.g., Stewart et al. (1969) Solid-Phase Peptide Synthesis (WH Freeman Co, San Francisco); and Merrifield (1963) *J. Am. Chem. Soc.* 85: 2149-2154). Peptide synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer.

"Oxidoreductase" refers to an enzyme that catalyzes the transfer of electrons from one molecule, the reductant, also called the electron donor, to another, the oxidant, also called the electron acceptor. This group of enzymes usually utilizes NADP or $NAD^+$ as cofactors. Examples of oxidoreductases include those enzymes that act on the CH—OH group of donors with $NAD^+$ or $NADP^+$ as an acceptor, including alcohol dehydrogenase (NAD) (EC 1.1.1.1), alcohol dehydrogenase (NADP) (EC 1.1.1.2), homoserine dehydrogenase (EC 1.1.1.3), aminopropanol oxidoreductase (EC 1.1.1.4), diacetyl reductase (EC 1.1.1.5), glycerol dehydrogenase (EC 1.1.1.6), propanediol-phosphate dehydrogenase (EC 1.1.1.7), glycerol-3-phosphate dehydrogenase ($NAD^+$) (EC 1.1.1.8), D-xylulose reductase (EC 1.1.1.9), L-xylulose reductase (EC 1.1.1.10), lactate dehydrogenase (EC 1.1.1.27), malate dehydrogenase (EC 1.1.1.37), isocitrate dehydrogenase (EC 1.1.1.42), and HMG-CoA reductase EC (1.1.1.88); enzymes that act on the CH—OH group of donors with oxygen as an acceptor, including glucose oxidase (EC 1.1.3.4), L-gulonolactone oxidase (EC 1.1.3.8), thiamine oxidase (EC 1.1.3.23), xanthine oxidase (EC 1.1.3.32); enzymes that act on the aldehyde or oxo group of donors with $NAD^+$ or $NADP^+$ as an acceptor, including acetaldehyde dehydrogenase EC (1.2.1.10), glyceraldehyde 3-phosphate dehydrogenase (EC 1.2.1.12), pyruvate dehydrogenase (EC 1.2.1.51), oxoglutarate dehydrogenase (EC 1.2.4.2); enzymes that act on the CH—CH group of donors with $NAD^+$ or $NADP^+$ as an acceptor, including biliverdin reductase (EC 1.3.1.24); enzymes that act on CH—CH group of donors with oxygen as an acceptor, including protoporphyrinogen oxidase (EC 1.3.3.4); enzymes that act on the CH—$NH_2$ group of donors, including monoamine oxidase (EC 1.4.3.4); enzymes that act on the CH—NH group of donors with $NAD^+$ or $NADP^+$ as an acceptor, including dihydrofolate reductase (EC 1.5.1.3), and methylenetetrahydrofolate reductase (EC 1.5.1.20); enzymes that act on the CH—NH group of donors with oxygen as an acceptor, sarcosine oxidase (EC 1.5.3.1), and dihydrobenzophenanthridine oxidase (EC 1.5.3.12); enzymes that act on other nitrogenous compounds as donors, including urate oxidase (EC 1.7.3.3), nitrite reductase (EC 1.7.99.3), and nitrate reductase (EC 1.7.99.4); enzymes that act on the sulfur group of donors, including glutathione reductase (EC 1.8.1.7), thioredoxin reductase (EC 1.8.1.9), and sulfite oxidase (EC 1.8.3.1); enzymes that act on the heme group of donors, including cytochrome c oxidase (EC 1.9.3.1); enzymes that act on diphenols and related substances as donors, including coenzyme Q-cytochrome c reductase (EC 1.10.2.2), catechol oxidase (EC 1.10.3.1), and laccase (EC 1.10.3.2); enzymes that act on peroxide as acceptor, including Cytochrome c peroxidase (EC 1.11.1.5), catalase (EC 1.11.1.6), myeloperoxidase (EC 1.11.1.7), thyroid peroxidase (EC 1.11.1.8), and glutathione peroxidase (EC 1.11.1.9); enzymes that act on single donors with incorporation of molecular oxygen, 4-hydroxyphenylpyruvate dioxygenase (EC 1.13.11.27), renilla-luciferin 2-monooxygenase (EC 1.13.12.5), cypridina-luciferin 2-monooxygenase (EC 1.13.12.6), Firefly luciferase (EC 1.13.12.7), watasenia-luciferin 2-monooxygenase (EC 1.13.12.8), and oplophorus-luciferin 2-monooxygenase EC (1.13.12.13); enzymes that act on paired donors with incorporation of molecular oxygen, including aromatase (EC 1.14.14.1), CYP2D6 (EC 1.14.14.1), CYP2E1 (EC 1.14.14.1), CYP3A4 (EC 1.14.14.1), Cytochrome P450 oxidase, nitric oxide synthase (EC 1.14.13.39), phenylalanine hydroxylase (EC 1.14.16.1), and tyrosinase (EC 1.14.18.1); and other oxidoreductases, including superoxide dismutase (EC 1.15.1.1), nitrogenase (EC 1.18.6.1), and deiodinase (EC 1.97.1.10). The above listing, provides for the classification of the foregoing enzymes by in the International Union of Biochemistry and Molecular Biology's Enzyme Commission [EC] numbering system. In a particular embodiment, the disclosure provides for an engineered polypeptide based upon an oxidoreductase disclosed above, that has been engineered to contain amino acid substitutions so as to enable the efficient recycling of an unnatural cofactor.

"Dehydrogenase" means an enzyme belonging to the group of oxidoreductases that oxidizes a substrate by reducing an electron acceptor, usually $NAD^+$/$NADP^+$ or a flavin coenzyme such as FAD or FMN. They also catalyze the reverse reaction, for instance alcohol dehydrogenase not only oxidizes ethanol to acetaldehyde in animals but also produces ethanol from acetaldehyde in yeast. In another embodiment, the disclosure provides for an engineered polypeptide based upon a dehydrogenase, that has been engineered to contain amino acid substitutions so as to enable the efficient recycling of an unnatural cofactor.

A "protein" or "polypeptide", which terms are used interchangeably herein, comprises one or more chains of chemical building blocks called amino acids that are linked together by chemical bonds called peptide bonds. An "enzyme" means any substance, preferably composed wholly or largely of protein, that catalyzes or promotes, more or less specifically, one or more chemical or biochemical reactions. A "native" or "wild-type" protein, enzyme, polynucleotide, gene, or cell, means a protein, enzyme, polynucleotide, gene, or cell that occurs in nature.

An "amino acid sequence" is a polymer of amino acids (a protein, polypeptide, etc.) or a character string representing an amino acid polymer, depending on context. The terms "protein," "polypeptide," and "peptide" are used interchangeably herein. "Amino acid" is a molecule having the structure wherein a central carbon atom is linked to a hydrogen atom, a carboxylic acid group (the carbon atom of which is referred to herein as a "carboxyl carbon atom"), an amino group (the nitrogen atom of which is referred to herein as an "amino nitrogen atom"), and a side chain group, R. When incorporated into a peptide, polypeptide, or protein, an amino acid loses one or more atoms of its amino acid carboxylic groups in the dehydration reaction that links one amino acid to another. As a result, when incorporated into a protein, an amino acid is referred to as an "amino acid residue."

A particular amino acid sequence of a given protein (i.e., the polypeptide's "primary structure," when written from the amino-terminus to carboxy-terminus) is determined by the nucleotide sequence of the coding portion of a mRNA, which is in turn specified by genetic information, typically genomic DNA (including organelle DNA, e.g., mitochondrial or chloroplast DNA). Thus, determining the sequence of a gene assists in predicting the primary sequence of a corresponding polypeptide and more particular the role or activity of the polypeptide or proteins encoded by that gene or polynucleotide sequence.

"Conservative amino acid substitution" or, simply, "conservative substitution" of a particular sequence refers to the replacement of one amino acid, or series of amino acids, with essentially identical amino acid sequences. One of skill will recognize that individual substitutions, deletions or additions which alter, add or delete a single amino acid or a percentage of amino acids in an encoded sequence result in "conservative variations" where the alterations result in the deletion of an amino acid, addition of an amino acid, or substitution of an amino acid with a chemically similar amino acid. For purposes of this disclosure a "conservative amino acid substitution" does significantly affect the catalytic activity towards an unnatural cofactor and/or structural stability of an engineered polypeptide disclosed herein. For example, the engineered polypeptide of the disclosure may comprise conservative amino acid substitutions in regions of the sequence that do not impact the binding site for the unnatural cofactor, e.g., conservative amino acid changes on the surface of the protein. Further, the sequence of an engineered polypeptide disclosed herein can be aligned with polypeptide sequence(s) from enzymes that have similar structures and/or catalytic activity in order to identify amino acids that likely do not affect the catalytic activity and/or structural stability of the engineered polypeptide. Moreover, there are many protein modeling programs available, including those specifically recited herein (e.g., Spartan and RosettaDesign), which can identify conservative amino acid substitutions with a high degree of probability/certainty that would not significantly affect the catalytic activity and/or structural stability of an engineered polypeptide disclosed herein (e.g., see Ng et al., Predicting Deleterious Amino Acid Changes *Genome Res* 11:863-874 (2001)). As such, it is expected that one of skill in the art could reasonably predict that the sequence for an engineered polypeptide disclosed herein can comprise a percentage of conservative amino acid substitutions, as is described more fully below, and still have similar or the same catalytic activity for the unnatural cofactor as a polypeptide sequence specifically recited herein (e.g., SEQ ID NO:6 or SEQ ID NO:7). Similar reasoning applies for the structural stability of an engineered polypeptide disclosed herein.

Conservative substitution tables providing functionally similar amino acids are well known in the art. For example, one conservative substitution group includes Alanine (A), Serine (S), and Threonine (T). Another conservative substitution group includes Aspartic acid (D) and Glutamic acid (E). Another conservative substitution group includes Asparagine (N) and Glutamine (Q). Yet another conservative substitution group includes Arginine (R) and Lysine (K). Another conservative substitution group includes Isoleucine, (I) Leucine (L), Methionine (M), and Valine (V). Another conservative substitution group includes Phenylalanine (F), Tyrosine (Y), and Tryptophan (W).

Thus, "conservative amino acid substitutions" of a polypeptide sequence disclosed herein include substitutions of a percentage, typically less than 5%, 6%, 7%, 8%, 9%, or 10%, of the amino acids of the polypeptide sequence, with a conservatively selected amino acid of the same conservative substitution group. Accordingly, a conservatively substituted variation of a polypeptide of the disclosure can contain 1, 2, 3, 4, 5, 6, 7, 8, 9, 10, 15, 20, 25, or any range that includes or is in between substitutions with a conservatively substituted variation of the same conservative substitution group.

It is understood that the addition of sequences which do not alter the encoded activity of a nucleic acid molecule, such as the addition of a non-functional or non-coding sequence, is a conservative variation of the basic nucleic acid. The "activity" of an enzyme is a measure of its ability to catalyze a reaction, i.e., to "function", and may be expressed as the rate at which the product of the reaction is produced. For example, enzyme activity can be represented as the amount of product produced per unit of time or per unit of enzyme (e.g., catalytic efficiency), or in terms of affinity or dissociation constants.

One of skill in the art will appreciate that many conservative variations of the nucleic acid constructs which are disclosed yield a functionally identical construct. For example, as discussed above, owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the polypeptides provided herein.

"Conservative variants" are proteins or enzymes in which a given amino acid residue has been changed without altering overall conformation and function of the protein or enzyme, including, but not limited to, replacement of an amino acid with one having similar properties, including polar or non-polar character, size, shape and charge. Amino acids other than those indicated as conserved may differ in a protein or enzyme so that the percent protein or amino acid sequence similarity (or identity) between any two proteins of similar function may vary and can be, for example, at least 30%, at least 50%, at least 70%, at least 80%, or at least 90%, as determined according to an alignment scheme. As referred to herein, "sequence similarity" means the extent to which nucleotide or protein sequences are related. The extent of similarity between two sequences can be based on percent sequence identity and/or conservation. "Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA (Lipman and Pearson, 1985; Pearson and Lipman, 1988). When using all of these programs, the preferred settings are those that results in the highest sequence similarity.

Non-conservative modifications of a particular polypeptide are those which substitute any amino acid not characterized as a conservative substitution. For example, any substitution which crosses the bounds of the six groups set forth above. These include substitutions of basic or acidic amino acids for neutral amino acids, (e.g., Asp, Glu, Asn, or Gln for Val, Ile, Leu or Met), aromatic amino acid for basic or acidic amino acids (e.g., Phe, Tyr or Trp for Asp, Asn, Glu or Gln) or any other substitution not replacing an amino acid with a like amino acid. Basic side chains include lysine (K), arginine (R), histidine (H); acidic side chains include aspartic acid (D), glutamic acid (E); uncharged polar side chains include glycine (G), asparagine (N), glutamine (Q), serine (S), threonine (T), tyrosine (Y), cysteine (C); nonpolar side chains include alanine (A), valine (V), leucine (L), isoleucine (I), proline (P), phenylalanine (F), methionine (M), tryptophan (W); beta-branched side chains include threonine (T), valine (V), isoleucine (I); aromatic side chains include tyrosine (Y), phenylalanine (F), tryptophan (W), and histidine (H).

A "parent" protein, enzyme, polynucleotide, gene, or cell, is any protein, enzyme, polynucleotide, gene, or cell, from which any other protein, enzyme, polynucleotide, gene, or cell, is derived or made, using any methods, tools or techniques, and whether or not the parent is itself native or mutant. A parent polynucleotide or gene encodes for a parent protein or enzyme. In a certain embodiment, a "parent" protein, enzyme, polynucleotide, gene, or cell, is a wild type protein, enzyme, polynucleotide, gene, or cell.

The disclosure provides for engineered polypeptides that have increased efficiency for an unnatural cofactor than the wild-type protein or polypeptide, including a wild type protein that has a sequence of SEQ ID NO:1, or a wild type protein which has a sequence presented in an accession number of: WP_003246720.1, EHA28975.1, WP_119899028.1, CDH98271.1, WP_038427366.1, WP_095431766.1, WP_041340171.1, WP_032726518.1, AXV60254.1, WP_044161863.1, WP_014478842.1, WP_003225027.1, OTQ88242.1, WP_059291954.1, WP_010333037.1, KIU10883.1, WP_105991496.1, WP_095010766.1, ANW06331.1, PTU26434.1, WP_103749790.1, WP_077671287.1, WP_019713327.1, WP_014475815.1, AAA22463.1, WP_071581042.1, AGE62243.1, WP_103031562.1, WP_003240219.1, WP_071578344.1, WP_024714517.1, KJJ40202.1, WP_010330813.1, WP_064814593.1, WP_100741417.1, WP_087993024.1, WP_039075845.1, WP_070081367.1, WP_061522816.1, WP_098080985.1, WP_082998974.1, WP_088461430.1, WP_025284235.1, WP_061573960.1, WP_104678928.1, WP_061669578.1, WP_099744414.1, WP_065521908.1, WP_065980712.1, WP_106360802.1, WP_061184372.1, WP_073536545.1, WP_053403598.1, WP_000287801.1, WP_088119901.1, WP_000287802.1, WP_054768130.1, WP_061654990.1, WP_097824161.1, WP_098487332.1, WP_053485906.1, WP_000287797.1, WP_098607945.1, WP_043068355.1, WP_078417142.1, WP_048520053.1, WP_098671912.1, WP_098487331.1, WP_045294049.1, SUV21072.1, or WP_097856719.1.

For example, the disclosure provides for polypeptides that exhibit increased catalytic efficiency for unnatural cofactors comprising a sequence that is: at least 85%, 90%, 95%, 98%, 99% identical to SEQ ID NO:1, wherein the sequence comprises a I195R mutation; at least 85%, 90%, 95%, 98%, 99% identical to SEQ ID NO:1, wherein the sequence comprises a A93K mutation; at least 85%, 90%, 95%, 98%, 99% identical to SEQ ID NO:1, wherein the sequence comprises a Y39Q mutation; at least 85%, 90%, 95%, 98%, 99% identical to SEQ ID NO:1, wherein the sequence comprises a S17E mutation; or at least 85%, 90%, 95%, 98%, 99% identical to SEQ ID NO:1, wherein the sequences comprises 2, 3, or 4 of the following mutations: I195R, A93K, Y39Q and S17E; wherein the foregoing polypeptides exhibit improved efficiency for unnatural cofactors compared to their corresponding parental (wild-type) protein lacking said I195R, A93K, Y39Q and/or S17E mutations. In a further embodiment, the disclosure provides for polypeptides that exhibit increased efficiency for unnatural cofactors comprising a sequence that is: at least 85%, 90%, 95%, 98%, 99% identical to SEQ ID NOs: 2, 3, 4, 5, 6, or 7. In yet a further embodiment, the disclosure provides a direct evolution method as described herein for generating polypeptides that exhibit increased efficiency for unnatural cofactors comprising a sequence that is: at least 85%, 90%, 95%, 98%, 99% identical to SEQ ID NOs:1, 2, 3, 4, 5, 6, or 7, wherein mutations are generated based upon analysis of the sequences presented in SEQ ID NO:8-24 using Spartan and RosettaDesign. Additional favorable amino acid modifications can be engineered into the polypeptides based upon design considerations using Spartan and RosettaDesign.

"Isolated polypeptide" refers to a polypeptide which is separated from other contaminants that naturally accompany it, e.g., protein, lipids, and polynucleotides. The term embraces polypeptides which have been removed or purified from their naturally-occurring environment or expression system (e.g., host cell or in vitro synthesis).

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure polypeptide composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species.

"Reference sequence" refers to a defined sequence used as a basis for a sequence comparison. A reference sequence may be a subset of a larger sequence, for example, a segment of a full-length gene or polypeptide sequence. Generally, a reference sequence can be at least 20 nucleotide or amino acid residues in length, at least 25 nucleotide or residues in length, at least 50 nucleotides or residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptides are typically performed by comparing sequences of the two polynucleotides or polypeptides over a "comparison window" to identify and compare local regions of sequence similarity.

"Sequence identity" means that two amino acid sequences are substantially identical (i.e., on an amino acid-by-amino acid basis) over a window of comparison. The term "sequence similarity" refers to similar amino acids that share the same biophysical characteristics. The term "percentage of sequence identity" or "percentage of sequence similarity" is calculated by comparing two optimally aligned sequences over the window of comparison, determining the number of positions at which the identical residues (or similar residues) occur in both polypeptide sequences to yield the number of matched positions, dividing the number of matched positions by the total number of positions in the window of comparison (i.e., the window size), and multiplying the result by 100 to yield the percentage of sequence identity (or percentage of sequence similarity). With regard to polynucleotide sequences, the terms sequence identity and sequence similarity have comparable meaning as described for protein sequences, with the term "percentage of sequence identity" indicating that two polynucleotide sequences are identical (on a nucleotide-by-nucleotide basis) over a window of comparison. As such, a percentage of polynucleotide sequence identity (or percentage of polynucleotide sequence similarity, e.g., for silent substitutions or other substitutions, based upon the analysis algorithm) also can be calculated. Maximum correspondence can be determined by using one of the sequence algorithms described herein (or other algorithms available to those of ordinary skill in the art) or by visual inspection.

As applied to polypeptides, the term substantial identity or substantial similarity means that two peptide sequences, when optimally aligned, such as by the programs BLAST, GAP or BESTFIT using default gap weights or by visual inspection, share sequence identity or sequence similarity. Similarly, as applied in the context of two nucleic acids, the term substantial identity or substantial similarity means that the two nucleic acid sequences, when optimally aligned, such as by the programs BLAST, GAP or BESTFIT using default gap weights (described elsewhere herein) or by visual inspection, share sequence identity or sequence similarity.

One example of an algorithm that is suitable for determining percent sequence identity or sequence similarity is the FASTA algorithm, which is described in Pearson, W. R. & Lipman, D. J., (1988) *Proc. Natl. Acad. Sci.* USA 85:2444. See also, W. R. Pearson, (1996) *Methods Enzymology* 266:227-258. Preferred parameters used in a FASTA alignment of DNA sequences to calculate percent identity or percent similarity are optimized, BL50 Matrix 15: –5, k-tuple=2; joining penalty=40, optimization=28; gap penalty –12, gap length penalty=–2; and width=16.

Another example of a useful algorithm is PILEUP. PILEUP creates a multiple sequence alignment from a group of related sequences using progressive, pairwise alignments to show relationship and percent sequence identity or percent sequence similarity. It also plots a tree or dendogram showing the clustering relationships used to create the alignment. PILEUP uses a simplification of the progressive alignment method of Feng & Doolittle, (1987) *J. Mol. Evol.* 35:351-360. The method used is similar to the method described by Higgins & Sharp, CABIOS 5:151-153, 1989. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity (or percent sequence similarity) relationship using the following parameters: default gap weight (3.00), default gap length weight (0.10), and weighted end gaps. PILEUP can be obtained from the GCG sequence analysis software package, e.g., version 7.0 (Devereaux et al., (1984) Nuc. Acids Res. 12:387-395).

Another example of an algorithm that is suitable for multiple DNA and amino acid sequence alignments is the CLUSTALW program (Thompson, J. D. et al., (1994) *Nuc. Acids Res.* 22:4673-4680). CLUSTALW performs multiple pairwise comparisons between groups of sequences and assembles them into a multiple alignment based on sequence identity. Gap open and Gap extension penalties were 10 and 0.05 respectively. For amino acid alignments, the BLOSUM algorithm can be used as a protein weight matrix (Henikoff and Henikoff, (1992) *Proc. Natl. Acad. Sci.* USA 89:10915-10919).

As mentioned above, additional favorable polypeptides sequences for engineering can be identified by using sequence alignment. For example, sequences that have sequence alignment of at least 80% to SEQ ID NO:1 and the accession numbers listed above would provide for such sequences. The modified polypeptide may then be assayed for unnatural efficiency using the methods described herein.

In a particular embodiment, an engineered polypeptide of the disclosure exhibits a fold increase in catalytic efficiency towards the unnatural cofactor in comparison to the corresponding parent or wild-type or parent polypeptide. In particular embodiment, the polypeptide of the disclosure has a fold increase of catalytic efficiency towards the unnatural cofactor over the corresponding parent polypeptide of at least 100 fold, 200 fold, 300 fold, 400 fold, 500 fold, 600 fold, 700 fold, 800 fold, 900 fold, 1000 fold, 1500 fold, 2000 fold, 2500 fold, 3000 fold, 4000 fold, 5000 fold, 6000 fold, 7000 fold, 8000 fold, 9000 fold, 10000 fold, 15000 fold, 20000 fold, 50000 fold, 100000 fold, or a range that includes or is between any two of the foregoing values.

It has also been shown that the catalytic efficiencies for using the unnatural cofactor can be predicted based on computer implemented protein design software. Such software, such as Spartan or RosettaDesign, allow for in silico modeling of coordinates and energies of the user designed proteins. For example, RosettaDesign searches for amino acid sequences that pack well, bury their hydrophobic atoms and satisfy the hydrogen bonding potential of polar atoms. RosettaDesign has been parameterized to return sequences with amino acid frequencies comparable to those found in naturally occurring proteins, and to partition the hydrophobic and polar residues between the surface and the core at naturally occurring frequencies. In general, when redesigning a naturally occurring protein ~65% of the residues will mutate. As expected, more sequence variability is seen on the surface of the protein where there are fewer packing constraints. In the core of the protein 45% of the residues mutate on average. RosettaDesign can be used to help design new protein structures or portions of proteins. In this case, the user must supply the backbone coordinates of the target structure. However, an arbitrarily chosen protein backbones may not be designable.

Using the methods described herein a number of polypeptides have been engineered to have increased catalytic efficiency towards an unnatural cofactor in comparison to the non-engineered polypeptide or wild-type peptide.

In view of the general applicability of the design methods and techniques described herein, additional polypeptides could be generated using different parental sequences which exhibit increased oxidoreductase catalytic efficiency towards an unnatural cofactor. Such different parental sequences could be selected from oxidoreductases and/or dehydrogenases which exhibit different substrate specificities; and oxidoreductases and dehydrogenases from different organisms or from chimeras generated thereof.

The disclosure further provides a cell-free system or whole-cell biomanufacturing systems to facilitate the biotransformation of a substrate into a desired product, comprising an engineered polypeptide of the disclosure that has improved catalytic efficiency towards an unnatural cofactor, and one or more polypeptides or proteins that encode enzymes that can use the same unnatural cofactor in a biotransformation reaction(s). For example, if $NMN^+$ (NHNH) is used as an unnatural cofactor, then the cell-free system of the disclosure comprises a engineered polypeptide disclosed herein that has improved catalytic efficiency towards $NMN^+$ and one or more polypeptides or proteins that encode an enoate reductase XenA from *Pseudomonas putida*, glucose dehydrogenase from *Bacillus megaterium*, enoate reductase OYE3 from *Saccharomyces cerevisiae*, or nitro reductase NfsB from *Escherichia coli*. Generally, the second polypeptide or protein can utilize, to some extent, the unnatural cofactor being re-cycled by the engineered polypeptides disclosed herein. It should be understood that the engineered polypeptides of the disclosure are not just limited to NMN⁺ and in-fact can be engineered to have greater catalytic efficiencies for additional unnatural cofactors, such as 1-phenyl-1,4,-dihydronicotinamide (PNA⁺), 1-benzyl-1, 4-dihydronicotinamide (BNA⁺), 1-(4-hydroxyphenyl)1,4-dihydronicotinamide (HPNA⁺), 1-methyl-1,4-dihydronicotinamide (MNA⁺), nicotinamide flucytosine dinucleotide (NFCD⁺), nicotinamide mononucleoside (NR⁺), 1-butyl-1, 4,5,6-tetrahydropyridine-3-carboxamide, 1-(1-benzyl-1,4,5, 6-tetrahydropyridin-3-yl) ethenone, 1-benzyl-1,4-dihydropyridine-3-carboxylic acid, and 1-benzyl-1,4,5,6-tetrahydropyridine-3-carbonitrile. Moreover, it has been found that nicotinamide-based unnatural cofactors can outperform natural coenzymes in certain studies (e.g., see Knaus et al., "Better than Nature: Nicotinamide Biomimetics That Outperform Natural Coenzymes" JACS 138:1033-1039 (2016)).

The disclosure further provides a whole cell biomanufacturing system to facilitate the biotransformation of a substrate into a desired product, comprising recombinant unicellular microorganism (e.g., bacteria and yeast) that have been modified to express an engineered polypeptide of the disclosure, i.e., a polypeptide that has improved catalytic efficiency towards an unnatural cofactor and optionally express one or more polypeptides or proteins that encode enzymes that can use the same unnatural cofactor in a biotransformation reaction(s). For example, if NMN⁺ (NHNH) is used as an unnatural cofactor, then the cell-free system of the disclosure comprises an engineered polypeptide disclosed herein that has improved catalytic efficiency towards NMN⁺, and one or more polypeptides or proteins that encode an enoate reductase XenA from *Pseudomonas putida*, glucose dehydrogenase from *Bacillus megaterium*, enoate reductase OYE3 from *Saccharomyces cerevisiae*, or nitro reductase NfsB from *Escherichia coli*. Generally, the second polypeptide or protein is dependent has some specificity for the unnatural cofactor being re-cycled by the engineered polypeptides disclosed herein. It should be understood that the engineered polypeptides of the disclosure are not just limited to NMN⁺ and in-fact can be engineered to have greater catalytic efficiencies for additional unnatural cofactors, such as 1-phenyl-1,4,-dihydronicotinamide (PNA⁺), 1-benzyl-1,4-dihydronicotinamide (BNA⁺), 1-(4-hydroxyphenyl)1,4-dihydronicotinamide (HPNA⁺), 1-methyl-1,4-dihydronicotinamide (MNA⁺), nicotinamide flucytosine dinucleotide (NFCD⁺), nicotinamide mononucleoside (NR⁺), 1-butyl-1,4,5,6-tetrahydropyridine-3-carboxamide, 1-(1-benzyl-1,4,5,6-tetrahydropyridin-3-yl) ethenone, 1-benzyl-1,4-dihydropyridine-3-carboxylic acid, and 1-benzyl-1,4,5,6-tetrahydropyridine-3-carbonitrile. The recombinant unicellular microorganisms described herein, may further comprise one or more introduced mutations to affect the unicellular microorganisms' metabolic or enzymatic pathway(s), including, but not limiting to, introducing mutation(s) that disrupts one or more metabolic or enzymatic pathways of the unicellular microorganism, introducing one or more polypeptides that results in overexpression of one or more metabolic or enzymatic pathways of the unicellular microorganism, introducing one or more mutations that results in shunting metabolites from one metabolic or enzymatic pathway to another in the unicellular microorganism, introducing feedback mechanisms to either repress or activate enzymatic or metabolic pathways in the unicellular microorganism, or any combination of the foregoing. In the Examples presented herein, it was shown a biomanufacturing system comprising engineered *E. coli* cells that requires NMN⁺-based redox balance to grow. This growth phenotype enables high-throughput selection, which allows for engineering NMN⁺-dependent enzymes through directed evolution, or optimizing NMN⁺-dependent pathways in vivo in a combinatorial manner. Similar redox balance-based, high-throughput selection platforms have been established for the two natural redox cofactors NAD⁺ and NADP⁺, which teachings of which indicate the possibilities of the biomanufacturing systems described herein (see e.g., Liang et al., *Metabolic engineering* 39, 181-191 (2017); Machado et al., *Metabolic engineering* 14, 504-511 (2012); and Zhang et al., *ACS synthetic biology* (2018).

The disclosure further provides that the methods and compositions described herein can be further defined by the following aspects (aspects 1 to 14):

1. An engineered polypeptide having dehydrogenase activity that exhibits increased catalytic efficiency for a nicotinamide-based unnatural cofactor relative to a wild-type or parent polypeptide that encodes a dehydrogenase, wherein the engineered polypeptide comprises 1, 2, 3, 4, 5, 6, 7, or 8 introduced amino acid substitutions in comparison to the sequence of the wild-type or parent polypeptide, preferably wherein the engineered polypeptide comprises 3, 4, 5, 6, 7, or 8 introduced amino acid substitutions in comparison to the sequence of the wild-type or parent polypeptide, more preferably wherein the engineered polypeptide comprises 3 or 4 introduced amino acid substitutions in comparison to the sequence of the wild-type or parent polypeptide, wherein the introduced amino acid substitutions increase electrostatic complementarity between the engineered polypeptide and the unnatural cofactor, preferably wherein the introduced amino acid substitutions promote the formation of hydrogen bonds between the engineered polypeptide and the unnatural cofactor, more preferably wherein the introduced amino acid substitutions promote the formation of hydrogen bonds between the engineered polypeptide and the nicotinamide-based unnatural cofactor in same binding site as the natural cofactor to the wild-type or parent polypeptide;

wherein the nicotinamide-based unnatural cofactor is a cofactor that is not normally utilized by the dehydrogenase encoded by the wild-type or parent polypeptide to catalyze a reaction, preferably wherein the nicotinamide-based unnatural cofactor is a cofactor that is not normally utilized by the dehydrogenase encoded by the wild-type or parent polypeptide to catalyze a reaction, more preferably wherein the dehydrogenase encoded by the wild-type or parent polypeptide cannot effectively and/or efficiently bind the nicotinamide-based unnatural cofactor due to poor or unfavorable electrostatic and/or steric interactions; and wherein the cofactor normally utilized by the wild-type or parent polypeptide is nicotinamide adenine dinucleotide (NAD⁺) or nicotinamide adenine dinucleotide phosphate (NADP⁺).

2. The engineered polypeptide of aspect 1, wherein the engineered polypeptide further comprises 1, 2, 3, 4, 5, 6, 7, or 8 additional amino acid substitutions in comparison to the wild-type or parent polypeptide, preferably wherein the engineered polypeptide further comprises 1, 2, 3, or 4, additional amino acid substitutions in comparison to the wild-type or parent polypeptide, wherein the additional amino acid substitutions disrupt electrostatic complementarity between the engineered polypeptide and NAD$^+$ or NADP$^+$, preferably wherein the additional amino acid substitutions disrupt hydrogen bond formation between the engineered polypeptide and NAD$^+$ or NADP$^+$, more preferably wherein the additional amino acid substitutions disrupt hydrogen bond formation between the engineered polypeptide and NAD$^+$ or NADP$^+$, while promoting or stabilizing hydrogen bond hydrogen bond formation between the engineered polypeptide and the nicotinamide-based unnatural cofactor.

3. The engineered polypeptide of aspect 1 or aspect 2, wherein the dehydrogenase is selected from the group consisting of alcohol dehydrogenase (NAD), alcohol dehydrogenase (NADP), homoserine dehydrogenase, glucose dehydrogenase, glycerol dehydrogenase, propanediol-phosphate dehydrogenase, glycerol-3-phosphate dehydrogenase (NAD$^+$), lactate dehydrogenase, malate dehydrogenase, isocitrate dehydrogenase, acetaldehyde dehydrogenase, glyceraldehyde 3-phosphate dehydrogenase, pyruvate dehydrogenase, oxoglutarate dehydrogenase, and formate dehydrogenase, preferably wherein the dehydrogenase is a glucose dehydrogenase;

and/or wherein the dehydrogenase is a glucose dehydrogenase from a bacterial species selected from the group consisting of *Bacillus megaterium, Bacillus subtilis, Gluconobacter suboxydans, Halobacterium mediterranei, Thermoplasma acidophilum*, and *Sulfolobus solfataricus*, preferably wherein the dehydrogenase is a glucose dehydrogenase from *Bacillus subtilis*, preferably wherein the glucose dehydrogenase from *Bacillus subtilis* comprises the polynucleotide sequence of SEQ ID NO:25 and/or comprises the polypeptide sequence of SEQ ID NO:1;

and/or wherein the nicotinamide-based unnatural cofactor is selected from the group consisting of nicotinamide mononucleotide (NMN$^+$), 1-phenyl-1,4,-dihydronicotinamide (PNA$^+$), 1-benzyl-1,4-dihydronicotinamide (BNA$^+$), 1-(4-hydroxyphenyl)1,4-dihydronicotinamide (HPNA$^+$), 1-methyl-1,4-dihydronicotinamide (MNA$^+$), nicotinamide flucytosine dinucleotide (NFCD$^+$), nicotinamide mononucleoside (NR$^+$), 1-butyl-1,4,5,6-tetrahydropyridine-3-carboxamide, 1-(1-benzyl-1,4,5,6-tetrahydropyridin-3-yl) ethenone, 1-benzyl-1,4-dihydropyridine-3-carboxylic acid, and 1-benzyl-1,4,5,6-tetrahydropyridine-3-carbonitrile, preferably wherein the nicotinamide-based unnatural cofactor is nicotinamide mononucleotide (NMN$^+$).

4. The engineered polypeptide of any one of the preceding aspects, wherein the engineered polypeptide has 100-fold or more catalytic activity towards the unnatural cofactor than the wild-type or parent polypeptide, preferably wherein the engineered polypeptide exhibits catalytic activity towards the unnatural cofactor of at least 100-fold, 200-fold, 300-fold, 400-fold, 500-fold, 600-fold, 700-fold, 800-fold, 900-fold, 1000-fold, 1500-fold, 2000-fold, 2500-fold, 3000-fold, 4000-fold, 5000-fold, 6000-fold, 7000-fold, 8000-fold, 9000-fold, 10,000-fold, or a range that includes or is between any two of the forgoing fold values; preferably, wherein the engineered polypeptide has 1000-fold or more catalytic activity towards the unnatural cofactor than the wild-type or parent polypeptide;

and/or wherein the engineered polypeptide has a decrease of 30-fold or more in catalytic activity towards the natural cofactor than the wild-type or parent polypeptide, preferably wherein the engineered polypeptide has a decrease of catalytic activity towards the natural cofactor than the wild-type or parent polypeptide of at least 35-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, 1200-fold, 1400-fold, 1600-fold, 2000-fold, 5,000-fold, or a range that includes or is between any two of the forgoing fold values, preferably, wherein the engineered polypeptide has a decrease of 30-fold or more for NAD$^+$, and/or wherein the engineered polypeptide has a decrease of 1500-fold or more for NAD$^+$.

5. The engineered polypeptide of any one of the preceding aspects, wherein the engineered polypeptide comprises a sequence that has at least 80% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:11, SEQ ID NO:12, SEQ ID NO:17, or SEQ ID NO:22, or comprises a sequence that has at least 80% sequence identity to a dehydrogenase polypeptide sequence having a UniProtKB/Swiss-Prot accession number of Q1JUP4.1, P11411.4, 057693.1, A4QB65.1, Q6L047.1, Q00796.4, Q97U30.1, 095479.2, P40047.4, Q8GAK7.1, 068282.1, 034425.1, P00367.2, P94527.1, P0DOV9.1, P56201.2, P77674.1, P27867.4, Q8CFX1.2, Q64442.3, Q7CRQ0.2, P07846.1, Q58D31.3, Q2MF22.1, Q2MFP3.1, Q2MF72.1, Q4R0W1.1, Q6L743.1, Q8GAK6.1, Q02912.1, Q52472.1, 093715.1, D4GS48.1, Q70KF0.1, Q53U21.1, Q5UY95.1, Q4R639.3, P00349.4, Q5R5F3.1, A6ZR27.1, P0DMQ6.1, D4GST8.1, Q7JK39.1, P46367.2, P96789.3, Q91100.1, Q9FWA3.1, Q9SH69.1, Q9FFR3.1, P31072.1, Q94KU2.1, P70718.1, Q2R480.1, P21577.4, Q6LZC3.1, Q9DCD0.3, P41574.1, Q8VXQ9.1, P41572.1, Q94KU1.1, P85968.1, P41581.1, P41573.1, 060037.1, P41576.2, P52207.1, P41580.1, P41579.1, P41578.1, P41577.1, P41575.1, P41583.1, P41582.1, P52208.1, Q17761.2, Q8TA03.1, Q89AX5.1, P78812.2, P57208.1, P12013.1, Q9Z8I3.1, P37754.1, 013287.1, Q977U7.1, Q05213.2, P86199.1, C8VP36.1, P50199.1, D4GP29.1, D4GP41.1, P40332.2, Q06539.4, P0DOV5.1, P22144.1, A0QQJ4.2, Q9FZ42.1, Q75KH3.2, Q9MA93.1, 080713.1, Q5KTS5.1, F4J300.1, F4J2Z7.1, Q9SCU0.1, Q703W7.1, P13203.4, Q53TZ2.1, Q7LYI9.1, Q97U21.1, Q6L1C8.1, Q97UH6.2, A8MAG0.1, D2RW30.1, A8M8R2.2, F0QYK7.2, F0QUB3.1, A4YGA7.1, D2S1F7.1, Q5V3L1.2, Q9HS17.1, D1YUK8.1, Q0W5A6.1, Q00612.3, P05370.3, P54996.1, P97324.3, P41571.1, P12646.2, Q29492.3, P11412.4, 055044.3, P31867.1, Q876L8.1, Q27638.1, Q7YS37.3, Q27464.1, Q43727.2, P07999.2, G4N708.1, D7UTD0.1, G4MZI3.1, Q9FY99.2, Q9LK23.1, Q9FJI5.1, Q8L743.2, P11410.2, Q43839.1, P29686.2, P37830.1, Q43793.1, P15588.1, P39484.1, P39483.1, P39482.1, Q64FW2.3, Q5FUK8.1, Q89AI7.1, P57405.1, Q9X0N9.1, Q9Z8U6.1, P77809.1, 014137.1, Q5FPE5.1, Q557D2.1, Q8SR89.1, Q93ZW0.1, Q42919.1, 024357.1, 000091.2, P41764.2, Q9ZKB2.1, P40288.1, 084188.1, P39485.1, P36959.1, P10528.1, P12310.2, P80869.2, P46336.1, Q24625.1, Q25537.1, Q25019.1, or Q23711.1, preferably, wherein the engineered polypeptide comprises a sequence that has at least 90% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:11, SEQ ID NO:12, SEQ ID NO:17, or SEQ ID NO:22, more preferably, wherein the engineered polypeptide comprises a sequence that has at least 95% sequence identity to SEQ ID NO:1, SEQ ID NO:2, SEQ ID NO:3, SEQ ID NO:4, SEQ ID NO:5, SEQ ID NO:6, or SEQ ID NO:7.

yet more preferably, wherein the engineered polypeptide comprises a sequence that has at least 98% sequence identity to SEQ ID NO:6, or SEQ ID NO:7.

yet more preferably, wherein the engineered polypeptide comprises the sequence of SEQ ID NO:6, or SEQ ID NO:7 except that the sequence comprises 1, 2, 3, 4, 5, 6, 7, 8, 9, 10, 11, 12, 13, 14, 15, or a range that includes or is between any two of the foregoing values, conservative amino acid substitutions, wherein the conservative amino acid substitutions do not significantly affect the dehydrogenase activity of the engineered polypeptide, and/or do not significantly affect the structural stability of the protein encoded by the engineered polypeptide, preferably, wherein the engineered polypeptide comprises the sequence of SEQ ID NO:6, or SEQ ID NO:7 except that the sequence comprises 1 to 10 conservative amino acid substitutions, more preferably, wherein the engineered polypeptide comprises the sequence of SEQ ID NO:6, or SEQ ID NO:7 except that the sequence comprises 1 to 5 conservative amino acid substitutions, yet more preferably, wherein the engineered polypeptide comprises the sequence of SEQ ID NO:6, or SEQ ID NO:7.

6. An expression vector comprising a polynucleotide sequence encoding for the engineered polypeptide of any one of the preceding aspects, preferably wherein the expression vector comprises a polynucleotide sequence encoding for an engineered polypeptide that comprises the sequence of SEQ ID NO:6, or SEQ ID NO:7;

and/or wherein the expression vector comprises the polynucleotide sequence of SEQ ID NO:25, except that the polynucleotide sequence has the following substitutions:

the 'tat' triplet codon of bps 115 to 177 of SEQ ID NO:25 is replaced with a triplet codon selected from 'caa' or 'cag', the 'gcc' triplet codon of bps 277 to 279 of SEQ ID NO:25 is replaced with a triplet codon selected from 'aaa' or 'aag', the 'atc' triplet codon of bps 583 to 585 of SEQ ID NO:25 is replaced with a triplet codon selected from the group consisting of 'aga', 'agg', 'cgt', 'cgc', 'cga' and 'cgg', and optionally, the 'agc' triplet codon of bps 49 to 51 of SEQ ID NO:25 is replaced with a triplet codon selected from 'gaa' or 'gag', and/or wherein the expression vector is a cell-free expression vector or a microbial expression vector.

7. A cell-free biotransformation system for converting a substrate into a product using a redox reaction with a re-cycled unnatural cofactor, comprising:

a feedstock;

a substrate;

the engineered polypeptide of any one of the previous aspects, or the expression vector of any one of the previous aspects; and one or more enzymes that can catalyze the transformation of the substrate into a product by using electrons from a nicotinamide-based unnatural cofactor, wherein the feedstock and substrate may be the same;

preferably, wherein the one or more enzymes are oxidoreductases, reductases, dehydrogenases, oxidases, monooxygenases, synthases, and hydroxylases;

more preferably, wherein the one or more enzymes are selected from the group consisting of alcohol dehydrogenase (NAD), alcohol dehydrogenase (NADP), homoserine dehydrogenase, aminopropanol oxidoreductase, diacetyl reductase, glycerol dehydrogenase, propanediol-phosphate dehydrogenase, glycerol-3-phosphate dehydrogenase (NAD$^+$), D-xylulose reductase, L-xylulose reductase, lactate dehydrogenase, malate dehydrogenase, isocitrate dehydrogenase, HMG-CoA reductase EC, glucose oxidase, L-gulonolactone oxidase, thiamine oxidase, xanthine oxidase, acetaldehyde dehydrogenase, glyceraldehyde 3-phosphate dehydrogenase, pyruvate dehydrogenase, oxoglutarate dehydrogenase, biliverdin reductase, protoporphyrinogen oxidase, monoamine oxidase, dihydrofolate reductase, methylenetetrahydrofolate reductase, sarcosine oxidase, dihydrobenzophenanthridine oxidase, urate oxidase, nitrite reductase, nitrate reductase, glutathione reductase, thioredoxin reductase, sulfite oxidase, cytochrome c oxidase, coenzyme Q-cytochrome c reductase, catechol oxidase, laccase, cytochrome c peroxidase, catalase, myeloperoxidase, thyroid peroxidase, glutathione peroxidase, 4-hydroxyphenylpyruvate dioxygenase, renilla-luciferin 2-monooxygenase, cypridina-luciferin 2-monooxygenase, Firefly luciferase, watasenia-luciferin 2-monooxygenase, oplophorus-luciferin 2-monooxygenase EC, aromatase, CYP2D6, CYP2E1, CYP3A4, cytochrome P450 oxidase, nitric oxide synthase, phenylalanine hydroxylase, tyrosinase, superoxide dismutase, nitrogenase, and deiodinase;

yet more preferably, wherein one or more enzymes are selected from an enoate reductase XenA from *Pseudomonas putida*, a glucose dehydrogenase from *Bacillus megaterium*, an enoate reductase OYE3 from *Saccharomyces cerevisiae*, and/or a nitro reductase NfsB from *Escherichia coli*.

8. The cell-free biotransformation system of aspect 7, wherein the cell-free biotransformation system further comprises an unnatural cofactor selected from the group consisting of nicotinamide mononucleotide (NMN$^+$), 1-phenyl-1,4,-dihydronicotinamide (PNA$^+$), 1-benzyl-1,4-dihydronicotinamide (BNA$^+$), 1-(4-hydroxyphenyl)1,4-dihydronicotinamide (HPNA$^+$), 1-methyl-1,4-dihydronicotinamide (MNA$^+$), nicotinamide flucytosine dinucleotide (NFCD$^+$), nicotinamide mononucleoside (NR$^+$), 1-butyl-1,4,5,6-tetrahydropyridine-3-carboxamide, 1-(1-benzyl-1,4,5,6-tetrahydropyridin-3-yl) ethenone, 1-benzyl-1,4-dihydropyridine-3-carboxylic acid, and 1-benzyl-1,4,5,6-tetrahydropyridine-3-carbonitrile;

and/or wherein the substrate and feedstock are glucose.

9. A whole-cell biomanufacturing system for converting a substrate into a product using a redox reaction with a re-cycled unnatural cofactor, comprising:

a feedstock;

a substrate;

a recombinant microorganism that has been engineered to express the engineered polypeptide of any one of the previous aspects, or the expression vector of any one of the previous aspects; and wherein the recombinant microorganism expresses one or more enzymes that can catalyze the transformation of the substrate into a product by using electrons from a nicotinamide-based unnatural cofactor, wherein the feedstock and substrate may be the same;

preferably, wherein the recombinant microorganism is a recombinant bacterium or a recombinant yeast;

yet more preferably, wherein the recombinant microorganism is recombinant *Escherichia coli.*

10. The whole-cell biomanufacturing system of aspect 9, wherein the recombinant microorganism has been modified by:

introducing mutation(s) that disrupts one or more metabolic or enzymatic pathways of the recombinant microorganism;

introducing one or polypeptides that results in overexpression of one or more metabolic or enzymatic pathways of the recombinant microorganism;

introducing one or more mutations that results in shunting metabolites from one metabolic or enzymatic pathway to another pathway in the recombinant microorganism;

introducing feedback mechanisms to either repress or activate enzymatic or metabolic pathways in the recombinant microorganism;

or any combination of the foregoing.

11. The whole-cell biomanufacturing system of aspect 9 or aspect 10, wherein the recombinant microorganism comprises mutation(s) to disrupt genes of the Embden-Meyerhof-Parnas and/or the pentose phosphate pathway;

preferably, wherein the recombinant microorganism comprises mutation(s) which disrupts the expression of the zwf, gnd, and/or pgi genes.

12. The whole-cell biomanufacturing system of any one of aspects 9 to 11, wherein the recombinant microorganism comprises one or more polypeptides that overexpress genes associated with the Entner-Doudroff pathway, preferably, wherein the recombinant microorganism comprises polypeptide(s) that enhance the expression of a glucose facilitator, a gluconate kinase, and/or a glutamate dehydrogenase.

13. The whole-cell biomanufacturing system of any one of aspects 9 to 12, wherein the one or more enzymes are oxidoreductases, reductases, dehydrogenases, oxidases, monooxygenases, synthases, and hydroxylases;

and/or wherein the one or more enzymes are selected from the group consisting of alcohol dehydrogenase (NAD), alcohol dehydrogenase (NADP), homoserine dehydrogenase, aminopropanol oxidoreductase, diacetyl reductase, glycerol dehydrogenase, propanediol-phosphate dehydrogenase, glycerol-3-phosphate dehydrogenase (NAD$^+$), D-xylulose reductase, L-xylulose reductase, lactate dehydrogenase, malate dehydrogenase, isocitrate dehydrogenase, HMG-CoA reductase EC, glucose oxidase, L-gulonolactone oxidase, thiamine oxidase, xanthine oxidase, acetaldehyde dehydrogenase, glyceraldehyde 3-phosphate dehydrogenase, pyruvate dehydrogenase, oxoglutarate dehydrogenase, biliverdin reductase, protoporphyrinogen oxidase, monoamine oxidase, dihydrofolate reductase, methylenetetrahydrofolate reductase, sarcosine oxidase, dihydrobenzophenanthridine oxidase, urate oxidase, nitrite reductase, nitrate reductase, glutathione reductase, thioredoxin reductase, sulfite oxidase, cytochrome c oxidase, coenzyme Q-cytochrome c reductase, catechol oxidase, laccase, cytochrome c peroxidase, catalase, myeloperoxidase, thyroid peroxidase, glutathione peroxidase, 4-hydroxyphenylpyruvate dioxygenase, renilla-luciferin 2-monooxygenase, cypridina-luciferin 2-monooxygenase, Firefly luciferase, watasenia-luciferin 2-monooxygenase, oplophorus-luciferin 2-monooxygenase EC, aromatase, CYP2D6, CYP2E1, CYP3A4, cytochrome P450 oxidase, nitric oxide synthase, phenylalanine hydroxylase, tyrosinase, superoxide dismutase, nitrogenase, and deiodinase;

and/or wherein the one or more enzymes are selected from an enoate reductase XenA from *Pseudomonas putida*, a glucose dehydrogenase from *Bacillus megaterium*, an enoate reductase OYE3 from *Saccharomyces cerevisiae*, and/or a nitro reductase NfsB from *Escherichia coli.*

14. The whole-cell biomanufacturing system of any one of aspects 9 to 13, wherein the whole-cell biomanufacturing system further comprises an unnatural cofactor selected from the group consisting of nicotinamide mononucleotide (NMN$^+$), 1-phenyl-1,4,-dihydronicotinamide (PNA$^+$), 1-benzyl-1,4-dihydronicotinamide (BNA$^+$), 1-(4-hydroxyphenyl)1,4-dihydronicotinamide (HPNA$^+$), 1-methyl-1,4-dihydronicotinamide (MNA$^+$), nicotinamide flucytosine dinucleotide (NFCD$^+$), nicotinamide mononucleoside (NR$^+$), 1-butyl-1,4,5,6-tetrahydropyridine-3-carboxamide, 1-(1-benzyl-1,4,5,6-tetrahydropyridin-3-yl) ethenone, 1-benzyl-1,4-dihydropyridine-3-carboxylic acid, and 1-benzyl-1,4,5,6-tetrahydropyridine-3-carbonitrile;

and/or wherein the substrate and the feedstock are glucose.

EXAMPLES

Figure 2:
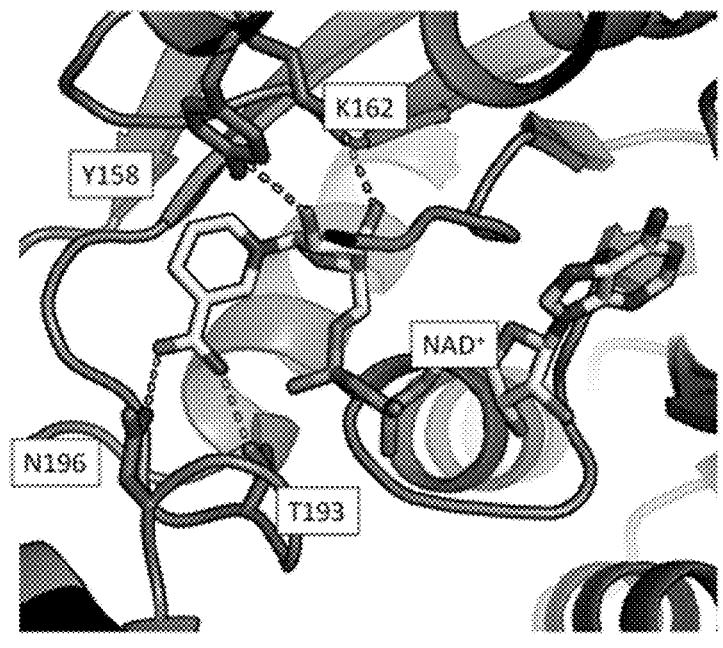
FIG. 2 presents the active site of glucose dehydrogenase with NAD$^+$ bound (PDB:1GCO). The catalytic residues Y158 and K162 participate in a hydrogen bond network with the hydroxyl groups on the ribose from the nicotinamide half of the NAD$^+$ molecule. The hydrogen bonds between N196 and T193 and the amide on NAD$^+$ suggest that they are potentially important to the orientation of NAD$^+$ into a catalytically relevant binding conformation prime for the hydride transfer step.

Bs GDH design strategy. The design process was focused on building and introducing novel interactions to NMN$^+$ while keeping the nicotinamide ring binding and catalytic residues unaltered. Since no crystal structures of Bs GDH was available, a HMMER search was performed to identify orthologous protein structures to determine essential versus designable residues of Bs GDH. Glucose dehydrogenase from *Bacillus megaterium* (Bm GDH, PDB: 1GCO) with NAD$^+$ bound was found from this search. Pairwise sequence alignment shows that Bs GDH and Bm GDH share a pairwise sequence identity of 83.5%. The NAD$^+$ in this crystal structure forms hydrogen bonds with Thr193 and Asn196 through the amide group on the catalytically essential nicotinamide moiety. In addition, Tyr158 and Lys162 of the catalytic triad hydrogen bond with both hydroxyl groups on the ribose of the nicotinamide half of NAD$^+$ (see FIG. 2). Therefore, the equivalent residues were kept constant during all subsequent design simulations and geometric constraints enforcing the chemical interactions observed in Bm GDH were used throughout subsequent simulations to prevent the interactions critical to the enzyme's function from being changed. Based on the Bm GDH structured, a molecular model of Bs GDH was produced using RosettaCM to obtain its three-dimensional structure and design simulations were carried out with RosettaDesign and Foldit, as detailed below.

Homology modeling and design of Bs GDH. Homology model of Bs GDH was produced using the RosettaCM protocol. The protein sequence of Bs GDH was used to search against the Protein Data Bank using HMMER to identify homologous crystal structures for modeling generation. 2,500 simulations were run to generate the models and the lowest scoring model based on total system energy was chosen as the starting point for design. An example run of the homology modeling simulation containing all inputs, command lines, and simulation variables can be found below.

The three-dimensional representation of nicotinamide mononucleotide (NMN$^+$) was built based on the nicotinamide adenine dinucleotide molecule found from the crystal structure 1GCO (A closely related enzyme with a pairwise sequence identity of 83.5% relative to Bs GDH). This output was then optimized and its conformers library generated using Spartan. The resulting conformers library was used for a docking and design simulation with the homology model of Bs GDH using RosettaDesign with distance and angle constraints present. A total of 1,000 simulations were run and the top 20 best scoring outputs sorted based on protein-ligand interface energy and total system energy were selected for further optimization and design using Foldit. During the design simulations, all side chains within 6 Å of for homology modeling run include alignment.fasta file, Bacil_thread.fasta file, setup_cm.sh file, template.pdb file, flags file, rosetta_cm.xml file, and hybridize.sh file (commandline submission file). For further information and description on these files please refer to Rosetta documentation on RosettaCM and RosettaDesign at: [rosettacommons.org/docs/latest/application_documentation/structure_prediction/RosettaCM and at [rosettacommons.org/docs/latest/application_documentation/design/enzyme-design. Due to the flexibility of NAD$^+$, the NAD$^+$ conformer's library was generated by sampling the representative ensembles of NAD$^+$ conformers listed in CoFactor database4. Overall, 31 conformers of NAD$^+$ were utilized for the calculation.

TABLE 1

| Accession numbers for proteins used in the Examples | | |
|---|---|---|
| Protein Name | Full Name | Protein ID |
| Ec PncC | NMN amidohydrolase | P0A6G3.1 (SEQ ID NO: 8) |
| Ec NadR | NMN adenylyl transferase | P27278.2 (SEQ ID NO: 9) |
| Ec Pgi | Glucose-6-phosphate isomerase | P0A6T1 (SEQ ID NO: 10) |
| Ec Zwf | NADP(+)-dependent glucose-6-phosphate dehydrogenase | NP_416366.1 (SEQ ID NO: 11) |
| Ec Gnd | 6-phosphogluconate dehydrogenase | P00350 (SEQ ID NO: 12) |
| Ec GntK | D-gluconate kinase | P46859 (SEQ ID NO: 13) |
| Ec NfsB | Oxygen-insensitive NAD(P)H nitro reductase | WP_000351487.1 (SEQ ID NO: 14) |
| Ft NadE | NAD(+) synthase | WP_003015145.1 (SEQ ID NO: 15) |
| Zm Glf | UDP-glucopyranose | AVZ41684.1 (SEQ ID NO: 16) |
| Sc OYE3 | NADPH dehydrogenase | NP_015154 (SEQ ID NO: 17) |
| Re GntK | Gluconate kinase | CAJ92320.1 (SEQ ID NO: 18) |
| Bs Gdh | Glucose 1-dehydrogenase | WP_003246720.1 (SEQ ID NO: 19) |
| Pp XenA | NADH: flavin oxidoreductase/NADH oxidase | WP_016711963.1 (SEQ ID NO: 20) |
| Ca LVR | Levodione Reductase | Q9LBG2.1 (SEQ ID NO: 21) |
| Rs ADH | Alcohol dehydrogenase | ACB78191.1 (SEQ ID NO: 22) |
| Bm BM3 | Bifunctional fatty acid monooxygenase | Addgene plasmid #85102 (SEQ ID NO: 23) |
| Ft NadV | Nicotinate phosphoribosyl transferase | WP_003018116.1 (SEQ ID NO: 24) | the NMN$^+$ ligand were allowed to be designed and any residues within 8 Å of the ligand were relaxed with backbone movements enabled. For the docking of NAD$^+$, the docking protocol was the same, but the conformer's library was generated in a different manner. Due to the flexibility of NAD$^+$, the NAD$^+$ conformer's library was generated by sampling the representative ensembles of NAD$^+$ conformers listed in CoFactor database. Overall, 31 conformers of NAD$^+$ were included in the conformer's library for the docking simulation. An example run of the design simulation containing all inputs, command lines, and simulation variables can be found below.

Rosetta run files. Files used for rosetta docking and design runs include Docking.xml file, Flags file, GluDH.enzdes.cst file (specify chemical constraints), GluDH_model.pdb file, X00.params file (describe properties of the NMN$^+$ ligand), and submit.sh file (commandline job submission). Files used Cloning, expression, and protein purification. The bacterial strains and plasmids used in this study are summarized in Table 2. The Bs GDH gene was amplified by PCR from chromosomal DNA of *Bacillus subtilis*. The resulting PCR products were gel-purified and assembled with vector backbone which contains a 6×His tag at the N-terminus (ColE1 ori, Amp$^R$) by the Gibson isothermal DNA assembly method. Site-directed mutagenesis was performed by introducing point mutations on the primers, followed by the assembly of the mutation-containing PCR fragments. *R. eutropha* gntK, *E. coli* nfsB, and *S. cerevisiae* OYE3 genes were amplified by PCR from corresponding chromosomal DNA. *C. aquaticum* lvr, R. sp adh, *F. tularensis* nadEV, *P. putida* xenA, and *Z. mobilis* glf were amplified from synthesized DNA templates. P450 BM3 was amplified from the plasmid pBsaBM3, a gift from Teruyuki Nagamune (Addgene plasmid #85102). All genes were also inserted in their respective vectors similarly. All PCR were performed using TaKaRa® PrimeSTAR Max DNA Polymerase. Cloning was done in *E. coli* XL1-Blue from Stratagene.

For the multi-gene plasmids, the genes were inserted sequentially. For example, pLZ219 was constructed by using a forward primer which binds immediately downstream of the Bs gdh gene on pSM107 together with a reverse primer which binds at the 5'-end of the Bs gdh gene, yielding a backbone DNA fragment containing the Bs gdh gene and the pBAD vector. To cyclize the plasmids, the backbone and amplified PCR fragments were assembled by Gibson assembly. Empty plasmid pSM105 and pSM108 were constructed by eliminating the Bs gdh from pEK101 and pSM107, respectively.

The multi-gene deletions in strains MX101, MX102, and MX103, were created by P1 phage transduction followed by flippase (FLP) recombinase-mediated excision of the corresponding kanamycin resistance cassette as described by Datsanko et al. (*Proceedings of the National Academy of Sciences* 97(12), 6640-6645 (2000)). Derivatives of *E. coli* K-12 strain BW25113 carrying single gene deletions were used as the donors, which carry a FLP recognition target (FRT)-flanked kanamycin resistance cassette in place of the target gene. Donors were obtained from the Yale *E. coli* Genetic Stock Center.

TABLE 2

| Plasmids and Strains used in the Examples | |
|---|---|
| | Description |
| Strains | |
| XL-1 Blue | Cloning strain |
| BL21(DE3) | Protein expression strain |
| BW25113 | *E. coli* $\Delta$(araD-araB)567, $\Delta$lacZ4787(::rrnB-3), $\lambda$-, rph-1, $\Delta$(rhaD-rhaB)568, hsdR514 |
| JW2670-1 | BW25113 $\Delta$pncC $\Delta$nadR::kan |
| MX101 | BW25113 $\Delta$pncC $\Delta$pgi $\Delta$zwf $\Delta$gntK::kan |
| MX102 | BW25113 $\Delta$pncC $\Delta$pgi $\Delta$zwf $\Delta$gntK::kan |
| MX103 | BW25113 $\Delta$pncC $\Delta$pgi $\Delta$zwf $\Delta$nadR $\Delta$gnd::kan |
| Plasmids | |
| pQE-30 | Expression vector with N-terminal 6 × His, Amp$^r$, ColE1 ori (Qiagen, Germantown, MD, USA) |
| GDH WT | pQE::Bs GDH wt |
| pLZ34 | pQE::Bs GDH N92A |
| pLZ35 | pQE::Bs GDH N92V |
| pLZ36 | pQE::Bs GDH G94S |
| pLZ37 | pQE::Bs GDH I195R |
| pLZ38 | pQE::Bs GDH I195S |
| pLZ39 | pQE::Bs GDH I195T |
| pLZ40 | pQE::Bs GDH S17Q P194N |
| pLZ41 | pQE::Bs GDH L19H I191S |
| pLZ42 | pQE::Bs GDH M143S |
| pLZ43 | pQE::Bs GDH M143T |
| pLZ45 | pQE::Bs GDH M143G L19G I224R |
| pLZ52 | pQE::Bs GDH I195R Y39Q |
| pLZ57 | pQE::Bs GDH I195R A93K |
| p50 | pQE::Pp XenA |
| pW001 | pQE::Ec NfsB |
| pW002 | pQE::Sc OYE3 |
| pLM50 | pQE::Bm BM3 wt |
| pLM51 | pQE::Bm BM3 W1046S |
| pEK101 | PLlacO1::Bs gdh, ColE1 ori, Amp$^R$ |
| pEK102 | PLlacO1::Pp xenA, ColE1 ori, Amp$^R$ |
| pLZ201 | PLlacO1::Bs gdh N92A, ColE1 ori, Amp$^R$ |
| pLZ202 | PLlacO1::Bs gdh N92V, ColE1 ori, Amp$^R$ |
| pLZ203 | PLlacO1::Bs gdh G94S, ColE1 ori, Amp$^R$ |
| pLZ204 | PLlacO1::Bs gdh I195R, ColE1 ori, Amp$^R$ |
| pLZ205 | PLlacO1::Bs gdh I195S, ColE1 ori, Amp$^R$ |
| pLZ206 | PLlacO1::Bs gdh I195T, ColE1 ori, Amp$^R$ |
| pLZ207 | PLlacO1::Bs gdh S17Q-P194N, ColE1 ori, Amp$^R$ |
| pLZ208 | PLlacO1::Bs gdh M143S, ColE1 ori, Amp$^R$ |
| pLZ209 | PLlacO1::Bs gdh M143T, ColE1 ori, Amp$^R$ |
| pLZ210 | PLlacO1::Bs gdh I195R-A93K-Y39Q, ColE1 ori, Amp$^R$ |
| pLZ211 | PLlacO1::Bs gdh I195R-Y39Q, ColE1 ori, Amp$^R$ |
| pLZ212 | PLlacO1::Bs gdh I195R-A93K, ColE1 ori, Amp$^R$ |
| pLZ213 | PLlacO1::Bs gdh A93K, ColE1 ori, Amp$^R$ |
| pLZ214 | PLlacO1::Bs gdh Y39Q, ColE1 ori, Amp$^R$ |
| pLZ215 | PLlacO1::Bs gdh A93K-Y39Q, ColE1 ori, Amp$^R$ |
| pLZ216 | PLlacO1::Bs gdh I195R-A93K-Y39Q-S17E, ColE1 ori, Amp$^R$ |
| pLZ217 | PBAD::Pp xenA, RSF ori, Spec$^R$ |
| pLZ218 | PBAD::Bs gdh I195R-A93K-Y39Q-S17E - Pp xenA, RSF ori, Spec$^R$ |
| pLZ219 | PBAD::Bs gdh - Pp xenA, RSF ori, Spec$^R$ |
| pLZ220 | PBAD::Bs gdh - Ca lvr, RSF ori, Spec$^R$ |
| pLZ221 | PBAD::Bs gdh I195R-A93K-Y39Q-S17E - Ca lvr, RSF ori, Spec$^R$ |
| pLZ222 | PBAD::Ca lvr, RSF ori, Spec$^R$ |
| pLZ223 | PBAD::Bs gdh - Rs adh, RSF ori, Spec$^R$ |

TABLE 2-continued

| Plasmids and Strains used in the Examples |
| --- |

| | Description |
| --- | --- |
| pLZ224 | PBAD::Bs gdh I195R-A93K-Y39Q-S17E - Rs adh, RSF ori, Spec$^R$ |
| pLZ225 | PBAD::Rs adh, RSF ori, Spec$^R$ |
| pLZ226 | PLlacO1::Pp xenA - Ca lvr - Rs adh, ColE1 ori, Amp$^R$ |
| pSM101 | PLlacO1::Bm BM3, ColE1 ori, Amp$^R$ |
| pSM102 | PLlacO1::Bm BM3 W1046S, ColE1 ori, Amp$^R$ |
| pSM103 | PLlacO1::Ft nadEV - Zm glf - Re gntK, ColE1 ori, Amp$^R$ |
| pSM104 | PLlacO1::Zm glf ColE1 ori, Amp$^R$ |
| pSM105 | PLlacO1::Empty, ColE1 ori, Amp$^R$ |
| pSM106 | PBAD::Bs gdh I195R-A93K-Y39Q-S17E, RSF ori, Spec$^R$ |
| pSM107 | PBAD::Bs gdh, RSF ori, Spec$^R$ |
| pSM108 | PBAD::Empty, RSF ori, Spec$^R$ |
| pSM109 | PLlacO1::Zm glf p15A ori, Cm$^R$ |
| pSM110 | PLlacO1::Zm glf ColE1 ori, Cm$^R$ |
| pWB201 | PLlacO1::Sc OYE3, ColE1 ori, Amp$^R$ |
| pWB202 | PLlacO1::Ec nfsB, ColE1 ori, Amp$^R$ |
| pWB203 | PLlacO1::Ft nadEV, ColE1 ori, Amp$^R$ |

Abbreviations indicate source of genes: Ca, *Corynebacterium aquaticum*; Bm, *Bacillus megaterium*; Bs, *Bacillus subtilis*; Ft, *Francisella tularensis*; Pp, *Pseudomonas putida*; Re, *Ralstonia eutropha* H16; Rs, *Ralstonia* sp.; Sc, *Saccharomyces cerevisiae*; Zm, *Zymomonas mobilis*.

Proteins were purified as 6×His tag fusion at the N-terminus. *E. coli* BL21 (DE3) with plasmids were inoculated into LB medium with 200 mg L$^{-1}$ ampicillin. Cells were induced with 0.5 mM IPTG and expressed for 24 hours at 30° C. with shaking at 250 rpm. BM3 cytochrome P450 was extracted with the EMD Millipore™ BugBuste Plus Lysonase Kit and purified using the HisPur™ Ni-NTA Superflow Purification System according to the manufacturer's instructions. Other proteins were purified using His-Spin Protein Miniprep kit (Zymo Research Corporation, CA). The purified proteins were quantified by Bradford assay.

Intracellular cofactor concentration analytical methods. Liquid chromatography was performed on a Waters ACQUITY UPLC with a Waters ACQUITY UPLC CSH C18 column (1.7 m×2.1 mm×50 mm). Mobile phases used in the separation were (A) water with 2% acetonitrile and 0.2% acetic acid and (B) acetonitrile with 0.2% acetic acid. The compounds were separated with a linear gradient from 10% to 90% buffer B over 1 minute, held at 90% buffer B for 1 minute, then returned to 10% buffer B and held at 10% buffer B for 1 minute. Flow rate was held constant at 0.3 mL/min. 10 L of sample was injected for analysis.

MS/MS detection was performed by a Waters Micromass Quattro Premier XE Mass Spectrometer operating in positive ion, MRM mode. Capillary voltage was set to 3.3 kV. Desolvation gas flow rate was 800 L/h at 300° C. Cone gas flow rate was 50 L/h. The source was maintained at 120° C. Primary mass, fragment mass, cone voltages, and collision energies for each compound are listed in Table 3.

TABLE 3

| Compound mass fragmentation and MS parameter | | | | |
| --- | --- | --- | --- | --- |
| Compound | Primary Mass | Secondary Mass | Cone Voltage | Collision Energy |
| MNA$^+$ (IS) | 137 | 94 | 20 | 20 |
| NMN$^+$ | 335 | 123 | 10 | 10 |
| NAD$^+$ | 664 | 135.9 | 20 | 40 |

GC-FID analytical methods. All gas chromatography was performed on an Agilent 6850 (Agilent Technologies, Santa Clara, Calif., USA) equipped with a flame ionization detector (FID). An Agilent DB-WAXetr capillary column (30 m×0.56 mm×1 μm) was used for separation. The inlet and detector were held at 250° C. and 260° C., respectively. The GC was operated in constant pressure mode with a pressure of 3.66 psi. Helium was used as the carrier gas. Air and Hydrogen were supplied to the FID at 350 mL/min and 40 mL/min respectively. All gasses were purchased from Airgas (Radnor Township, Pa.). 5 μL of sample was injected with a split ratio of 2:1. 13

For analysis of citral and its reduction product citronellal, the oven was initially held at 150° C. for 10 minutes and then ramped at a rate of 45° C./min to 240° C. Citral and citronellal eluted at 9.32 and 4.50 minutes, respectively. Octanol was used as an internal standard.

For analysis of trans-2-hexen-1-al and its reduction product trans-2-hexan-1-al, the oven was initially held at 50° C. for 1 minute, the oven was ramped at 15° C./min to 120° C., then ramped at 20° C./min to 230° C., and held for 3 minutes. Trans-2-hexen-1-al and trans-2-hexan-1-al eluted at 6.41 minutes and 4.78 minutes, respectively. Octanol was used as an internal standard.

For analysis of 4-phenyl-3-butyne-2-one (containing C≡C triple bond) and its fully reduced product 4-phenyl-2-butanone, as well as the intermediate 4-phenyl-2-butene-2-one (containing C=C double bond), the oven was initially held at 200° C. for 1 minute, then ramped at 5° C./min to 230° C., and held for 1 minute. Octanol was used for an internal standard. In vitro ketoisophorone reduction to levodione was analyzed using the same method. Elution times were 4-phenyl-3-butyne-2-one (5.53 minutes), 4-phenyl-2-butene-2-one (6.76 minutes), 4-phenyl-2-butanone (4.55 minutes), ketoisophorone (3.65 minutes), levodione (4.08 minutes), octanol (2.80 minutes).

For analysis of in vivo ketoisophorone biotransformation. The oven was held at 200° C. for 15 minutes. Elution times are as follows: Octanol (2.80 minutes), ketoisophorone (3.76 minutes), levodione (7.25 minutes), phorenol (8.35 minutes), and 4-hydroxyisophorone (12.90 minutes).

GDH enzymatic assays. The GDH activity was measured as described in Hilt et al. (*Biochimica et biophysica acta* 1076(2):298-304 (1991)). The reactions were started by adding the purified protein to the assay mixture containing 35 mM Tris-HCl buffer (pH 8.0), 3 mM NAD$^+$, NADP$^+$ or NMN$^+$ and 140 mM glucose. The absorbance variation at 340 nm was detected by a spectrophotometer at 25° C.

Enzyme assay conditions: The enzymatic buffer contained 200 mM phosphate buffer (pH 7.5), 5 mM ketoisophorone, and 0.2 mM NADPH, NADH, or NMNH, and appropriate amount of purified XenA protein. The initial reaction rate was quantified by absorbance variation at 340 nm using a spectrophotometer at 37° C. Reactions with no ketoisophorone added were performed to quantify the non-specific reaction rate. The net reaction rate as shown in FIG. 13 was calculated by subtracting the non-specific reaction rate from the total reaction rate. For generating NMNH, a microcentrifuge tube (2 mL) containing 35 mM Tris-HCl (pH 8.0), 4 mM NMN⁺, 1 M NaCl and 140 mM glucose, was incubated for ~3 hr at 30° C. with purified Bs GDH I195R. An aliquot of this reaction system was taken to measure the accumulation of NMNH by reading absorbance at 340 nm. The proteins in the reaction were removed by filtering the mixture with centrifugal filter units (Amicon Ultra-0.5 Centrifugal Filter Units, Millipore, USA). The solvent was evaporated, and the residue was collected to give NMNH as a yellowish oil.

Coupled enzymatic biotransformation. All biotransformation reactions were performed in buffer A at 30° C. for 24 hours. Reaction buffer A, modified from that disclosed in Chaparro-Riggers et al., *Advanced Synthesis & Catalysis* 349(8-9):1521-1531 (2007), contained 200 mM potassium phosphate buffer (pH 7.5), 1 M NaCl, 300 mM D-glucose, 6 mM NMN⁺ (or NADP⁺ as the positive control), and substrates. All assays were performed in triplicate, with no proteins or no cofactors added as negative controls. The protein loading for GDH variants was kept at 0.33 mg mL⁻¹ or 11.7 µM. The various enzymes for biotransformation reactions were added at the concentration of 0.75 mg mL⁻¹.

For XenA-GDH coupled cycling assays, the substrates ketoisophorone, citral, or trans-2-hexen-1-al were added at 33 mM, 10 mM, or 50 mM, respectively. For the OYE3-GDH coupled cycling assays, the substrate 4-phenyl-3-butyn-2-one was added at 5 mM. At various time points over 24 hours, 100 µL samples were taken and extracted with 100 µL ethyl acetate. Conversion was determined via GC-FID with octanol as an internal standard (see below). For NfsB-GDH coupled cycling assays, 2 mM nitrofurazone was used as the substrate. Nitrofurazone conversion was measured spectroscopically at 400 nm and quantification was performed using a standard curve. The initial levels of the above-mentioned substrates were mainly determined by their solubility in the assay buffer. For BM3-GDH coupled cycling assays, 50 µM cytochrome c (C2506 Sigma) was used as the substrate. The reduction of cytochrome c was measured spectroscopically at 550 nm. and the quantification was performed using extinction coefficient $\varepsilon_{550}$ of 21.1 mM⁻¹ cm⁻¹.

GDH Total Turnover Number (TTN) Determination. Total turnover number (TTN) was determined by the number of moles of product formed divided by the moles of purified GDH added. The assays were performed in reaction buffer A, as shown above, at 30° C. Ketoisophorone (33 mM) was used as the substrate. The reaction was started by spiking purified proteins (0.0132 mg mL⁻¹ or 0.47 µM for GDH, 0.75 mg mL⁻¹ for XenA). Samples were taken every 12 hours for 96 hours. The extraction and GC-FID analysis were performed using a similar method as mentioned above.

Quantification of intracellular NMN and NAD levels. A plasmid containing Ft nadE and nadV (pWB203) was transformed into *E. coli* strains BW25113, JW2670-1, and MX101 to examine their effects on NMN⁺ generation. Overnight cultures were grown at 30° C. while shaking at 250 rpm in 2×YT media containing 0.1 mM IPTG, 0.2% D-glucose, and appropriate antibiotics for 12 hours. To cultivate cells for nucleotide analysis, 10 mL of 2×YT media containing 0.5 mM IPTG, 1 mM nicotinamide, and appropriate antibiotics in a 50 mL conical tube was inoculated with 1% v/v overnight culture. Tubes were incubated at 30° C. at 250 rpm for 4 hours.

Before harvesting the cells, the cell density was measured at 600 nm. 1 mL of culture was pelleted in a 1.5 mL microcentrifuge tube. The supernatant was removed by pipetting. The cell pellet was washed once with 1 mL of room temperature deionized water, re-pelleted, and the supernatant was removed by pipetting. The cells were lysed with 1 mL of 95° C. 1% formic acid with 1 µM 1-methylnicotinamide as an internal standard. The cells were incubated at 95° C. for 2 minutes while intermittently vortexing to ensure complete lysis. The lysates were quenched in an ice water bath before pelleting cell debris. The supernatant was run on a UPLC-MS/MS system for analysis. Values from LC/MS/MS were correlated back to intracellular concentration using the number of cells per $OD_{600}$ of 1 in 1 mL of culture=$1×10^9$ and the intracellular volume of an *E. coli* cell as $1×10^{-15}$ L/cell.

Figure 14:
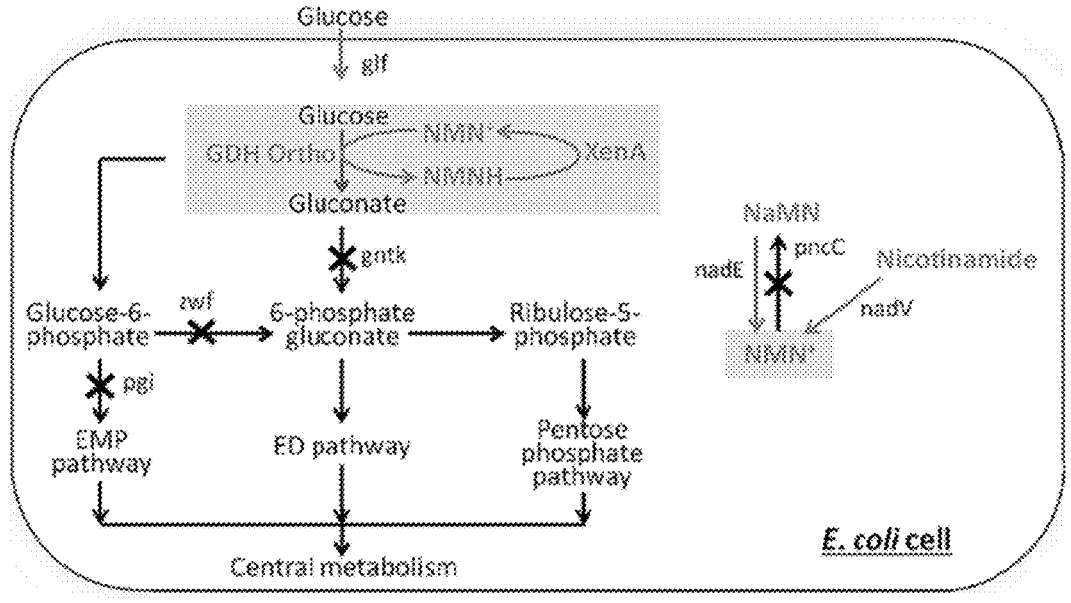
FIG. 14 shows that for the whole-cell catalyst, strain engineering limits glucose consumption and cofactor regeneration to GDH activity. Disruption of main glycolytic pathways ($\Delta$pgi, $\Delta$zwf, $\Delta$gntK) eliminated native glucose metabolism. These deletions limited cofactor reduction to only GDH activity in whole cell conversion assays in phosphate buffer. Direct transport of glucose into the cell was enabled by expression of glucose facilitator (Glf). Disruption of $NMN^+$ degrading gene ($\Delta$pncC) and overexpression of $NMN^+$ producing genes (nadE, nadV) enabled elevated intracellular levels of $NMN^+$ for GDH Ortho cycling.

Supporting *E. coli* growth with NMN⁺-dependent glycolysis. The *E. coli* strain with ΔpgiΔzwfΔgnd knockout (strain MX103, FIG. 14) cannot metabolize glucose. The strain also has ΔnadRΔpncC knockouts to potentially preserve intracellular NMN⁺. The strain was transformed with a plasmid (pSM103) containing *F. tularens* nadEV, *Z. mobilis* glf, and *R. eutropha* gntK in a synthetic operon. In addition, the strain was also transformed with one of the three plasmids: pLZ214 (XenA alone), pSM106 (GDH Ortho alone), or pLZ215 (GDH Ortho with XenA).

Colonies were picked in triplicate and grown overnight (15 h) at 30° C. in 4 mL of 2XYT media. Overnight cultures were used to inoculate (0.5%, v/v) 4 mL of expression media (2XYT, 20 g/L glucose, 1 mM nicotinamide). Cells were grown at 30° C. with shaking for 3 hours before induction with 0.5% (w/v) arabinose. Cultures were allowed to express for 3 hours at 30° C. before being harvested and washed with M9 Minimal Media (1×M9 salts, 0.1 mM CaCl₂, 1 mM MgSO₄, 1×A5 trace metals with cobalt) three times. Washed cultures were used to inoculate 4 mL of growth media to an initial $OD_{600}$ of 0.1. Growth media consisted of the previously mentioned M9 minimal media with the addition of 20 g/L glucose, 0.05% (w/v) arabinose, and 1 mM nicotinamide. Cultures were supplemented with 0 mM, 1 mM, 2 mM, or 5 mM NMN⁺ when examining the effects of extracellular NMN⁺ on growth rate. Cultures were grown while shaking at 30° C. All media contained 200 mg/L ampicillin (except overnight cultures which had 100 mg/L), 50 mg/L spectinomycin, 50 mg/L kanamycin and 0.1 mM IPTG. Cell growth was monitored by measuring optical density at 600 nm.

NMN⁺-dependent whole-cell biotransformation. One biotransformation plasmid expressing XenA, LVR, or ADH with a GDH (selected from pLZ217-pLZ225) and pSM104 containing the glucose transport facilitator were transformed into strain MX102 by electroporation. 4 mL seed cultures of 2×YT media with appropriate antibiotics, 0.1 mM IPTG, and 0.2% (wt/v) glucose were cultured at 30° C. while shaking at 250 rpm for 16 hours. 0.5% (v/v) seed cultures were used to inoculate 150 mL of 2×YT media with appropriate antibiotics, A5 trace metals with cobalt, and 0.5 mM IPTG in a 250 mL baffled shake flask and cultured at 30° C. at 250 rpm. When an $OD_{600}$~0.4 was reached, protein expression was induced with 0.1% (w/v) arabinose and cultured for an additional 8 hours at 30° C. while shaking at 250 rpm. Cells were harvested by centrifugation for 15 minutes at 20° C. at 3750 rpm. The supernatant was discarded. Nutrients from the media were removed by washing the pelleted cells 3 times with 50 mL of 100 mM potassium phosphate at pH 7.5. Cells were resuspended to an OD$_{600}$ of 100 in assay buffer consisting of 100 mM potassium phosphate buffer at pH 7.5, 200 mM D-glucose, 0.5% arabinose, and 0.5 mM IPTG. 1 mL of resuspended cells were added to 20 mL of identical assay buffer in a 250 mL unbaffled, screw-cap shake flask. KIP was spiked into the flask to 5 g/L to initiate the reaction. Flask caps were secured tightly to prevent evaporative loss of substrate or products. Flasks were incubated at 30° C. while shaking at 250 rpm for 48 hours. After 48 hours, 1 mL of culture was pelleted, and the supernatant was used for analysis. 200 μL of supernatant was extracted with an equal volume of ethyl acetate containing 200 mg/L octanol as an internal standard, and the samples were analyzed by gas chromatography. For samples expressing all three conversion enzymes (XenA, LVR, and ADH) on the same vector (pLZ226), the Bs GDH was expressed individually on a separate vector (pSM106, pSM107, or pSM108). The Zm glf gene was also expressed in the system (pSM110).

Coupled cycling conditions: All biotransformation reactions were performed in buffer A at 30° C. for 24 hours. Reaction buffer A contained 200 mM potassium phosphate buffer (pH 7.5), 1 M NaCl, 300 mM D-glucose, 6 mM NMN$^+$. Substrate ketoisophorone was added at 5 g/L. At various time points over 24 hours, 100 μL samples were taken and extracted with 100 μL ethyl acetate. Conversion was determined via GC-FID with octanol as an internal standard (see below).

BM3 assay conditions: Reaction mixtures (0.2 mL) contained 0.2 M potassium phosphate buffer (pH 7.5), 0.3 M glucose, 1 M NaCl, 2 mM NMNH with 50 μM cytochrome c (C2506 Sigma). Reactions were initiated by the addition of 0.75 mg mL$^{-1}$ purified BM3 variants and reduction of cytochrome c was monitored spectroscopically at 550 nm. Quantification was performed using extinction coefficient £$_{550}$ of 21.1 mM$^{-1}$ cm$^{-1}$. For generating NMNH, a microcentrifuge tube (2 mL) containing 35 mM Tris-HCl (pH 8.0), 4 mM NMN$^+$, 1 M NaCl and 140 mM glucose, was incubated for ~3 hr at 30° C. with purified Bs GDH I195R. An aliquot of this reaction system was taken to measure the accumulation of NMNH by reading absorbance at 340 nm. The proteins in the reaction were removed by filtering the mixture with centrifugal filter units (Amicon Ultra-0.5 Centrifugal Filter Units, Millipore, USA). The solvent was evaporated, and the residue was collected to give NMNH as a yellowish oil.

GC-FID analytical methods. All gas chromatography was performed on an Agilent 6850 (Agilent Technologies, Santa Clara, Calif., USA) equipped with a flame ionization detector (FID). An Agilent DB-WAXetr capillary column (30 m×0.56 mm×1 μm) was used for separation. Inlet and detector were held at 250° C. and 260° C., respectively. The GC was operated in constant pressure mode with a pressure of 3.66 psi. Helium was used as the carrier gas. Air and Hydrogen were supplied to the FID at 350 mL/min and 40 mL/min respectively. All gasses were purchased from Airgas (Radnor Township, Pa.). 5 μL of sample was injected with a split ratio of 2:1.

For analysis of citral and its reduction product citronellal, the oven was initially held at 150° C. for 10 minutes and then ramped at a rate of 45° C./min to 240° C. Citral and Citronellal eluted at 9.32 and 4.50 minutes, respectively. Octanol was used as an internal standard.

For analysis of trans-2-hexen-1-al and its reduction product trans-2-hexan-1-al, the oven was initially held at 50° C.

for 1 minute, the oven was ramped at 15° C./min to 120° C., then ramped at 20° C./min to 230° C., and held for 3 minutes. Trans-2-hexen-1-al and trans-2-hexan-1-al eluted at 6.41 minutes and 4.78 minutes, respectively. Octanol was used as an internal standard.

For analysis of 4-phenyl-3-butyne-2one (containing CC triple bond) and its fully reduced product 4-phenyl-2-butanone, as well as the intermediate 4-phenyl-2-butene-2-one (containing C=C double bond), the oven was initially held at 200° C. for 1 minute, then ramped at 5° C./min to 230° C., and held for 1 minute. Octanol was used for an internal standard. ketoisophorone and its reduction product levodione were analyzed using the same method. Elution times were 4-phenyl-3-butyne-2one (5.53 minutes), 4-phenyl-2-butene-2-one (6.76 minutes), 4-phenyl-2-butanone (4.55 minutes), ketoisophorone (3.65 minutes), levodione (4.08 minutes), octanol (2.80 minutes).

Computational modeling and design of Bs GDH. Glucose dehydrogenases are widely used to generate reducing power in biomanufacturing because the reaction that they catalyze is highly thermodynamically favorable and their substrate, glucose, is renewable and inexpensive. The glucose dehydrogenase from *Bacillus subtilis* (Bs GDH, UniProt ID: A0A1B2ATD9_BACIU) used for engineering in this work was chosen based on its high level of expression in *Escherichia coli* (Table 4).

TABLE 4

| Protein expression levels of GDH variants | |
| --- | --- |
| Protein Variants | Expression level (μg protein/ml culture) |
| Wild type | 67.00 |
| N92A | 81.16 |
| N92V | 57.56 |
| G94S | 117.50 |
| I195R | 108.83 |
| I195S | 96.33 |
| I195T | 105.51 |
| S17Q-P194N | 117.63 |
| L19H-I191S | No expression (<1) |
| M143S | 40.60 |
| M143T | 94.55 |
| M143G-L19G-I224R | No expression (<1) |
| I195R-Y39Q | 57.60 |
| I195R-A93K | 11.17 |
| GDH- I195R-A93K-Y39Q | 25.37 |

The design process focused on building and introducing novel interactions to the phosphate and ribose while keeping the nicotinamide ring binding and catalytic residues unaltered. Since no crystal structures of Bs GDH was available, a HMMER search was performed to identify orthologous protein structures to determine essential versus designable residues of Bs GDH. Glucose dehydrogenase from *Bacillus megaterium* (Bm GDH, PDB: 1GCO) with NAD$^+$ bound was found from this search. Pairwise sequence alignment shows that Bs GDH and Bm GDH share a pairwise sequence identity of 83.5%. The NAD$^+$ in this crystal structure forms hydrogen bonds with Thr193 and Asn196 through the amide group on the catalytically essential nicotinamide moiety. In addition, Tyr158 and Lys162 of the catalytic triad hydrogen bond with both hydroxyl groups on the ribose of the nicotinamide half of NAD$^+$ (see FIG. 2). Therefore, the equivalent residues were kept constant during all subsequent design simulations and geometric constraints enforcing the chemical interactions observed in Bm GDH were used throughout subsequent simulations to prevent the interactions critical to the enzyme's function from being changed.

Based on the Bm GDH structure, a molecular model of Bs GDH was produced using RosettaCM to obtain its three-dimensional structure and design simulations were carried out with RosettaDesign and Foldit. In the first round of design, the focus was on single point mutations predicted to create a novel interaction with the ribose-phosphate moiety and be energetically favorable.

Figure 3A:
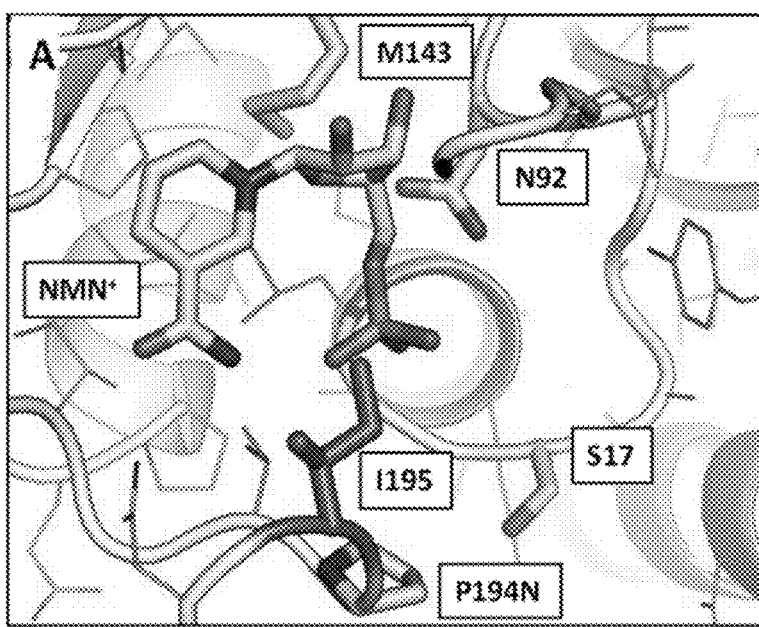
FIG. 3A-B shows the NMN$^+$ binding pocket in Bs GDH and specific activities of all solubly expressed variants. (A) The homology model of Bs GDH with nicotinamide mononucleotide (NMN$^+$) docked in the active site. The residues where mutations resulted in solubly expressed variants are shown in sticks. The mutations on position I195 (highlighted in red) resulted in three variants with improved activity. (B) A log scale bar chart showing variants specific activities towards NMN$^+$. Activities were measured by monitoring the increase in absorbance corresponding to the reduction of NMN$^+$ to NMNH. The error bars represent one standard deviation above the mean of triplicate experiments.
Figure 3B:
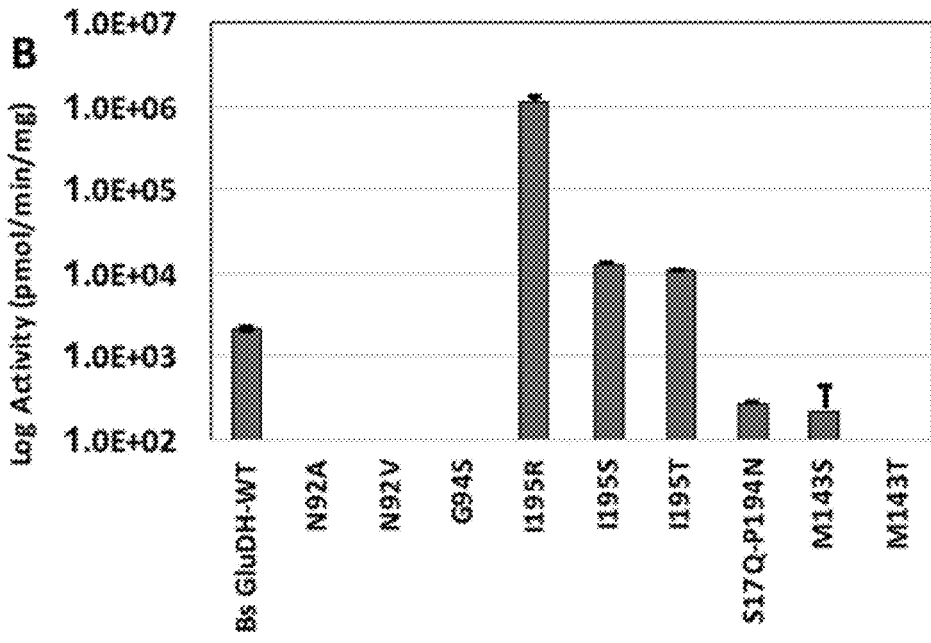

Characterization of Bs GDH variants. From the first round of design, a total of 11 variants were constructed, expressed, and kinetically characterized. 9 of the 11 variants were solubly expressed with 5 having measurable activities (see FIG. 3, and Table 5). Three variants displayed improvement in activity towards $NMN^+$, which all contained a polar amino acid substitution of I195 (see FIG. 3). The best variant from this set, I195R, improves the specific activity of Bs GDH by 545-fold towards $NMN^+$. This arginine residue is predicted to improve the electrostatic complementarity between the binding pocket and $NMN^+$ by making two new interactions with the negatively charged phosphate on the $NMN^+$ ligand (see FIG. 3A). Protein sequence conservation analysis of Bs GDH against its enzyme family (Pfam ID: PF13561.5) reveals that the position I195 is highly variable where all 20 amino acids are present at varying frequencies (Table 5).

TABLE 5

| Sequence conservation analysis of I195 in its protein family PF13561.5. | | |
|---|---|---|
| | Frequency | Percent of representation |
| A | 110 | 2.50% |
| C | 2 | 0.00% |
| D | 33 | 0.70% |
| E | 31 | 0.70% |
| F | 461 | 10.40% |
| G | 112 | 2.50% |
| H | 10 | 0.20% |
| I | 371 | 8.40% |
| K | 20 | 0.50% |
| L | 899 | 20.30% |
| M | 1,768 | 39.90% |
| N | 42 | 0.90% |
| P | 21 | 0.50% |
| Q | 97 | 2.20% |
| R | 65 | 1.50% |
| S | 67 | 1.50% |
| T | 210 | 4.70% |
| V | 45 | 1.00% |
| W | 52 | 1.20% |
| Y | 15 | 0.30% |

This result showed that all 20 amino acids are represented at this position with methionine and leucine accounting for more than 50% of all occurrences at this position in the family.

Of the 4,753 sequences analyzed, arginine and isoleucine occurred in 1.5% and 8.5% of the sequences respectively, with methionine having the highest occurrence of 39.9%. This suggests I195 is a position with high plasticity and tolerance to mutational changes, primed for tuning the coenzyme binding functionality.

Figure 4A:
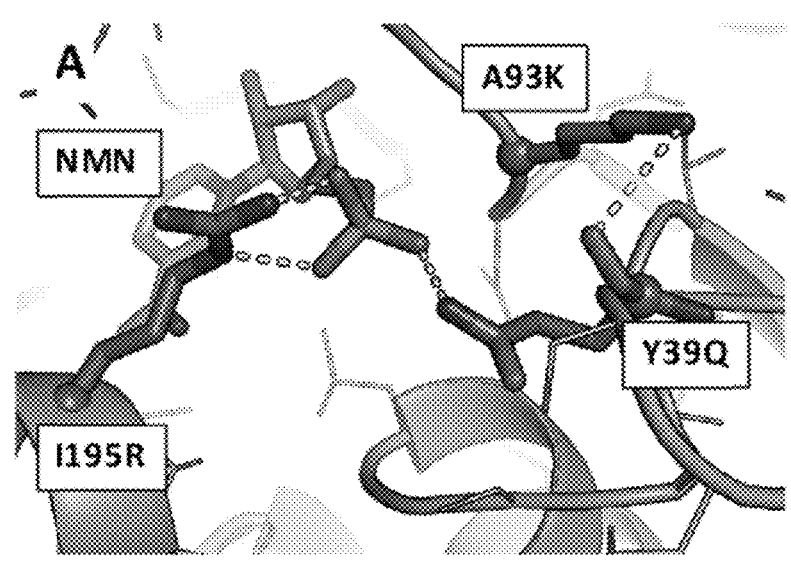
FIG. 4A-B provides for probing the role and contribution of each amino acid in the best triple mutant. (A) The model of Bs GDH triple mutant (I195R-A93K-Y39Q) with NMN$^+$ docked in the active site. The mutation I195R and Y39Q are predicted to form hydrogen bonds with the phosphate on NMN$^+$. A93K is predicted to facilitate and support the loop of Y39Q to be in the proper conformation to interact with NMN$^+$. (B) A log scale bar chart showing individual mutations' contribution to the increased NMN$^+$-dependent activity of GDH Triple. The error bars represent one standard deviation above the mean of triplicate experiments.

Using I195R as the starting chassis, a second round of design was carried out to further improve the enzyme's activity towards $NMN^+$. From this round of design simulation, A93K was predicted to form a new hydrogen bond with the backbone carbonyl oxygen of residue Y39 (see FIG. 4A). This new interaction was predicted to stabilize a backbone geometry that brings Y39 within 6 Å of the phosphate on $NMN^+$, opening new possibilities for engineering (See FIG. 4A). Amino acids that could potentially form hydrogen bonds with $NMN^+$ (Q, N, R, K, and H) at Y39 were systematically introduced with their Rosetta energies evaluated. These simulations predicted that Y39Q could form a new hydrogen bond with the phosphate of $NMN^+$ (see FIG. 4A).

Figure 4B:
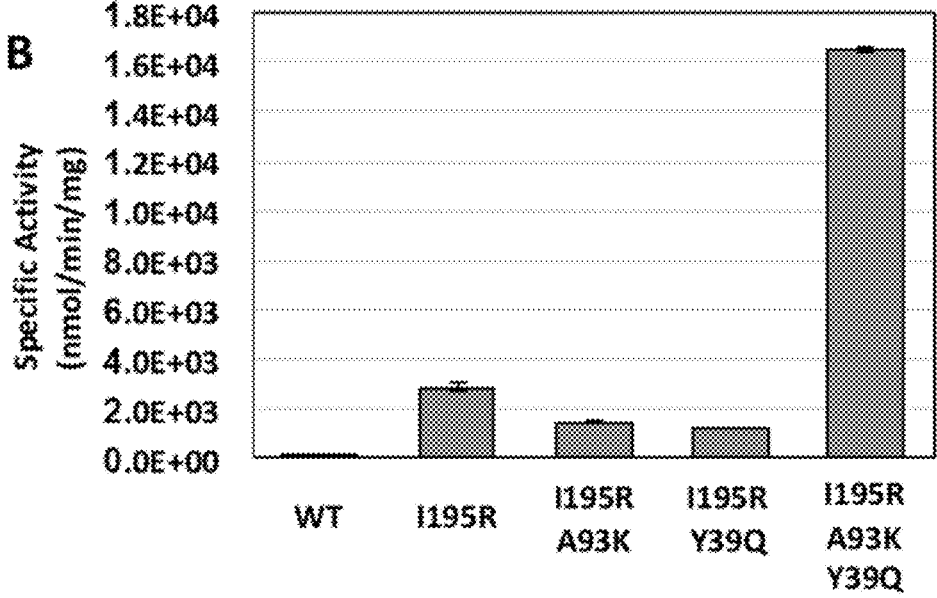

Based on the model of this variant, the Cα atom of Y39 are within 6 Å of the phosphate on $NMN^+$ when A93K is present, compared to it being more than 8 Å away without A93K. Further design simulations on I195R-A93K predicted that Y39Q could form a new hydrogen bond with the phosphate of $NMN^+$ (see FIG. 4A). Kinetic characterization of I195R-A93K-Y39Q reveals that it has a 4-fold improvement in catalytic efficiency over I195R alone (see Table 6). This final triple mutant exhibits a $k_{cat}/K_M$ of ~0.51 mM$^{-1}$ s$^{-1}$, which corresponds to a 1,000-fold increase in catalytic efficiency over the wild-type enzyme towards $NMN^+$. Furthermore, the mutations A93K and Y39Q occupy the predicted binding pocket for the adenosine half of the $NAD^+$ molecule, which potentially excludes the natural redox cofactors $NAD(P)^+$ and improves this enzyme's specificity towards $NMN^+$ (see FIG. 4A). The strength of computational design is highlighted in the discovery of the three mutations which function with high cooperativity (see FIG. 4B). First, the lack of impact on activity by mutations A93K, Y39Q, and A93K-Y39Q towards $NMN^+$ suggested that I195R is needed to anchor $NMN^+$ in a productive binding mode. Second, I195R-Y39Q and I195R-A93K exhibit 14-fold and 9-fold lower activity than GDH Triple, respectively, suggesting that A93K and Y39Q must be simultaneously present for the new predicted hydrogen bond between Y39Q and the phosphate of $NMN^+$ to form. Kinetic characterization reveals that the catalytic efficiencies of the triple mutant on $NAD^+$ and $NADP^+$ decrease by 38-fold and 1,600-fold respectively, representing an overall specificity switch of 38,000-fold and 1,600,000-fold towards $NMN^+$ (see Table 6).

TABLE 6

| Kinetic parameters of wild type and GDH variants | | | | |
|---|---|---|---|---|
| Enzymes | Cofactor | $K_M$ (mM) | $K_{cat}$ (s$^{-1}$) | $k_{cat}/K_M$ (mM$^{-1}$ s$^{-1}$) |
| WT | $NAD^+$ | 0.03 ± 0.0006 | 5.5 ± 1.1 | 180 ± 34 |
| | $NADP^+$ | 0.015 ± 0.0002 | 4.3 ± 0.0051 | 280 ± 3.1 |
| | $NMN^+$ | n.d ± n.d | n.d ± n.d | 0.0005 ± 0.00005 |
| I195R | $NAD^+$ | 0.053 ± 0.0092 | 7.3 ± 1.1 | 137 ± 2.6 |
| | $NADP^+$ | 0.016 ± 0.0008 | 2.5 ± 0.21 | 156 ± 5.5 |
| | $NMN^+$ | 8.9 ± 0.69 | 1.1 ± 0.27 | 0.12 ± 0.021 |

TABLE 6-continued

| | | | | $k_{cat}/K_M$ |
|---|---|---|---|---|
| Enzymes | Cofactor | $K_M$ (mM) | $K_{cat}$ (s$^{-1}$) | (mM$^{-1}$ s$^{-1}$) |
| I195R-A93K-Y39Q | NAD$^+$ | 3.7 ± 0.93 | 0.41 ± 0.026 | 0.11 ± 0.021 |
| (GDH Triple) | NADP$^+$ | 0.61 ± 0.15 | 4.4 ± 0.034 | 7.5 ± 1.8 |
| | NMN$^+$ | 6.1 ± 0.83 | 3.1 ± 0.037 | 0.51 ± 0.063 |
| I195R-A93K- | NAD$^+$ | 6.5 ± 1.3 | 0.025 ± 0.002 | 0.0038 ± 0.0005 |
| Y39Q-S17E | NADP$^+$ | 2.0 ± 0.008 | 0.022 ± 0.013 | 0.011 ± 0.008 |
| (GDH Ortho) | NMN$^+$ | 5.9 ± 1.0 | 1.21 ± 0.09 | 0.21 ± 0.02 |

*Kinetic parameters of wild type and GDH variants*

To further probe the contribution of A93K mutation towards the triple mutant I195R-A93K-Y39Q, the double mutants I195R-A93K and I195R-Y39Q were constructed and characterized. Specific activity measurements of these variants reveal that I195R-Y39Q is 14-fold slower than I195R-A93K-Y39Q and 2.4-fold slower than I195R (see FIG. 4B). This is consistent with the model on the triple mutant's dependence on A93K to support the predicted loop conformation which allows Y39Q to form new hydrogen bond with the phosphate on NMN$^+$.

Figure 5:
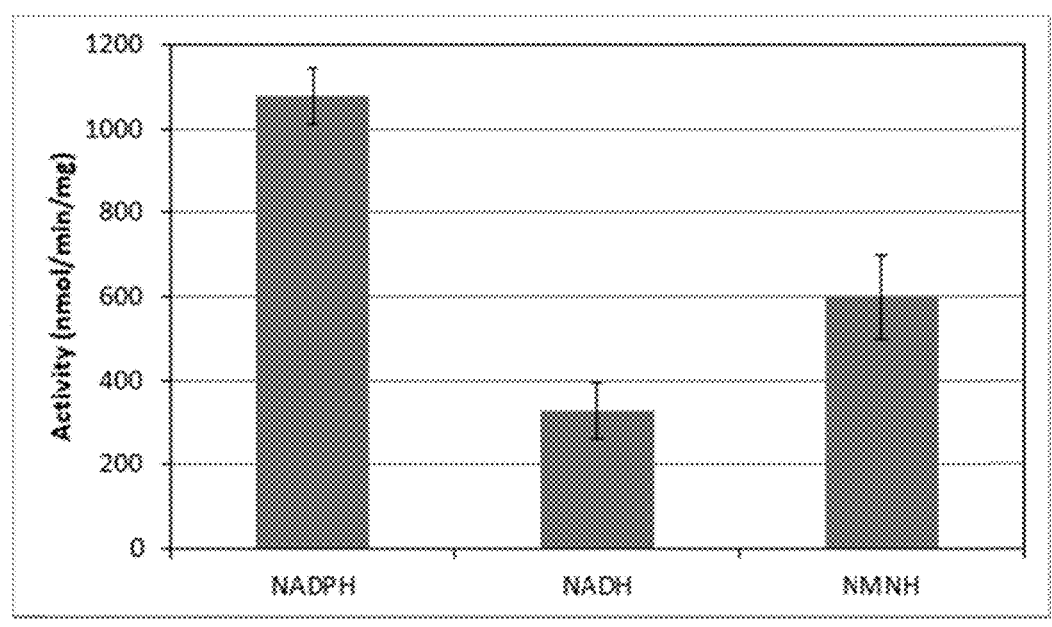
FIG. 5 demonstrates XenA activity with different cofactors. Using ketoisophorone as the substrate, the activity of purified *Pseudomonas putida* XenA wild type was tested, using NADPH, NADH, or NMNH as the reducing cofactor. The error bars represent the standard deviations of three replicates. These results showed that XenA accepts NMNH as the redox cofactor with comparable activity to the natural cofactors NADPH and NADH.
Figure 6:
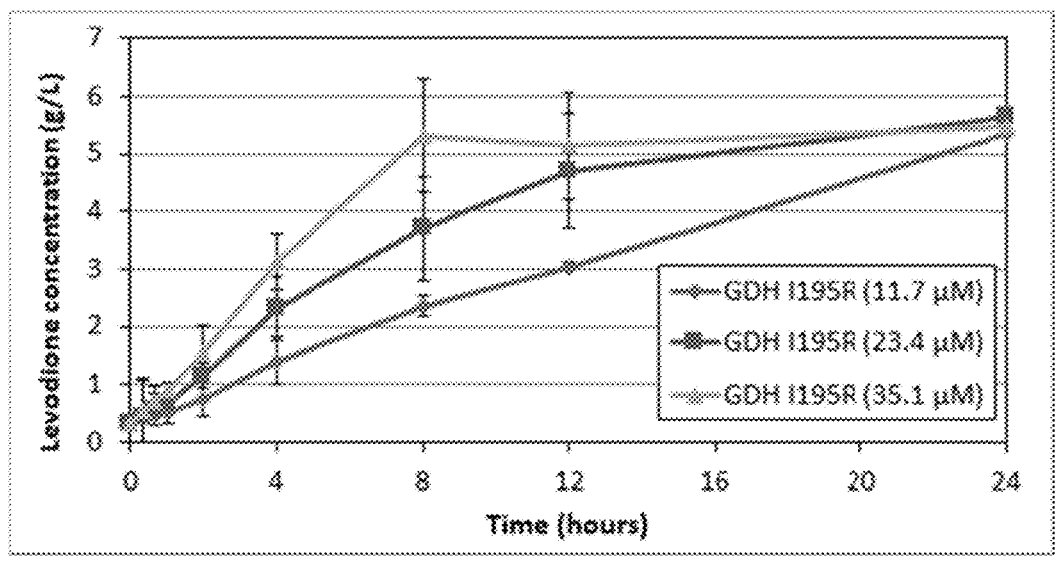
FIG. 6 presents NMN(H)-cycling biotransformation of ketoisophorone to levodione with different GDH loading. GDH I195R was used to generate NMNH in situ, which was utilized by XenA to reduce ketoisophorone to levodione. While the XenA concentration was held at a constant level of 0.75 mg mL$^{-1}$, three different enzyme loadings of GDH I195R at 11.7, 23.4, and 35.1 µM were used, respectively. The error bars represent the standard deviations of three replicates. The results suggested that with 11.7 µM GDH loading, XenA was in excess and the initial production rate was limited by GDH activity.
Figure 7A:
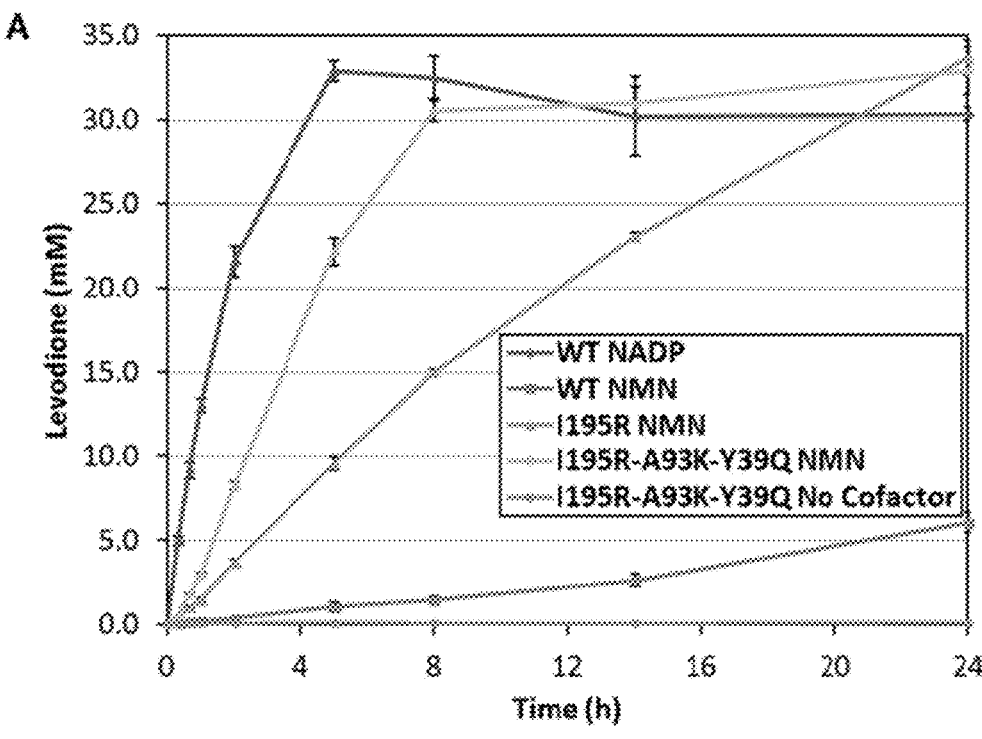
FIG. 7A-B provides for the biotransformation of ketoisophoren (KIP) into levodione supported by NMN(H) cycling. (A) Engineered Bs GDH I195R and I195R-A93K-Y39Q, in combination of *Pseudomonas putida* XenA, supported NMN(H)-dependent levodione generated from KIP. (B) Bs GDH I195R-A93K-Y39Q was stable for at least 96 hours, as suggested by the steadily increasing of levodione and decreasing of KIP over 96 hours.
Figure 7B:
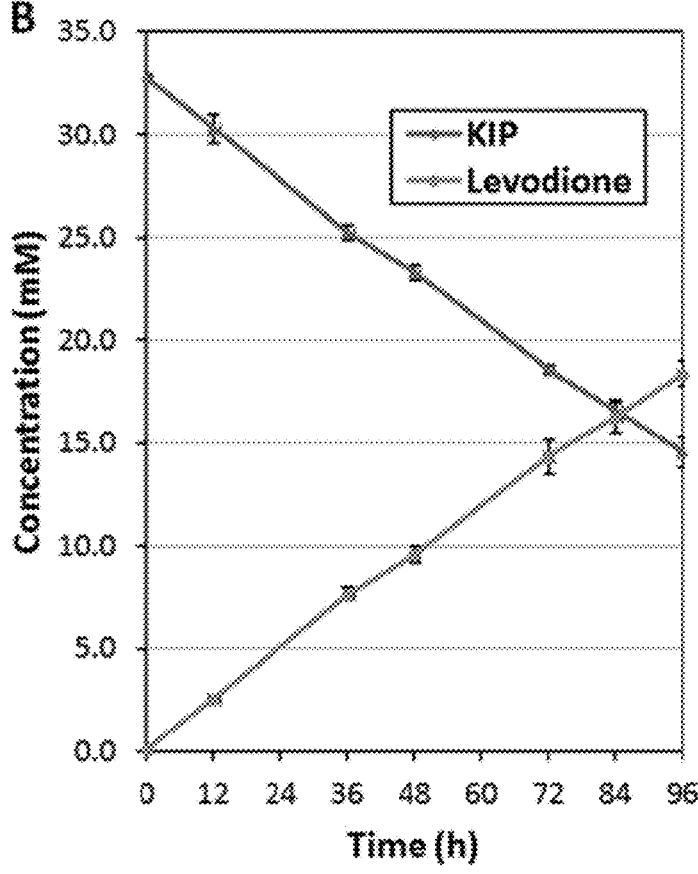

Efficient NMN(H) cycling in enzymatic biotransformation. Whether the unnatural cofactor NMN$^+$ and the engineered Bs GDH could efficiently sustain enzymatic biotransformation processes was next determined. Previous studies using enoate reductases revealed true opportunities for industrial utilization of unnatural cofactors at preparative scale. The model reaction of the asymmetric reduction of the activated C=C double bond in ketoisopherone (KIP) catalyzed by the enoate reductase XenA from *Pseudomonas putida*, producing the chiral compound levodione was chosen. XenA has been shown to be promiscuous for a range of unnatural redox cofactors. Using kinetic assays, it was first shown that NMNH was also well accepted by XenA with comparable activity to the natural cofactors NADH and NADPH (see FIG. 5). Subsequently, KIP biotransformation was performed using Bs GDH variants to generate NMNH in situ (see FIG. 7). With XenA in excess, the initial production rate of levodione correlated to the activity of the cofactor recycling enzymes (see FIG. 6). When using 6 mM NADP$^+$ as the cycling cofactor, the wild type Bs GDH supported an initial productivity of ~3.00 μM s$^{-1}$ (see FIG. 7A). However, when NMN$^+$ was used in place of NADP$^+$, the initial productivity dropped to ~0.05 μM s$^{-1}$. Importantly, the engineered Bs GDH variants I195R and I195R-A93K-Y39Q improved the NMN$^+$-dependent productivity by 10- and 22-fold, reaching ~0.51 and ~1.15 μM s$^{-1}$, respectively. Given an enzyme loading of Bs GDH at 11.7 μM, the initial turnover frequency of the triple mutant reached ~0.10 s$^{-1}$, which is within the range of what is required for industrial catalysts. The NMN(H)-based biotransformation process mediated by engineered Bs GDHs achieved >99% conversion of 33 mM KIP (1a, FIG. 8) to levodione (1b, FIG. 8) in 24 hours. With no redox cofactors added, the system showed virtually no conversion, which ruled out the possibility that the observed conversion in NMN(H) cycling reaction was conferred by the NAD(P)$^+$ contamination in recombinant proteins.

The stability of an enzymatic catalyst is critical for its practicality. Using a lower Bs GDH enzyme loading of 0.47 μM, longer-term KIP biotransformation was performed. The results showed that Bs GDH I195R-A93K-Y39Q sustained robust conversion over 96 hours (see FIG. 7B). The TTN number of the engineered variant was calculated to be 39,000, which is substantially higher than those of previously reported unnatural cofactor recycling methods involving an artificial metalloenzyme (TTN ~2000) and engineered Ss GDH (TTN ~1183).

XenA is active towards a broad range of substrates containing activated C=C double bonds. Coupled XenA-Bs GDH I195R-A93K-Y39Q system also achieved ~76% conversion of 10 mM citral (2a, FIG. 8) or ~49% conversion of 50 mM trans-2-hexen-1-al (3a, FIG. 8) in 24 hours, using NMN$^+$ as the cycling cofactor.

In vitro NMN(H) cycling supports diverse chemistries. XenA's promiscuity for artificial redox cofactors may be attributed to their ping-pong mechanism of catalysis involving the flavin prosthetic groups. Specifically, the hydride transfer from cofactors to flavin might be less sensitive to the differences in binding modes of various cofactors. Indeed, several other classes of flavoenzymes have been shown to accept unnatural redox cofactors. Given the versatility of flavoenzymes, there might be opportunities to extend the application of the NMN(H) cycling systems to other chemistries.

Figure 8:
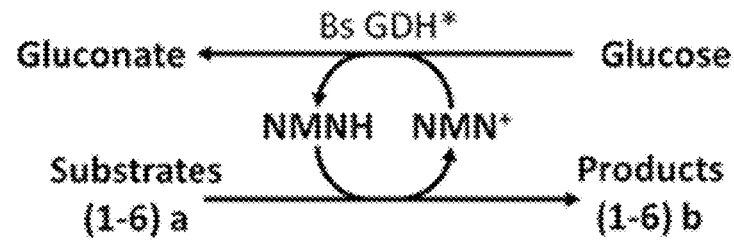
FIG. 8 provides a table demonstrating that the engineered polypeptides supported diverse chemistries by recycling NMN$^+$ to NMN(H).
Figure 9:
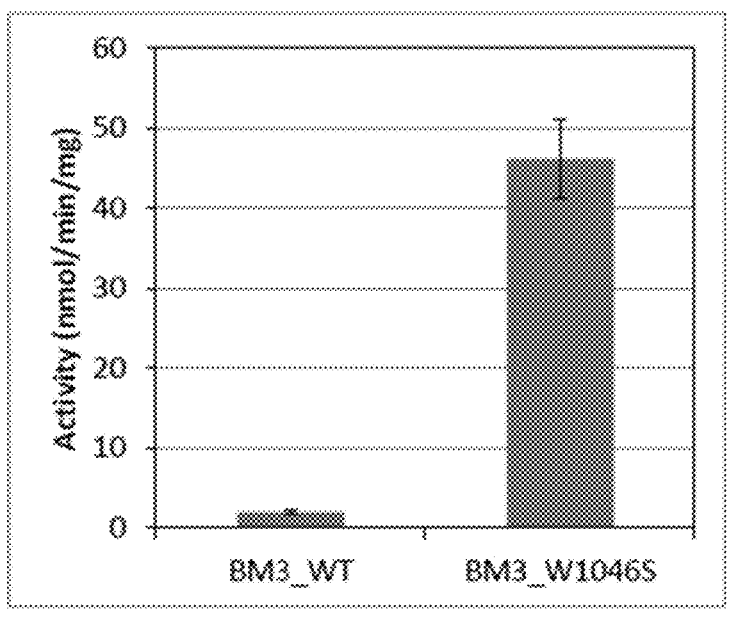
FIG. 9 demonstrates engineering P450 BM3 in order to improve the NMNH-dependent activity. Using cytochrome c as the substrate, the NMNH-dependent activity of P450 BM3 wild type and W1046S was measured using purified proteins. The error bars represent the standard deviations of three replicates. The results showed that W1046S mutation enhanced the NMNH-dependent activity by around 46-fold compared to wild type.

The NMN(H) cycling process was coupled with three enzymes other than XenA (FIG. 8). In the presence of Bs GDH I195R-A93K-Y39Q and NMN$^+$, the enoate reductase OYE3 from *Saccharomyces cerevisiae* reduced the activated C≡C triple bond in 4-phenyl-3-butyne-2-one (4a, FIG. 8) with >99% conversion; and the nitro reductase NfsB from *Escherichia coli* reduced the nitro group in nitrofurazone (5a, FIG. 8) with ~92% conversion. The cytochrome P450 enzyme BM3 from *Bacillus megaterium* natively has low activity with NMNH as the electron donor. By mutating the highly conserved "shielding" tryptophan at the cofactor binding site to serine, the NMNH-dependent activity of BM3 was improved by ~46 fold (see FIG. 9). Subsequently, it was shown that Bs GDH I195R-A93K-Y39Q generated NMNH in situ to supply electrons to the engineered BM3 W1046S, allowing the latter to reduce cytochrome c with >99% conversion (see FIG. 8).

Engineering Bs GDH to exclude NAD(P)$^+$. To achieve orthogonality in vivo, the Bs GDH enzyme must be selective towards NMN$^+$ over NAD$^+$ and NADP$^+$. Kinetic characterization reveals that the catalytic efficiencies of GDH Triple on NAD$^+$ and NADP$^+$ decreased by 1,600-fold and 38-fold respectively, representing an overall specificity switch of 1,600,000-fold and 38,000-fold towards NMN$^+$ (Table 6). However, GDH Triple still prefers NADP$^+$ over NMN$^+$. Therefore, additional mutations that could further disrupt the binding of NAD$^+$ and NADP$^+$ without significant effects on NMN$^+$ were explored. Specifically, negatively charged mutations that exploited the differential electrostatic repulsion of phosphates between NMN$^+$ and NAD(P)$^+$ were evaluated through docking simulations using Rosetta.

Figure 10A:
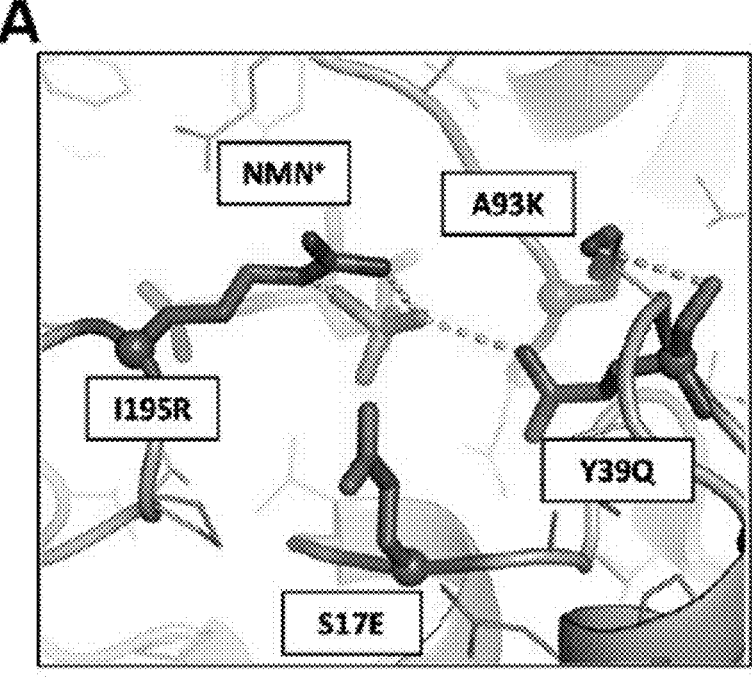
FIG. 10A-C shows engineering of Bs GDH in order to exclude NAD(P)$^+$. Comparison of the predicted binding sites of GDH Ortho (I195R-A93K-Y39Q-S17E) with NMN$^+$(A) and with NAD$^+$(B). GDH Ortho binds NMN$^+$ in a similar binding mode as observed in GDH Triple. In contrast, when NAD$^+$ was docked into this quadruple mutant, S17E repulses the diphosphate on NAD$^+$ and leads it to a binding mode where the beneficial interactions with I195R and Y39Q are disrupted. (C) The predicted conformational changes of NAD$^+$ bound in the wild-type GDH (wt), GDH Triple (I195R-A93K-Y39Q) and GDH Ortho (I195R-A93K-Y39Q-S17E). The introduced mutations in GDH Triple and GDH Ortho move the NAD$^+$ from its native binding mode towards solvents through occluding the AMP moiety. This causes the "recognition handle" to be no longer available for the enzyme, which switches the specify towards NMN$^+$ instead.
Figure 10B:
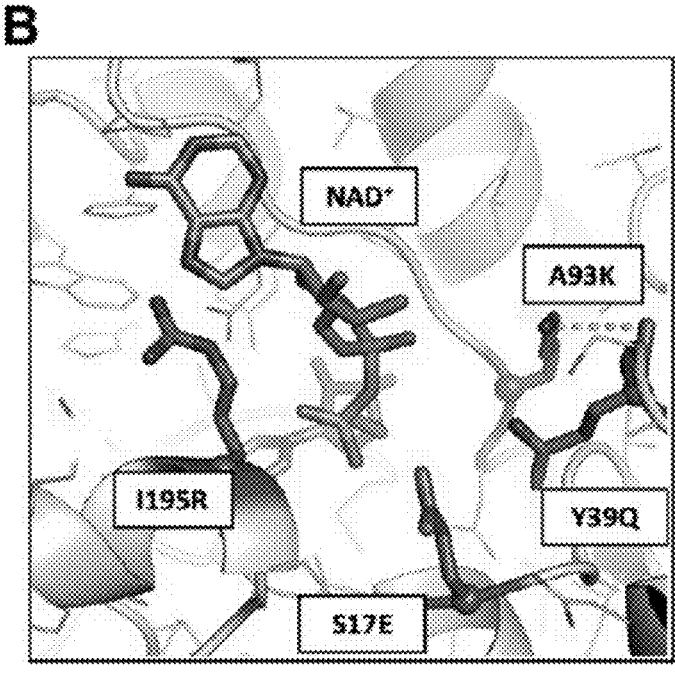
Figure 10C:
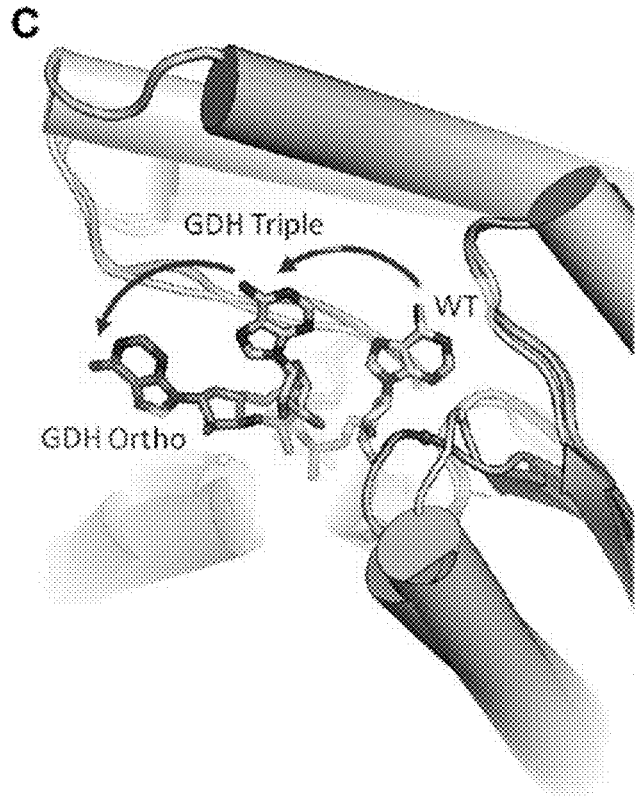

Significant differences in binding modes of these ligands were observed upon the introduction of S17E (see FIG. 10). The predicted binding mode of NMN$^+$ with the quadruple mutant I195R-A93K-Y39Q-517E (GDH Ortho) remains similar to that of the GDH Triple with the hydrogen bonds between I195R and NMN$^+$ stayed unaltered (see FIGS. 10A and 4A). On the other hand, due to electrostatic repulsion and steric hindrance, S17E is predicted to repel NAD$^+$ into a binding mode that disrupts all favorable interactions with I195R and Y39Q (see FIG. 10B). More importantly, the S17E mutation is predicated to force the AMP moiety of NAD$^+$ to further bend outward towards solvents (see FIG. 10C), making this "recognition handle" no longer available for the enzyme.

These predictions are supported by the catalytic efficiencies observed. While there was only a modest reduction in NMN$^+$-dependent catalytic efficiency for GDH Ortho compared with GDH Triple, the catalytic efficiencies dropped 220- and 890-fold for NAD$^+$ and NADP$^+$ upon introducing the S17E mutation (Table 6). Compared to the wild type, GDH Ortho has an overall specificity switch of ~2×10$^7$- and ~1×10$^7$-fold towards NMN$^+$ from NAD$^+$ and NADP$^+$, respectively. The K$_M$ of GDH Ortho for NAD$^+$ (6.5 mM) and NADP$^+$ (2.0 mM) is much higher than these natural cofactors' intracellular concentrations in *E. coli*. These results suggest GDH Ortho's potential as a viable orthogonal catalyst in vivo.

In vivo NMN(H) cycling supports *E. coli* growth. To investigate GDH Ortho's NMN$^+$ cycling function in vivo, it was sought to link its activity to cell growth and use the latter as an easy readout. First, the Embden-Meyerhof-Parnas (EMP pathway) and the pentose phosphate pathway (PPP) were disrupted by knocking out zwf, gnd, and pgi genes (see FIG. 11A). This resulted in a strain that cannot grow with glucose as the sole carbon source. Next, the entry way of glucose to the Entner-Doudoroff pathway (ED pathway) was facilitated by over-expressing the genes encoding glucose facilitator (glf from *Zymomonas mobilis*), gluconate kinase (gntK from *Ralstonia eutropha*), and wild-type or engineered Bs GDH (see FIG. 11A). In this system, cell growth on glucose is specifically linked to the function of GDH because the conversion of glucose to gluconate is the only entry to the single glycolytic pathway available, the ED pathway.

Although NMN$^+$ is naturally produced by DNA ligases in *E. coli* in a small amount, it was hypothesized that this low level may not be sufficient to support effective redox cycling. To build up the intracellular NMN$^+$ pool, the genes encoding nicotinamide phosphoribosyl transferase (nadV) and NMN synthetase (nadE) from *Francisella* tularensi were overexpressed in the above-mentioned strain (see FIG. 11A). Furthermore, potential NMN$^+$-degradation pathways in *E. coli* were disrupted by knocking out genes pncC and nadR (see FIG. 11A). These manipulations together resulted in a ~1000-fold increase in intracellular NMN$^+$ concentration compared to that of wild type *E. coli* (from ~1 µM to ~1077 µM, see FIG. 11B). In the highest NMN$^+$-producing strain, the level of the NMN$^+$ reached around 30% that of NAD$^+$ (see FIG. 11C).

Figure 11A:
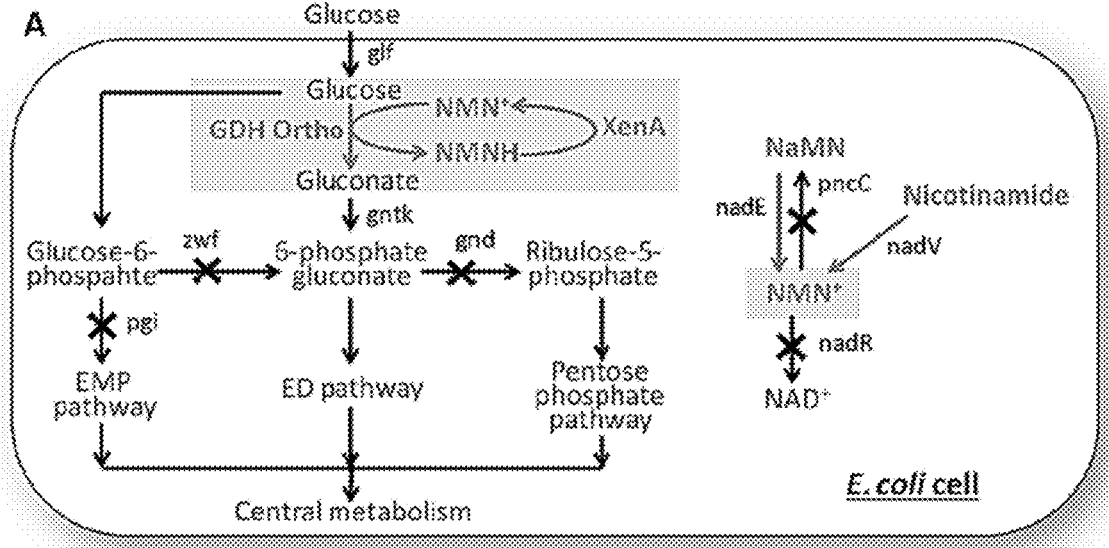
FIG. 11A-E demonstrates in vivo NMN$^+$ cycling supports *E. coli* growth. (A) An engineered Entner-Doudoroff pathway (ED pathway) which couples GDH activity to *E. coli* growth on glucose. (B) Disruption of NMN$^+$ degrading genes (pncC and nadR) and overexpression of NMN$^+$ producing genes (Ft nadE and Ft nadV) enabled elevated intracellular levels of NMN$^+$. (C) Intracellular levels of NAD$^+$ were slightly lowered in the ΔpncC and ΔnadR cells. (D) Using the synthetic pathway to supply NMN$^+$ intracellularly, GDH Ortho supported *E. coli* growth on glucose when XenA was present to cycle NMNH. (E) Addition of 5 mM NMN$^+$ extracellularly supported higher cell growth when both GDH Ortho and XenA were present. The error bars represent one standard deviation above the mean of triplicate experiments. XenA, enoate reductase from *Pseudomonas putida*. Ft, *Francisella tularensi*.
Figure 11B:
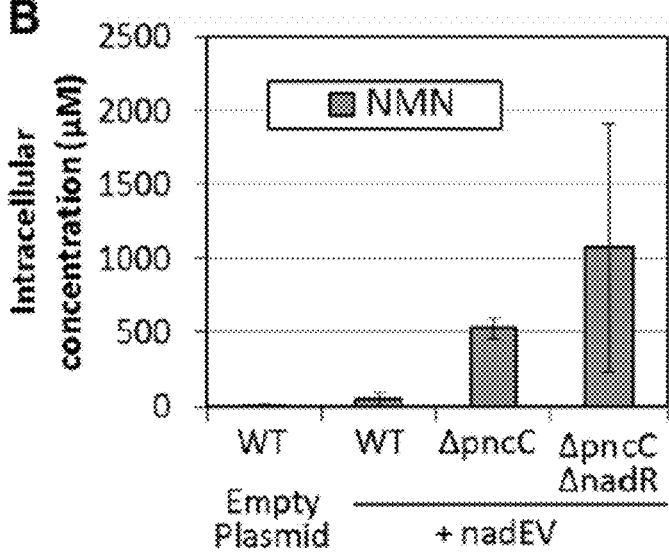
Figure 11C:
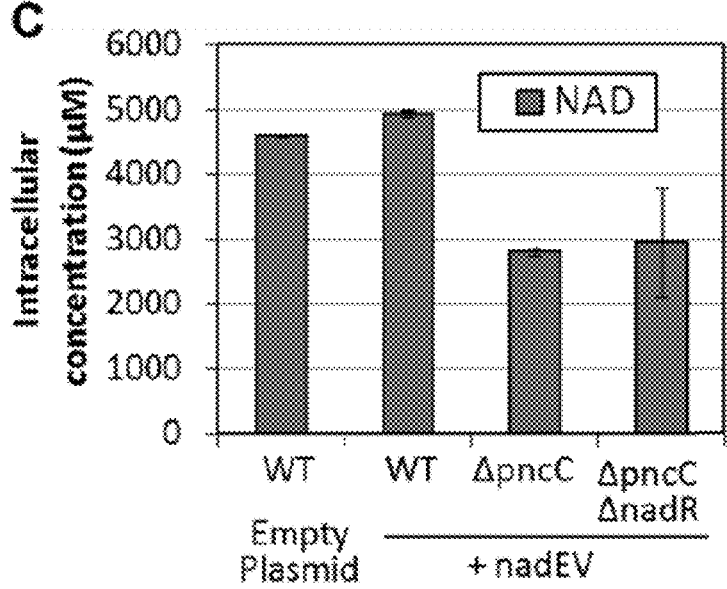
Figure 11D:
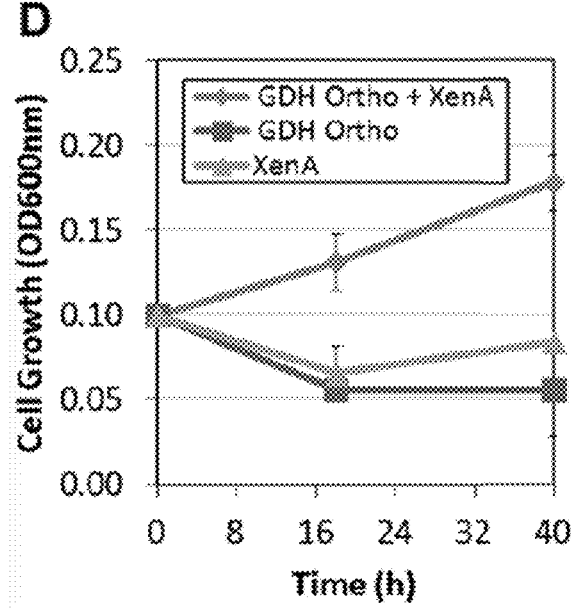
Figure 11E:
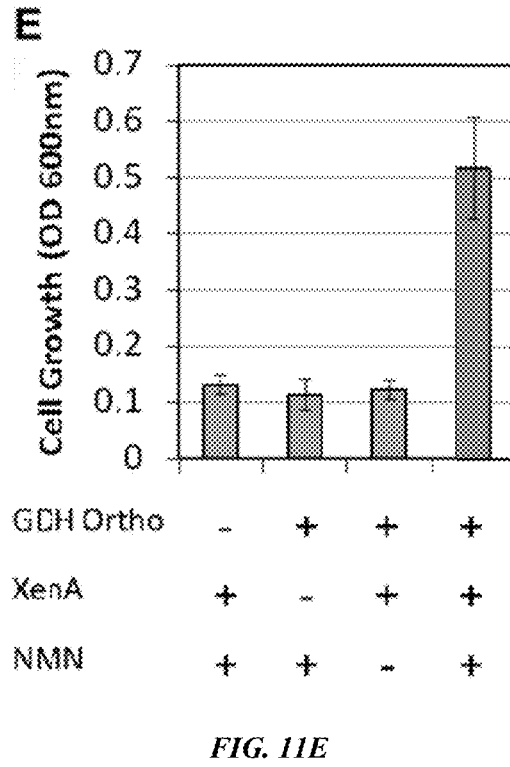
Figure 12A:
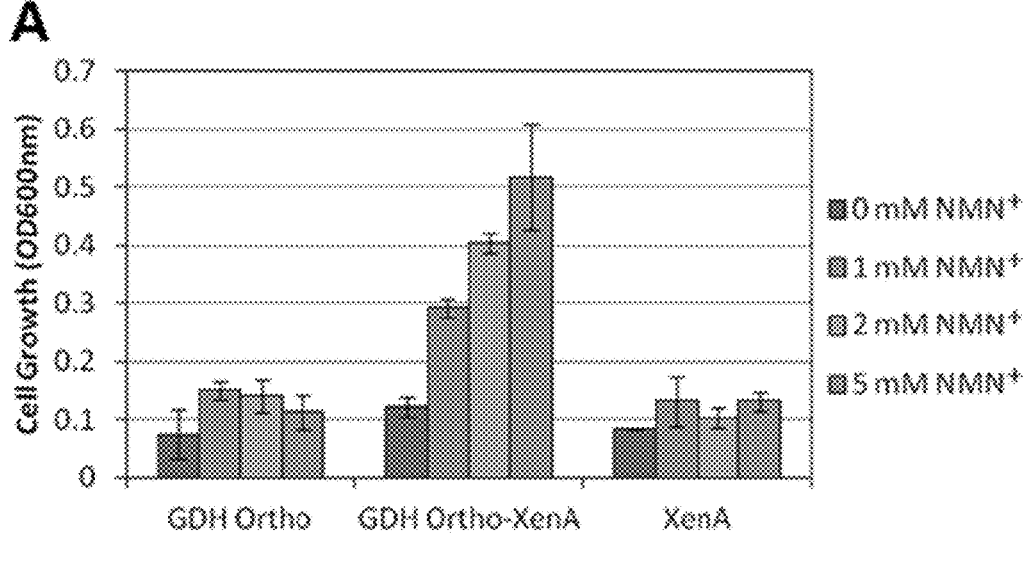
FIG. 12A-B shows the dependence of growth on the concentration of NMN$^+$. (A) Increased supplementation of NMN$^+$ supports faster growth via increased GDH Ortho cycling with XenA (NMNH-redox cycling partner). In the strain used (Strain MX103), cell growth was directly tied to GDH activity in minimal glucose media and cofactor regeneration via XenA activity. Metabolism of glucose was limited to the Entner-Doudoroff (ED) pathway in this strain (Δpgi, Δzwf, Δgnd). Therefore, entry to glycolysis for glucose was dependent on GDH Ortho conversion of glucose to gluconate, which was then converted to gluconate-6-phosphate via gntK (*Ralstonia eutropha* gntK was overexpressed to facilitate. (B) Expression of GDH wt enabled robust growth in the single glycolytic pathway (ED pathway) engineered strain MX103 in minimal glucose media. Native cell metabolism was able to supply GDH wt (red) with NAD(P)$^+$ to support glucose to gluconate cycling without additional cofactor supplementation or a heterologous redox cycling partner. Without expression of GDH (blue), this strain did not demonstrate glucose metabolism. The error bars represent one standard deviation above the mean of triplicate experiments.
Figure 12B:
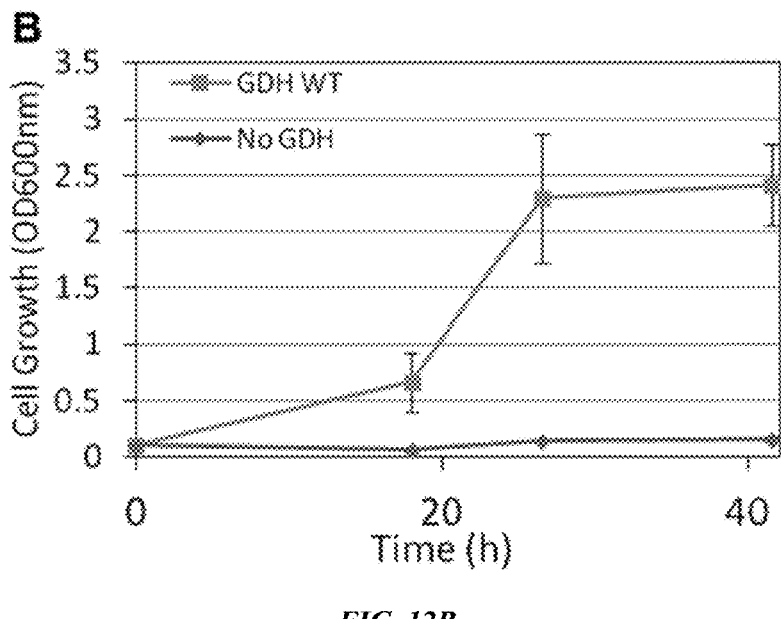
Figure 13A:
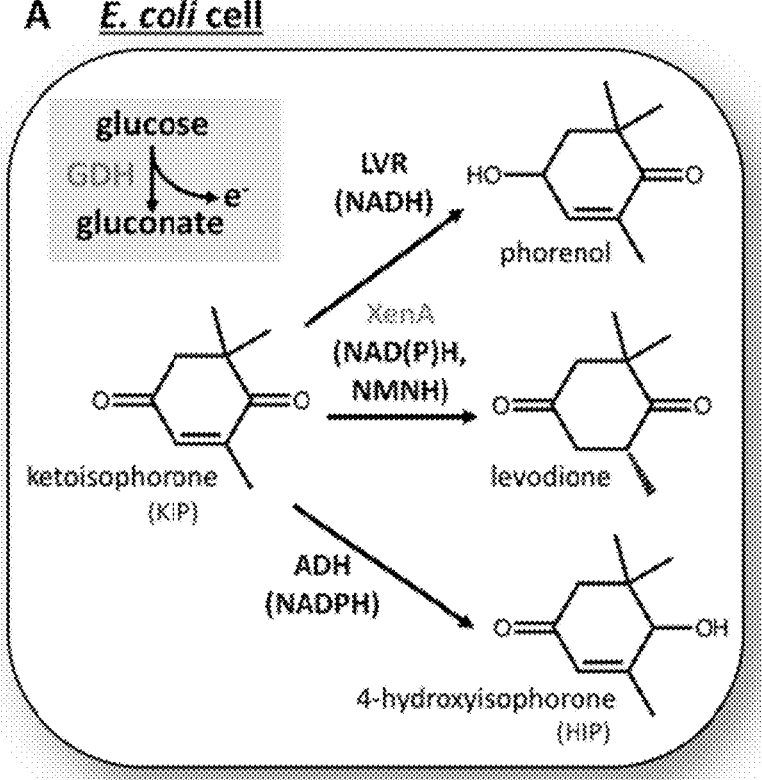
Figure 13D:
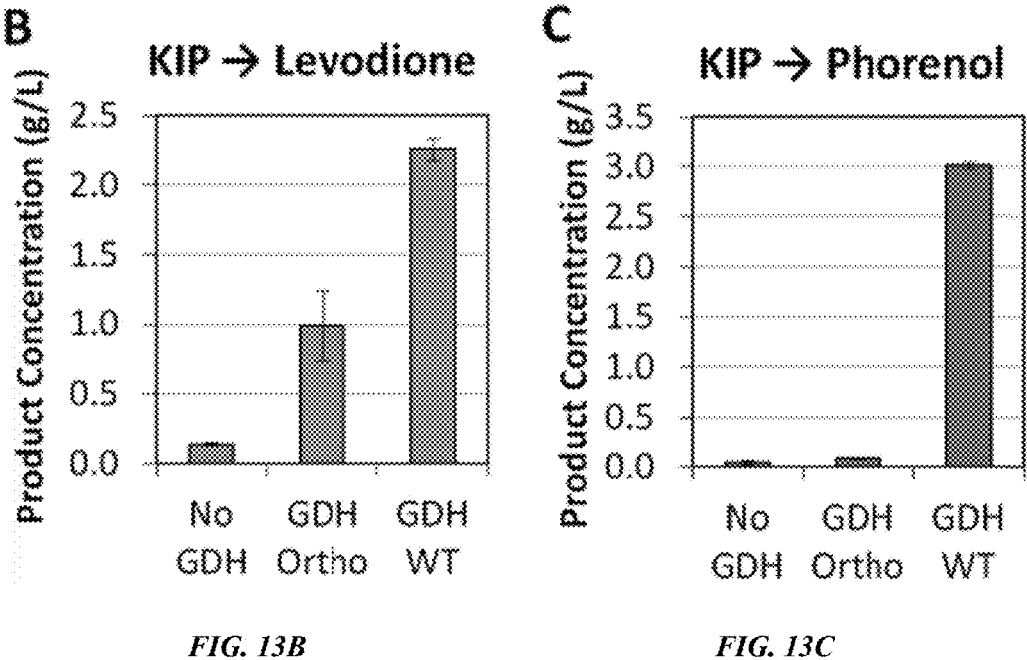
Figure 13D:
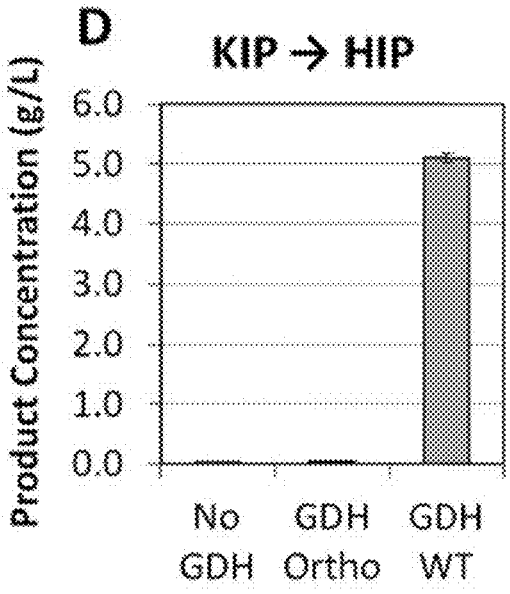
Figure 13E:
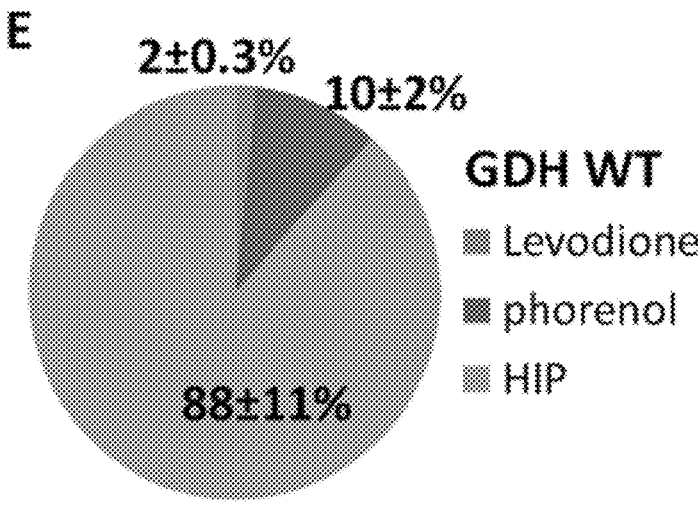
Figure 13F:
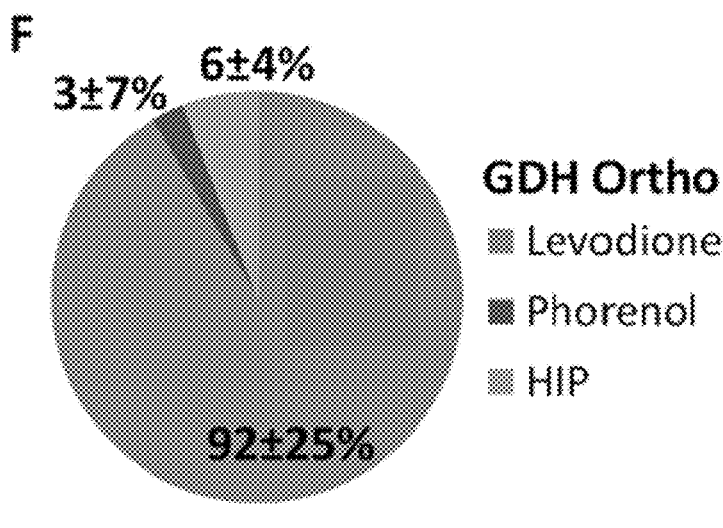

Subsequently, the NMN(H)-cycling enzymes were introduced (see FIGS. 11A and 11D). In minimal medium with glucose as the sole carbon source, only the cells harboring both GDH Ortho and XenA were able to grow, suggesting that these two enzymes form a closed redox cycle in vivo which sustained the engineered glycolic pathway. Consistently, cells with only one half of the redox pair did not grow (see FIG. 11D). Overall, these results support that the unnatural redox cofactor NMN$^+$ cycles in vivo, which can provide sufficiently high flux to support the life-essential, central carbon metabolism. Moreover, NMNH generated by GDH Ortho is an orthogonal reducing power in *E. coli* because native enzymes in the host could not consume NMNH efficiently enough to replace the need for a heterologous, NMNH-consuming enzyme (e.g., XenA). Although the built-in NMN$^+$ pool could support effective redox cycling, it was found that supplementing NMN$^+$ in the medium afforded an increased growth rate (see FIG. 11E and FIG. 12). Again, cells with all three components of the redox cycle (GDH Ortho, XenA, and NMN$^+$ supplementation) reached a much higher cell density than those with any one of the three components omitted (see FIG. 11E). The dependence of growth on NMN$^+$ concentration indicates that GDH Ortho operates with this unnatural redox cofactor in vivo. To the contrary, wild type Bs GDH was able to use the natural cofactors NAD(P)$^+$ in vivo and rescued growth without XenA overexpression or NMN$^+$ supplementation (see FIG. 12).

In vivo NMN(H) cycling enables orthogonal reducing power-delivery in *E. coli*. Compared to in vitro biotransformation, whole cell-based processes are considered more robust and inexpensive. However, one drawback is that the host's natural metabolism often interferes with the desired biotransformation reaction in vivo. For example, reduction of carboxylic acid precursors by the carboxylic acid reductases (CARs) is a promising route to synthesize aldehydes as biofuels, favors, and fragrance compounds. However, aldehydes are often further reduced by the numerous, non-specific, C═O bond reducing-enzymes native to the hosts. As such, a tool is needed to deliver reducing power only to the desired reaction in vivo. It was sought to test if the GDH Ortho-mediated NMN(H) cycling system can serve as such a tool.

The levodione production reaction (see FIGS. 7A-B) was chosen as the model system. In the substrate KIP, three sites are susceptible for enzymatic reduction (see FIG. 13A). While reduction of the C═C double bond by XenA yields the desired product levodione, reduction of the two C═O groups by the enzymes levodione reductase (LVR from *Corynebacterium aquaticum*) and alcohol dehydrogenase (ADH from *Ralstonia* sp) will result in the side products phorenol and 4-hydroxyisophorone (HIP), respectively.

The whole-cell biotransformation chassis was built by disrupting pgi, zwf, and gntK genes in *E. coli* (see FIG. 14), leaving GDH the only enzyme that can generate reducing power from glucose. Next, wild type Bs GDH or GDH Ortho was paired with XenA, LVR, or ADH, individually (see FIGS. 13B-D). In resting cells with XenA and wild type GDH, the whole cells produced ~2 g/L levodione from 5 g/L KIP, using glucose as the co-substrate. Importantly, GDH Ortho was also able to power the XenA-catalyzed reaction with NMN$^+$ supplementation in the buffer (~1 g/L levodione was formed under the same conditions) (see FIG. 13B). By contrast, LVR and ADH-catalyzed reactions were only active when wild type GDH was used as the cofactor recycling enzyme (see FIGS. 13C-D). When GDH Ortho was used, minimal levels of phorenol or HIP was produced (see FIGS. 13C-D), indicating that LVR and ADH, which catalyze the competing reactions in our model system, were not supplied with reducing power.

Figure 15A:
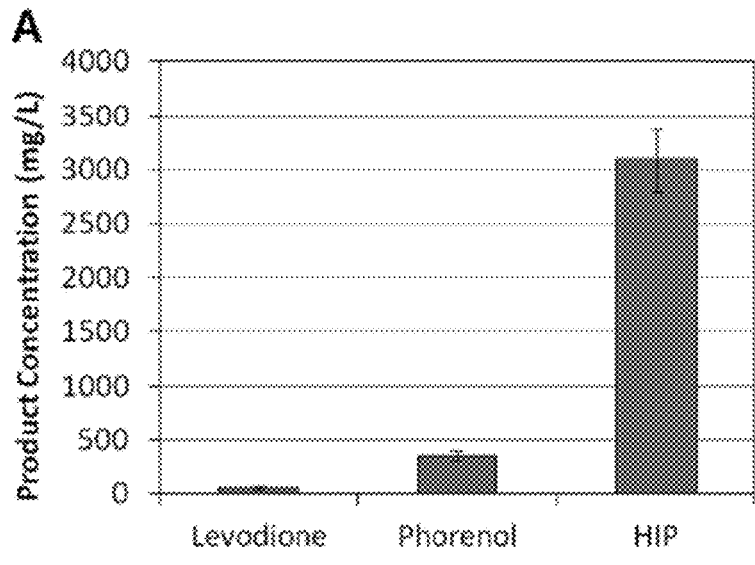
FIG. 15A-B provides product levels in whole-cell ketoisophorone (KIP) conversion with co-expression of XenA, LVR, and ADH. With simultaneous expression of all three KIP converting enzymes, the principal product was determined by the cofactor specificity of GDH. (A) Production of 4-hydroxyisophorone (HIP) was dominant when the redox system was coupled with GDH WT ($NAD(P)^+$ preference). (B) Production of levodione was dominant when the redox system was coupled with GDH Ortho ($NMN^+$ preference). XenA, enoate reductase from *Pseudomonas putida*. LVR, levodione reductase from *Corynebacterium aquaticum*. ADH, alcohol dehydrogenase from *Ralstonia* sp. The error bars represent one standard deviation above the mean of triplicate experiments.
Figure 15B:
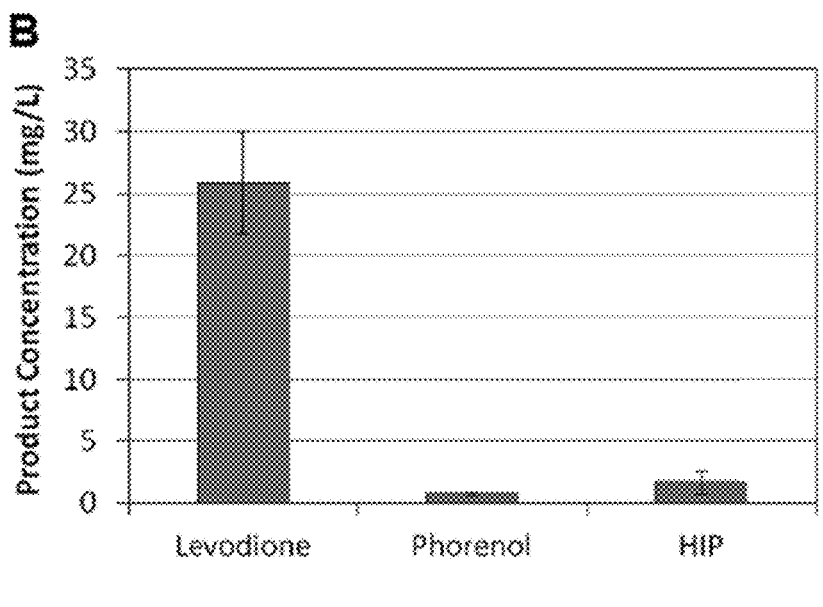

Lastly, XenA, LVR, and ADH were over-expressed simultaneously in resting cells, which resulted in a mixture of products being formed from KIP. Interestingly, by using different GDH variants to generate reducing power, the composition of the mixtures can shift greatly (see FIGS. 5E-F). When using wild type GDH to generate NADH and NADPH, all three enzymes were active. However, XenA could not compete favorably with LVR and ADH for substrate conversion, which led to low product-to-byproduct ratio (levodione only constituted ~2% of total products by mass, FIG. 13E). On the other hand, when using GDH Ortho, the fraction of levodione in the product mixture increased to ~92%. Analysis of the levodione, phorenol, and HIP concentrations suggested that the improved ratio was largely due to the substantially decreased byproduct formation (see FIG. 15). These results support that NMNH can be established as an alternative reducing power in *E. coli* to increase selectivity in whole-cell biotransformation.

Certain embodiments of the invention have been described. It will be understood that various modifications may be made without departing from the spirit and scope of the invention. Other embodiments are within the scope of the following claims.

---

What is claimed is:

1. An engineered polypeptide having dehydrogenase activity that exhibits catalytic efficiency for a nicotinamide-based unnatural cofactor, wherein the engineered polypeptide comprises 1, 2, 3, 4, 5, 6, 7, or 8 introduced amino acid substitutions in comparison to the sequence of a wild-type or parent polypeptide having the polypeptide sequence of SEQ ID NO:1, wherein the introduced amino acid substitutions comprise at least the substitution of I195R in comparison to SEQ ID NO:1, wherein the cofactor normally utilized by the wild-type or parent polypeptide is nicotinamide adenine dinucleotide (NAD+) or nicotinamide adenine dinucleotide phosphate (NADP+), wherein the nicotinamide-based unnatural cofactor is a cofactor that is not normally utilized by the dehydrogenase encoded by the wild-type or parent polypeptide to catalyze a reaction and which is selected from the group consisting of nicotinamide mononucleotide (NMN$^+$), 1-phenyl-1,4,-dihydronicotinamide (PNA$^+$), 1-benzyl-1,4-dihydronicotinamide (BNA$^+$), 1-(4-hydroxyphenyl) 1,4-dihydronicotinamide (HPNA$^+$), 1-methyl-1,4-dihydronicotinamide (MNA$^+$), nicotinamide flucytosine dinucleotide (NFCD$^+$), and nicotinamide mononucleoside (NR$^+$).

2. The engineered polypeptide of claim 1, wherein the nicotinamide-based unnatural cofactor is NMN+.

3. The engineered polypeptide of claim 1, wherein the engineered polypeptide further comprises the introduced amino acid substitutions of A93K and Y39Q in comparison to SEQ ID NO:1.

4. The engineered polypeptide of claim 1, wherein the engineered polypeptide comprises a sequence selected from SEQ ID NO:2 or SEQ ID NO:6.

5. The engineered polypeptide of claim 1, wherein the engineered polypeptide further comprises the introduced amino acid substitution of S17E in comparison to SEQ ID NO:1.

6. The engineered polypeptide of claim 3, wherein the engineered polypeptide further comprises the introduced amino acid substitution of S17E in comparison to SEQ ID NO:1.

7. The engineered polypeptide of claim 6, wherein the engineered polypeptide comprises the sequence of SEQ ID NO:7.

* * * * *

SEQUENCE LISTING

```
<160> NUMBER OF SEQ ID NOS: 25

<210> SEQ ID NO 1
<211> LENGTH: 261
<212> TYPE: PRT
<213> ORGANISM: Bacillus subtilis

<400> SEQUENCE: 1

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
            35                  40                  45

Lys Glu Glu Val Ile Lys Ala Gly Gly Glu Ala Val Val Val Gln Gly
        50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
                100                 105                 110

Ile Gly Thr Asn Leu Thr Gly Ala Phe Leu Gly Ser Arg Glu Ala Ile
            115                 120                 125

Lys Tyr Phe Val Glu Asn Asp Ile Lys Gly Asn Val Ile Asn Met Ser
        130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
                180                 185                 190

Thr Pro Ile Asn Ala Glu Lys Phe Ala Asp Pro Lys Gln Lys Ala Asp
            195                 200                 205

Val Glu Ser Met Ile Pro Met Gly Tyr Ile Gly Glu Pro Glu Glu Ile
        210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
                260

<210> SEQ ID NO 2
<211> LENGTH: 261
<212> TYPE: PRT
<213> ORGANISM: Artificial Sequence
<220> FEATURE:
<223> OTHER INFORMATION: I195R mutant GDH coding sequence
```

-continued

```
<400> SEQUENCE: 2

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
            115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Arg Asn Ala Glu Lys Phe Ala Asp Pro Lys Gln Lys Ala Asp
            195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
                260

<210> SEQ ID NO 3
<211> LENGTH: 261
<212> TYPE: PRT
<213> ORGANISM: Artificial Sequence
<220> FEATURE:
<223> OTHER INFORMATION: A93K mutant GDH coding sequence

<400> SEQUENCE: 3

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80
```

Lys Glu Phe Gly Thr Leu Asp Ile Met Ile Asn Asn Lys Gly Leu Glu
                85                  90                  95

Asn Pro Val Pro Ser His Glu Met Pro Leu Lys Asp Trp Asp Lys Val
                100                 105                 110

Ile Gly Thr Asn Leu Thr Gly Ala Phe Leu Gly Ser Arg Glu Ala Ile
                115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
                180                 185                 190

Thr Pro Ile Asn Ala Glu Lys Phe Ala Asp Pro Lys Gln Lys Ala Asp
                195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
                260

<210> SEQ ID NO 4
<211> LENGTH: 261
<212> TYPE: PRT
<213> ORGANISM: Artificial Sequence
<220> FEATURE:
<223> OTHER INFORMATION: Y39Q mutant GDH coding sequence

<400> SEQUENCE: 4

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
                20                  25                  30

Lys Val Val Ile Asn Tyr Gln Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
                100                 105                 110

Ile Gly Thr Asn Leu Thr Gly Ala Phe Leu Gly Ser Arg Glu Ala Ile
                115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

-continued

```
Ala Pro Lys Gly Ile Arg Val Asn Asn Ile Gly Pro Gly Ala Ile Asn
            180              185              190

Thr Pro Ile Asn Ala Glu Lys Phe Ala Asp Pro Lys Gln Lys Ala Asp
            195              200              205

Val Glu Ser Met Ile Pro Met Gly Tyr Ile Gly Glu Pro Glu Glu Ile
        210              215              220

Ala Ala Val Ala Ala Trp Leu Ala Ser Lys Glu Ala Ser Tyr Val Thr
225              230              235              240

Gly Ile Thr Leu Phe Ala Asp Gly Gly Met Thr Gln Tyr Pro Ser Phe
            245              250              255

Gln Ala Gly Arg Gly
            260

<210> SEQ ID NO 5
<211> LENGTH: 261
<212> TYPE: PRT
<213> ORGANISM: Artificial Sequence
<220> FEATURE:
<223> OTHER INFORMATION: S17E mutant GDH coding sequence

<400> SEQUENCE: 5

Met Tyr Pro Asp Leu Lys Gly Lys Val Val Ala Ile Thr Gly Ala Ala
1               5               10              15

Glu Gly Leu Gly Lys Ala Met Ala Ile Arg Phe Gly Lys Glu Gln Ala
            20              25              30

Lys Val Val Ile Asn Tyr Tyr Ser Asn Lys Gln Asp Pro Asn Glu Val
            35              40              45

Lys Glu Glu Val Ile Lys Ala Gly Gly Glu Ala Val Val Val Gln Gly
        50              55              60

Asp Val Thr Lys Glu Glu Asp Val Lys Asn Ile Val Gln Thr Ala Ile
65              70              75              80

Lys Glu Phe Gly Thr Leu Asp Ile Met Ile Asn Asn Ala Gly Leu Glu
            85              90              95

Asn Pro Val Pro Ser His Glu Met Pro Leu Lys Asp Trp Asp Lys Val
            100             105             110

Ile Gly Thr Asn Leu Thr Gly Ala Phe Leu Gly Ser Arg Glu Ala Ile
            115             120             125

Lys Tyr Phe Val Glu Asn Asp Ile Lys Gly Asn Val Ile Asn Met Ser
        130             135             140

Ser Val His Glu Val Ile Pro Trp Pro Leu Phe Val His Tyr Ala Ala
145             150             155             160

Ser Lys Gly Gly Ile Lys Leu Met Thr Glu Thr Leu Ala Leu Glu Tyr
            165             170             175

Ala Pro Lys Gly Ile Arg Val Asn Asn Ile Gly Pro Gly Ala Ile Asn
            180             185             190

Thr Pro Ile Asn Ala Glu Lys Phe Ala Asp Pro Lys Gln Lys Ala Asp
            195             200             205

Val Glu Ser Met Ile Pro Met Gly Tyr Ile Gly Glu Pro Glu Glu Ile
        210             215             220

Ala Ala Val Ala Ala Trp Leu Ala Ser Lys Glu Ala Ser Tyr Val Thr
225             230             235             240

Gly Ile Thr Leu Phe Ala Asp Gly Gly Met Thr Gln Tyr Pro Ser Phe
            245             250             255

Gln Ala Gly Arg Gly
            260
```

-continued

<210> SEQ ID NO 6
<211> LENGTH: 261
<212> TYPE: PRT
<213> ORGANISM: Artificial Sequence
<220> FEATURE:
<223> OTHER INFORMATION: I195R A93K Y39Q mutant GDH coding sequence

<400> SEQUENCE: 6

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Gln Ser Asn Lys Gln Asp Pro Asn Glu Val
            35                  40                  45

Lys Glu Glu Val Ile Lys Ala Gly Gly Glu Ala Val Val Gln Gly
        50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Lys Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
            115                 120                 125

Lys Tyr Phe Val Glu Asn Asp Ile Lys Gly Asn Val Ile Asn Met Ser
        130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Arg Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
        210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260
```

<210> SEQ ID NO 7
<211> LENGTH: 261
<212> TYPE: PRT
<213> ORGANISM: Artificial Sequence
<220> FEATURE:
<223> OTHER INFORMATION: I195R A93K Y39Q S17E mutant GDH coding sequence

<400> SEQUENCE: 7

```
Met Tyr Pro Asp Leu Lys Gly Lys Val Val Ala Ile Thr Gly Ala Ala
1               5                   10                  15

Glu Gly Leu Gly Lys Ala Met Ala Ile Arg Phe Gly Lys Glu Gln Ala
            20                  25                  30

Lys Val Val Ile Asn Tyr Gln Ser Asn Lys Gln Asp Pro Asn Glu Val
            35                  40                  45
```

```
Lys Glu Glu Val Ile Lys Ala Gly Gly Glu Ala Val Val Val Gln Gly
    50              55              60

Asp Val Thr Lys Glu Glu Asp Val Lys Asn Ile Val Gln Thr Ala Ile
65              70              75              80

Lys Glu Phe Gly Thr Leu Asp Ile Met Ile Asn Asn Lys Gly Leu Glu
                85              90              95

Asn Pro Val Pro Ser His Glu Met Pro Leu Lys Asp Trp Asp Lys Val
            100             105             110

Ile Gly Thr Asn Leu Thr Gly Ala Phe Leu Gly Ser Arg Glu Ala Ile
        115             120             125

Lys Tyr Phe Val Glu Asn Asp Ile Lys Gly Asn Val Ile Asn Met Ser
    130             135             140

Ser Val His Glu Val Ile Pro Trp Pro Leu Phe Val His Tyr Ala Ala
145             150             155             160

Ser Lys Gly Gly Ile Lys Leu Met Thr Glu Thr Leu Ala Leu Glu Tyr
            165             170             175

Ala Pro Lys Gly Ile Arg Val Asn Asn Ile Gly Pro Gly Ala Ile Asn
            180             185             190

Thr Pro Arg Asn Ala Glu Lys Phe Ala Asp Pro Lys Gln Lys Ala Asp
        195             200             205

Val Glu Ser Met Ile Pro Met Gly Tyr Ile Gly Glu Pro Glu Glu Ile
    210             215             220

Ala Ala Val Ala Ala Trp Leu Ala Ser Lys Glu Ala Ser Tyr Val Thr
225             230             235             240

Gly Ile Thr Leu Phe Ala Asp Gly Gly Met Thr Gln Tyr Pro Ser Phe
            245             250             255

Gln Ala Gly Arg Gly
            260

<210> SEQ ID NO 8
<211> LENGTH: 165
<212> TYPE: PRT
<213> ORGANISM: Escherichia coli

<400> SEQUENCE: 8

Met Thr Asp Ser Glu Leu Met Gln Leu Ser Glu Gln Val Gly Gln Ala
1               5               10              15

Leu Lys Ala Arg Gly Ala Thr Val Thr Thr Ala Glu Ser Cys Thr Gly
            20              25              30

Gly Trp Val Ala Lys Val Ile Thr Asp Ile Ala Gly Ser Ser Ala Trp
        35              40              45

Phe Glu Arg Gly Phe Val Thr Tyr Ser Asn Glu Ala Lys Ala Gln Met
    50              55              60

Ile Gly Val Arg Glu Glu Thr Leu Ala Gln His Gly Ala Val Ser Glu
65              70              75              80

Pro Val Val Val Glu Met Ala Ile Gly Ala Leu Lys Ala Ala Arg Ala
                85              90              95

Asp Tyr Ala Val Ser Ile Ser Gly Ile Ala Gly Pro Asp Gly Gly Ser
            100             105             110

Glu Glu Lys Pro Val Gly Thr Val Trp Phe Ala Phe Ala Thr Ala Arg
            115             120             125

Gly Glu Gly Ile Thr Arg Arg Glu Cys Phe Ser Gly Asp Arg Asp Ala
        130             135             140

Val Arg Arg Gln Ala Thr Ala Tyr Ala Leu Gln Thr Leu Trp Gln Gln
```

-continued

```
145              150              155              160

Phe Leu Gln Asn Thr
                165

<210> SEQ ID NO 9
<211> LENGTH: 410
<212> TYPE: PRT
<213> ORGANISM: Escherichia coli

<400> SEQUENCE: 9

Met Ser Ser Phe Asp Tyr Leu Lys Thr Ala Ile Lys Gln Gln Gly Cys
1               5                   10                  15

Thr Leu Gln Gln Val Ala Asp Ala Ser Gly Met Thr Lys Gly Tyr Leu
            20                  25                  30

Ser Gln Leu Leu Asn Ala Lys Ile Lys Ser Pro Ser Ala Gln Lys Leu
        35                  40                  45

Glu Ala Leu His Arg Phe Leu Gly Leu Glu Phe Pro Arg Gln Lys Lys
    50                  55                  60

Thr Ile Gly Val Val Phe Gly Lys Phe Tyr Pro Leu His Thr Gly His
65                  70                  75                  80

Ile Tyr Leu Ile Gln Arg Ala Cys Ser Gln Val Asp Glu Leu His Ile
                85                  90                  95

Ile Met Gly Phe Asp Asp Thr Arg Asp Arg Ala Leu Phe Glu Asp Ser
            100                 105                 110

Ala Met Ser Gln Gln Pro Thr Val Pro Asp Arg Leu Arg Trp Leu Leu
        115                 120                 125

Gln Thr Phe Lys Tyr Gln Lys Asn Ile Arg Ile His Ala Phe Asn Glu
    130                 135                 140

Glu Gly Met Glu Pro Tyr Pro His Gly Trp Asp Val Trp Ser Asn Gly
145                 150                 155                 160

Ile Lys Lys Phe Met Ala Glu Lys Gly Ile Gln Pro Asp Leu Ile Tyr
                165                 170                 175

Thr Ser Glu Glu Ala Asp Ala Pro Gln Tyr Met Glu His Leu Gly Ile
            180                 185                 190

Glu Thr Val Leu Val Asp Pro Lys Arg Thr Phe Met Ser Ile Ser Gly
        195                 200                 205

Ala Gln Ile Arg Glu Asn Pro Phe Arg Tyr Trp Glu Tyr Ile Pro Thr
    210                 215                 220

Glu Val Lys Pro Phe Phe Val Arg Thr Val Ala Ile Leu Gly Gly Glu
225                 230                 235                 240

Ser Ser Gly Lys Ser Thr Leu Val Asn Lys Leu Ala Asn Ile Phe Asn
                245                 250                 255

Thr Thr Ser Ala Trp Glu Tyr Gly Arg Asp Tyr Val Phe Ser His Leu
            260                 265                 270

Gly Gly Asp Glu Ile Ala Leu Gln Tyr Ser Asp Tyr Asp Lys Ile Ala
        275                 280                 285

Leu Gly His Ala Gln Tyr Ile Asp Phe Ala Val Lys Tyr Ala Asn Lys
    290                 295                 300

Val Ala Phe Ile Asp Thr Asp Phe Val Thr Thr Gln Ala Phe Cys Lys
305                 310                 315                 320

Lys Tyr Glu Gly Arg Glu His Pro Phe Val Gln Ala Leu Ile Asp Glu
                325                 330                 335

Tyr Arg Phe Asp Leu Val Ile Leu Leu Glu Asn Asn Thr Pro Trp Val
            340                 345                 350
```

-continued

```
Ala Asp Gly Leu Arg Ser Leu Gly Ser Ser Val Asp Arg Lys Glu Phe
        355                 360                 365

Gln Asn Leu Leu Val Glu Met Leu Glu Glu Asn Asn Ile Glu Phe Val
        370                 375                 380

Arg Val Glu Glu Glu Asp Tyr Asp Ser Arg Phe Leu Arg Cys Val Glu
385                 390                 395                 400

Leu Val Arg Glu Met Met Gly Glu Gln Arg
                405                 410

<210> SEQ ID NO 10
<211> LENGTH: 549
<212> TYPE: PRT
<213> ORGANISM: Escherichia coli

<400> SEQUENCE: 10

Met Lys Asn Ile Asn Pro Thr Gln Thr Ala Ala Trp Gln Ala Leu Gln
1                   5                   10                  15

Lys His Phe Asp Glu Met Lys Asp Val Thr Ile Ala Asp Leu Phe Ala
                20                  25                  30

Lys Asp Gly Asp Arg Phe Ser Lys Phe Ser Ala Thr Phe Asp Asp Gln
        35                  40                  45

Met Leu Val Asp Tyr Ser Lys Asn Arg Ile Thr Glu Glu Thr Leu Ala
        50                  55                  60

Lys Leu Gln Asp Leu Ala Lys Glu Cys Asp Leu Ala Gly Ala Ile Lys
65                  70                  75                  80

Ser Met Phe Ser Gly Glu Lys Ile Asn Arg Thr Glu Asn Arg Ala Val
                85                  90                  95

Leu His Val Ala Leu Arg Asn Arg Ser Asn Thr Pro Ile Leu Val Asp
                100                 105                 110

Gly Lys Asp Val Met Pro Glu Val Asn Ala Val Leu Glu Lys Met Lys
        115                 120                 125

Thr Phe Ser Glu Ala Ile Ile Ser Gly Glu Trp Lys Gly Tyr Thr Gly
        130                 135                 140

Lys Ala Ile Thr Asp Val Val Asn Ile Gly Ile Gly Gly Ser Asp Leu
145                 150                 155                 160

Gly Pro Tyr Met Val Thr Glu Ala Leu Arg Pro Tyr Lys Asn His Leu
                165                 170                 175

Asn Met His Phe Val Ser Asn Val Asp Gly Thr His Ile Ala Glu Val
                180                 185                 190

Leu Lys Lys Val Asn Pro Glu Thr Thr Leu Phe Leu Val Ala Ser Lys
        195                 200                 205

Thr Phe Thr Thr Gln Glu Thr Met Thr Asn Ala His Ser Ala Arg Asp
        210                 215                 220

Trp Phe Leu Lys Ala Ala Gly Asp Glu Lys His Val Ala Lys His Phe
225                 230                 235                 240

Ala Ala Leu Ser Thr Asn Ala Lys Ala Val Gly Glu Phe Gly Ile Asp
                245                 250                 255

Thr Ala Asn Met Phe Glu Phe Trp Asp Trp Val Gly Gly Arg Tyr Ser
                260                 265                 270

Leu Trp Ser Ala Ile Gly Leu Ser Ile Val Leu Ser Ile Gly Phe Asp
        275                 280                 285

Asn Phe Val Glu Leu Leu Ser Gly Ala His Ala Met Asp Lys His Phe
        290                 295                 300

Ser Thr Thr Pro Ala Glu Lys Asn Leu Pro Val Leu Leu Ala Leu Ile
305                 310                 315                 320
```

-continued

```
Gly Ile Trp Tyr Asn Asn Phe Phe Gly Ala Glu Thr Glu Ala Ile Leu
            325                 330                 335

Pro Tyr Asp Gln Tyr Met His Arg Phe Ala Ala Tyr Phe Gln Gln Gly
            340                 345                 350

Asn Met Glu Ser Asn Gly Lys Tyr Val Asp Arg Asn Gly Asn Val Val
            355                 360                 365

Asp Tyr Gln Thr Gly Pro Ile Ile Trp Gly Glu Pro Gly Thr Asn Gly
    370                 375                 380

Gln His Ala Phe Tyr Gln Leu Ile His Gln Gly Thr Lys Met Val Pro
385                 390                 395                 400

Cys Asp Phe Ile Ala Pro Ala Ile Thr His Asn Pro Leu Ser Asp His
                405                 410                 415

His Gln Lys Leu Leu Ser Asn Phe Phe Ala Gln Thr Glu Ala Leu Ala
            420                 425                 430

Phe Gly Lys Ser Arg Glu Val Val Glu Gln Glu Tyr Arg Asp Gln Gly
            435                 440                 445

Lys Asp Pro Ala Thr Leu Asp Tyr Val Val Pro Phe Lys Val Phe Glu
    450                 455                 460

Gly Asn Arg Pro Thr Asn Ser Ile Leu Leu Arg Glu Ile Thr Pro Phe
465                 470                 475                 480

Ser Leu Gly Ala Leu Ile Ala Leu Tyr Glu His Lys Ile Phe Thr Gln
                485                 490                 495

Gly Val Ile Leu Asn Ile Phe Thr Phe Asp Gln Trp Gly Val Glu Leu
            500                 505                 510

Gly Lys Gln Leu Ala Asn Arg Ile Leu Pro Glu Leu Lys Asp Asp Lys
            515                 520                 525

Glu Ile Ser Ser His Asp Ser Ser Thr Asn Gly Leu Ile Asn Arg Tyr
    530                 535                 540

Lys Ala Trp Arg Gly
545

<210> SEQ ID NO 11
<211> LENGTH: 491
<212> TYPE: PRT
<213> ORGANISM: Escherichia coli

<400> SEQUENCE: 11

Met Ala Val Thr Gln Thr Ala Gln Ala Cys Asp Leu Val Ile Phe Gly
1               5                   10                  15

Ala Lys Gly Asp Leu Ala Arg Arg Lys Leu Leu Pro Ser Leu Tyr Gln
            20                  25                  30

Leu Glu Lys Ala Gly Gln Leu Asn Pro Asp Thr Arg Ile Ile Gly Val
            35                  40                  45

Gly Arg Ala Asp Trp Asp Lys Ala Ala Tyr Thr Lys Val Val Arg Glu
    50                  55                  60

Ala Leu Glu Thr Phe Met Lys Glu Thr Ile Asp Glu Gly Leu Trp Asp
65                  70                  75                  80

Thr Leu Ser Ala Arg Leu Asp Phe Cys Asn Leu Asp Val Asn Asp Thr
                85                  90                  95

Ala Ala Phe Ser Arg Leu Gly Ala Met Leu Asp Gln Lys Asn Arg Ile
            100                 105                 110

Thr Ile Asn Tyr Phe Ala Met Pro Pro Ser Thr Phe Gly Ala Ile Cys
            115                 120                 125

Lys Gly Leu Gly Glu Ala Lys Leu Asn Ala Lys Pro Ala Arg Val Val
```

-continued

```
          130                 135                 140

Met Glu Lys Pro Leu Gly Thr Ser Leu Ala Thr Ser Gln Glu Ile Asn
145                 150                 155                 160

Asp Gln Val Gly Glu Tyr Phe Glu Glu Cys Gln Val Tyr Arg Ile Asp
                165                 170                 175

His Tyr Leu Gly Lys Glu Thr Val Leu Asn Leu Leu Ala Leu Arg Phe
                180                 185                 190

Ala Asn Ser Leu Phe Val Asn Asn Trp Asp Asn Arg Thr Ile Asp His
            195                 200                 205

Val Glu Ile Thr Val Ala Glu Glu Val Gly Ile Glu Gly Arg Trp Gly
        210                 215                 220

Tyr Phe Asp Lys Ala Gly Gln Met Arg Asp Met Ile Gln Asn His Leu
225                 230                 235                 240

Leu Gln Ile Leu Cys Met Ile Ala Met Ser Pro Pro Ser Asp Leu Ser
                245                 250                 255

Ala Asp Ser Ile Arg Asp Glu Lys Val Lys Val Leu Lys Ser Leu Arg
                260                 265                 270

Arg Ile Asp Arg Ser Asn Val Arg Glu Lys Thr Val Arg Gly Gln Tyr
                275                 280                 285

Thr Ala Gly Phe Ala Gln Gly Lys Lys Val Pro Gly Tyr Leu Glu Glu
        290                 295                 300

Glu Gly Ala Asn Lys Ser Ser Asn Thr Glu Thr Phe Val Ala Ile Arg
305                 310                 315                 320

Val Asp Ile Asp Asn Trp Arg Trp Ala Gly Val Pro Phe Tyr Leu Arg
                325                 330                 335

Thr Gly Lys Arg Leu Pro Thr Lys Cys Ser Glu Val Val Val Tyr Phe
                340                 345                 350

Lys Thr Pro Glu Leu Asn Leu Phe Lys Glu Ser Trp Gln Asp Leu Pro
                355                 360                 365

Gln Asn Lys Leu Thr Ile Arg Leu Gln Pro Asp Glu Gly Val Asp Ile
        370                 375                 380

Gln Val Leu Asn Lys Val Pro Gly Leu Asp His Lys His Asn Leu Gln
385                 390                 395                 400

Ile Thr Lys Leu Asp Leu Ser Tyr Ser Glu Thr Phe Asn Gln Thr His
                405                 410                 415

Leu Ala Asp Ala Tyr Glu Arg Leu Leu Leu Glu Thr Met Arg Gly Ile
                420                 425                 430

Gln Ala Leu Phe Val Arg Arg Asp Glu Val Glu Glu Ala Trp Lys Trp
                435                 440                 445

Val Asp Ser Ile Thr Glu Ala Trp Ala Met Asp Asn Asp Ala Pro Lys
        450                 455                 460

Pro Tyr Gln Ala Gly Thr Trp Gly Pro Val Ala Ser Val Ala Met Ile
465                 470                 475                 480

Thr Arg Asp Gly Arg Ser Trp Asn Glu Phe Glu
                485                 490
```

```
<210> SEQ ID NO 12
<211> LENGTH: 468
<212> TYPE: PRT
<213> ORGANISM: Escherichia coli

<400> SEQUENCE: 12

Met Ser Lys Gln Gln Ile Gly Val Val Gly Met Ala Val Met Gly Arg
1               5                   10                  15
```

-continued

```
Asn Leu Ala Leu Asn Ile Glu Ser Arg Gly Tyr Thr Val Ser Ile Phe
              20                  25                  30

Asn Arg Ser Arg Glu Lys Thr Glu Glu Val Ile Ala Glu Asn Pro Gly
          35                  40                  45

Lys Lys Leu Val Pro Tyr Tyr Thr Val Lys Glu Phe Val Glu Ser Leu
      50                  55                  60

Glu Thr Pro Arg Arg Ile Leu Leu Met Val Lys Ala Gly Ala Gly Thr
65                  70                  75                  80

Asp Ala Ala Ile Asp Ser Leu Lys Pro Tyr Leu Asp Lys Gly Asp Ile
              85                  90                  95

Ile Ile Asp Gly Gly Asn Thr Phe Phe Gln Asp Thr Ile Arg Arg Asn
          100                 105                 110

Arg Glu Leu Ser Ala Glu Gly Phe Asn Phe Ile Gly Thr Gly Val Ser
          115                 120                 125

Gly Gly Glu Glu Gly Ala Leu Lys Gly Pro Ser Ile Met Pro Gly Gly
      130                 135                 140

Gln Lys Glu Ala Tyr Glu Leu Val Ala Pro Ile Leu Thr Lys Ile Ala
145                 150                 155                 160

Ala Val Ala Glu Asp Gly Glu Pro Cys Val Thr Tyr Ile Gly Ala Asp
              165                 170                 175

Gly Ala Gly His Tyr Val Lys Met Val His Asn Gly Ile Glu Tyr Gly
          180                 185                 190

Asp Met Gln Leu Ile Ala Glu Ala Tyr Ser Leu Leu Lys Gly Gly Leu
          195                 200                 205

Asn Leu Thr Asn Glu Glu Leu Ala Gln Thr Phe Thr Glu Trp Asn Asn
      210                 215                 220

Gly Glu Leu Ser Ser Tyr Leu Ile Asp Ile Thr Lys Asp Ile Phe Thr
225                 230                 235                 240

Lys Lys Asp Glu Asp Gly Asn Tyr Leu Val Asp Val Ile Leu Asp Glu
              245                 250                 255

Ala Ala Asn Lys Gly Thr Gly Lys Trp Thr Ser Gln Ser Ala Leu Asp
              260                 265                 270

Leu Gly Glu Pro Leu Ser Leu Ile Thr Glu Ser Val Phe Ala Arg Tyr
          275                 280                 285

Ile Ser Ser Leu Lys Asp Gln Arg Val Ala Ala Ser Lys Val Leu Ser
      290                 295                 300

Gly Pro Gln Ala Gln Pro Ala Gly Asp Lys Ala Glu Phe Ile Glu Lys
305                 310                 315                 320

Val Arg Arg Ala Leu Tyr Leu Gly Lys Ile Val Ser Tyr Ala Gln Gly
              325                 330                 335

Phe Ser Gln Leu Arg Ala Ala Ser Glu Glu Tyr Asn Trp Asp Leu Asn
          340                 345                 350

Tyr Gly Glu Ile Ala Lys Ile Phe Arg Ala Gly Cys Ile Ile Arg Ala
          355                 360                 365

Gln Phe Leu Gln Lys Ile Thr Asp Ala Tyr Ala Glu Asn Pro Gln Ile
      370                 375                 380

Ala Asn Leu Leu Leu Ala Pro Tyr Phe Lys Gln Ile Ala Asp Asp Tyr
385                 390                 395                 400

Gln Gln Ala Leu Arg Asp Val Val Ala Tyr Ala Val Gln Asn Gly Ile
              405                 410                 415

Pro Val Pro Thr Phe Ser Ala Ala Val Ala Tyr Tyr Asp Ser Tyr Arg
          420                 425                 430

Ala Ala Val Leu Pro Ala Asn Leu Ile Gln Ala Gln Arg Asp Tyr Phe
```

-continued

```
                435                 440                 445
Gly Ala His Thr Tyr Lys Arg Ile Asp Lys Glu Gly Val Phe His Thr
    450                 455                 460

Glu Trp Leu Asp
465

<210> SEQ ID NO 13
<211> LENGTH: 175
<212> TYPE: PRT
<213> ORGANISM: Escherichia coli

<400> SEQUENCE: 13

Met Ser Thr Thr Asn His Asp His His Ile Tyr Val Leu Met Gly Val
1               5                   10                  15

Ser Gly Ser Gly Lys Ser Ala Val Ala Ser Glu Val Ala His Gln Leu
                20                  25                  30

His Ala Ala Phe Leu Asp Gly Asp Phe Leu His Pro Arg Arg Asn Ile
            35                  40                  45

Glu Lys Met Ala Ser Gly Glu Pro Leu Asn Asp Asp Asp Arg Lys Pro
        50                  55                  60

Trp Leu Gln Ala Leu Asn Asp Ala Ala Phe Ala Met Gln Arg Thr Asn
65                  70                  75                  80

Lys Val Ser Leu Ile Val Cys Ser Ala Leu Lys Lys His Tyr Arg Asp
                85                  90                  95

Leu Leu Arg Glu Gly Asn Pro Asn Leu Ser Phe Ile Tyr Leu Lys Gly
            100                 105                 110

Asp Phe Asp Val Ile Glu Ser Arg Leu Lys Ala Arg Lys Gly His Phe
            115                 120                 125

Phe Lys Thr Gln Met Leu Val Thr Gln Phe Glu Thr Leu Gln Glu Pro
        130                 135                 140

Gly Ala Asp Glu Thr Asp Val Leu Val Val Asp Ile Asp Gln Pro Leu
145                 150                 155                 160

Glu Gly Val Val Ala Ser Thr Ile Glu Val Ile Lys Lys Gly Lys
                165                 170                 175

<210> SEQ ID NO 14
<211> LENGTH: 217
<212> TYPE: PRT
<213> ORGANISM: Escherichia coli

<400> SEQUENCE: 14

Met Asp Ile Ile Ser Val Ala Leu Lys Arg His Ser Thr Lys Ala Phe
1               5                   10                  15

Asp Ala Ser Lys Lys Leu Thr Pro Glu Gln Ala Glu Gln Ile Lys Thr
                20                  25                  30

Leu Leu Gln Tyr Ser Pro Ser Ser Thr Asn Ser Gln Pro Trp His Phe
            35                  40                  45

Ile Val Ala Ser Thr Glu Glu Gly Lys Ala Arg Val Ala Lys Ser Ala
        50                  55                  60

Ala Gly Asn Tyr Val Phe Asn Glu Arg Lys Met Leu Asp Ala Ser His
65                  70                  75                  80

Val Val Val Phe Cys Ala Lys Thr Ala Met Asp Asp Val Trp Leu Lys
                85                  90                  95

Leu Val Val Asp Gln Glu Asp Ala Asp Gly Arg Phe Ala Thr Pro Glu
            100                 105                 110

Ala Lys Ala Ala Asn Asp Lys Gly Arg Lys Phe Phe Ala Asp Met His
```

-continued

```
         115                 120                 125

Arg Lys Asp Leu His Asp Asp Ala Glu Trp Met Ala Lys Gln Val Tyr
    130                 135                 140

Leu Asn Val Gly Asn Phe Leu Leu Gly Val Ala Ala Leu Gly Leu Asp
145                 150                 155                 160

Ala Val Pro Ile Glu Gly Phe Asp Ala Ala Ile Leu Asp Ala Glu Phe
                165                 170                 175

Gly Leu Lys Glu Lys Gly Tyr Thr Ser Leu Val Val Val Pro Val Gly
                180                 185                 190

His His Ser Val Glu Asp Phe Asn Ala Thr Leu Pro Lys Ser Arg Leu
                195                 200                 205

Pro Gln Asn Ile Thr Leu Thr Glu Val
    210                 215

<210> SEQ ID NO 15
<211> LENGTH: 249
<212> TYPE: PRT
<213> ORGANISM: Francisella tularensis

<400> SEQUENCE: 15

Met Lys Ile Val Lys Asp Phe Ser Pro Lys Glu Tyr Ser Gln Lys Leu
1               5                 10                  15

Val Asn Trp Leu Ser Asp Ser Cys Met Asn Tyr Pro Ala Glu Gly Phe
                20                  25                  30

Val Ile Gly Leu Ser Gly Gly Ile Asp Ser Ala Val Ala Ala Ser Leu
            35                  40                  45

Ala Val Lys Thr Gly Leu Pro Thr Thr Ala Leu Ile Leu Pro Ser Asp
        50                  55                  60

Asn Asn Gln His Gln Asp Met Gln Asp Ala Leu Glu Leu Ile Glu Met
65                  70                  75                  80

Leu Asn Ile Glu His Tyr Thr Ile Ser Ile Gln Pro Ala Tyr Glu Ala
                85                  90                  95

Phe Leu Ala Ser Thr Gln Ser Phe Thr Asn Leu Gln Asn Asn Arg Gln
                100                 105                 110

Leu Val Ile Lys Gly Asn Ala Gln Ala Arg Leu Arg Met Met Tyr Leu
            115                 120                 125

Tyr Ala Tyr Ala Gln Gln Tyr Asn Arg Ile Val Ile Gly Thr Asp Asn
    130                 135                 140

Ala Cys Glu Trp Tyr Met Gly Tyr Phe Thr Lys Phe Gly Asp Gly Ala
145                 150                 155                 160

Ala Asp Ile Leu Pro Leu Val Asn Leu Lys Lys Ser Gln Val Phe Glu
                165                 170                 175

Leu Gly Lys Tyr Leu Asp Val Pro Lys Asn Ile Leu Asp Lys Ala Pro
                180                 185                 190

Ser Ala Gly Leu Trp Gln Gly Gln Thr Asp Glu Asp Glu Met Gly Val
                195                 200                 205

Thr Tyr Gln Glu Ile Asp Asp Phe Leu Asp Gly Lys Gln Val Ser Ala
    210                 215                 220

Lys Ala Leu Glu Arg Ile Asn Phe Trp His Asn Arg Ser His His Lys
225                 230                 235                 240

Arg Lys Leu Ala Leu Thr Pro Asn Phe
                245

<210> SEQ ID NO 16
<211> LENGTH: 473
```

<212> TYPE: PRT
<213> ORGANISM: Zymomonas mobilis

<400> SEQUENCE: 16

```
Met Ser Ser Glu Ser Ser Gln Gly Leu Val Thr Arg Leu Ala Leu Ile
1               5                   10                  15

Ala Ala Ile Gly Gly Leu Leu Phe Gly Tyr Asp Ser Ala Val Ile Ala
            20                  25                  30

Ala Ile Gly Thr Pro Val Asp Ile His Phe Ile Ala Pro Arg His Leu
        35                  40                  45

Ser Ala Thr Ala Ala Ala Ser Leu Ser Gly Met Val Val Val Ala Val
    50                  55                  60

Leu Val Gly Cys Val Thr Gly Ser Leu Leu Ser Gly Trp Ile Gly Ile
65                  70                  75                  80

Arg Phe Gly Arg Arg Gly Gly Leu Leu Met Ser Ser Ile Cys Phe Val
                85                  90                  95

Ala Ala Gly Phe Gly Ala Ala Leu Thr Glu Lys Leu Phe Gly Thr Gly
            100                 105                 110

Gly Ser Ala Leu Gln Ile Phe Cys Phe Phe Arg Phe Leu Ala Gly Leu
        115                 120                 125

Gly Ile Gly Val Val Ser Thr Leu Thr Pro Thr Tyr Ile Ala Glu Ile
    130                 135                 140

Ala Pro Pro Asp Lys Arg Gly Gln Met Val Ser Gly Gln Gln Met Ala
145                 150                 155                 160

Ile Val Thr Gly Ala Leu Thr Gly Tyr Ile Phe Thr Trp Leu Leu Ala
                165                 170                 175

His Phe Gly Ser Ile Asp Trp Val Asn Ala Ser Gly Trp Cys Trp Ser
            180                 185                 190

Pro Ala Ser Glu Gly Leu Ile Gly Ile Ala Phe Leu Leu Leu Leu Leu
        195                 200                 205

Thr Ala Pro Asp Thr Pro His Trp Leu Val Met Lys Gly Arg His Ser
    210                 215                 220

Glu Ala Ser Lys Ile Leu Ala Arg Leu Glu Pro Gln Ala Asp Pro Asn
225                 230                 235                 240

Leu Thr Ile Gln Lys Ile Lys Ala Gly Phe Asp Lys Ala Met Asp Lys
                245                 250                 255

Ser Ser Ala Gly Leu Phe Ala Phe Gly Ile Thr Val Val Phe Ala Gly
            260                 265                 270

Val Ser Val Ala Ala Phe Gln Gln Leu Val Gly Ile Asn Ala Val Leu
        275                 280                 285

Tyr Tyr Ala Pro Gln Met Phe Gln Asn Leu Gly Phe Gly Ala Asp Thr
    290                 295                 300

Ala Leu Leu Gln Thr Ile Ser Ile Gly Val Val Asn Phe Ile Phe Thr
305                 310                 315                 320

Met Ile Ala Ser Arg Val Val Asp Arg Phe Gly Arg Lys Pro Leu Leu
                325                 330                 335

Ile Trp Gly Ala Leu Gly Met Ala Ala Met Met Ala Val Leu Gly Cys
            340                 345                 350

Cys Phe Trp Phe Lys Val Gly Gly Val Leu Pro Leu Ala Ser Val Leu
        355                 360                 365

Leu Tyr Ile Ala Val Phe Gly Met Ser Trp Gly Pro Val Cys Trp Val
    370                 375                 380

Val Leu Ser Glu Met Phe Pro Ser Ser Ile Lys Gly Ala Ala Met Pro
385                 390                 395                 400
```

-continued

```
Ile Ala Val Thr Gly Gln Trp Leu Ala Asn Ile Leu Val Asn Phe Leu
            405                 410                 415

Phe Lys Val Ala Asp Gly Ser Pro Ala Leu Asn Gln Thr Phe Asn His
            420                 425                 430

Gly Phe Ser Tyr Leu Val Phe Ala Ala Leu Ser Ile Leu Gly Gly Leu
            435                 440                 445

Ile Val Ala Arg Phe Val Pro Glu Thr Lys Gly Arg Ser Leu Asp Glu
        450                 455                 460

Ile Glu Glu Met Trp Arg Ser Gln Lys
465                 470

<210> SEQ ID NO 17
<211> LENGTH: 400
<212> TYPE: PRT
<213> ORGANISM: Saccharomyces cerevisiae

<400> SEQUENCE: 17

Met Pro Phe Val Lys Gly Phe Glu Pro Ile Ser Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60

Pro Gly Thr Met Ile Ile Thr Glu Gly Thr Phe Ile Ser Pro Gln Ala
65                  70                  75                  80

Gly Gly Tyr Asp Asn Ala Pro Gly Ile Trp Ser Asp Glu Gln Val Ala
                85                  90                  95

Glu Trp Lys Asn Ile Phe Leu Ala Ile His Asp Cys Gln Ser Phe Ala
            100                 105                 110

Trp Val Gln Leu Trp Ser Leu Gly Trp Ala Ser Phe Pro Asp Val Leu
            115                 120                 125

Ala Arg Asp Gly Leu Arg Tyr Asp Cys Ala Ser Asp Arg Val Tyr Met
        130                 135                 140

Asn Ala Thr Leu Gln Glu Lys Ala Lys Asp Ala Asn Asn Leu Glu His
145                 150                 155                 160

Ser Leu Thr Lys Asp Asp Ile Lys Gln Tyr Ile Lys Asp Tyr Ile His
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
            195                 200                 205

Lys Arg Thr Asp Glu Tyr Gly Gly Thr Ile Glu Asn Arg Ala Arg Phe
        210                 215                 220

Thr Leu Glu Val Val Asp Ala Leu Ile Glu Thr Ile Gly Pro Glu Arg
225                 230                 235                 240

Val Gly Leu Arg Leu Ser Pro Tyr Gly Thr Phe Asn Ser Met Ser Gly
                245                 250                 255

Gly Ala Glu Pro Gly Ile Ile Ala Gln Tyr Ser Tyr Val Leu Gly Glu
            260                 265                 270

Leu Glu Lys Arg Ala Lys Ala Gly Lys Arg Leu Ala Phe Val His Leu
        275                 280                 285

Val Glu Pro Arg Val Thr Asp Pro Ser Leu Val Glu Gly Glu Gly Glu
```

```
            290                 295                 300
Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
                340                 345                 350

Ser Asn Pro Asp Leu Val Tyr Arg Leu Glu Glu Gly Leu Pro Leu Asn
            355                 360                 365

Lys Tyr Asp Arg Ser Thr Phe Tyr Thr Met Ser Ala Glu Gly Tyr Thr
        370                 375                 380

Asp Tyr Pro Thr Tyr Glu Glu Ala Val Asp Leu Gly Trp Asn Lys Asn
385                 390                 395                 400

<210> SEQ ID NO 18
<211> LENGTH: 181
<212> TYPE: PRT
<213> ORGANISM: Ralstonia eutropha

<400> SEQUENCE: 18

Met Ala Thr Pro Ser Asp Thr Lys Thr Asp Gly Ala Asp Met Ile Tyr
1               5                   10                  15

Ile Leu Met Gly Val Ser Gly Ser Gly Lys Thr Thr Val Gly Gln Leu
                20                  25                  30

Leu Ala Gln Arg Leu Gly Cys Gly Phe His Asp Ala Asp Ala Phe His
            35                  40                  45

Ser Asp Ala Asn Lys Ala Lys Met His Ala Gly Val Pro Leu Thr Asp
        50                  55                  60

Glu Asp Arg Trp Pro Trp Leu Ala Ala Met Arg Ala Ala Ile Asp Ala
65                  70                  75                  80

Ala Arg Ala Glu Gly Arg Thr His Val Phe Thr Cys Ser Ala Leu Arg
                85                  90                  95

Gln Ala Tyr Arg Asp Arg Leu Thr Pro Pro Asp Gly Gly Val Thr Phe
            100                 105                 110

Val Phe Met Lys Gly Asp Ala Ser Leu Ile Gly Thr Arg Leu Ser Ala
        115                 120                 125

Arg Thr Glu His Phe Phe Asn Pro Asp Leu Leu Gln Ser Gln Phe Asp
    130                 135                 140

Thr Leu Glu Glu Pro Ser Asp Ala Leu Val Leu Asp Ile Arg Gln Ser
145                 150                 155                 160

Pro Glu Ala Leu Val Ala Thr Ile Leu Gln Ala Thr Val Pro Gln Gly
                165                 170                 175

Ala Gly Ala Ala Arg
            180

<210> SEQ ID NO 19
<211> LENGTH: 261
<212> TYPE: PRT
<213> ORGANISM: Bacillus subtilis

<400> SEQUENCE: 19

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
                20                  25                  30

Lys Val Val Ile Asn Tyr Tyr Ser Asn Lys Gln Asp Pro Asn Glu Val
```

-continued

```
            35                  40                  45
Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
                100                 105                 110

Ile Gly Thr Asn Leu Thr Gly Ala Phe Leu Gly Ser Arg Glu Ala Ile
                115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
                180                 185                 190

Thr Pro Ile Asn Ala Glu Lys Phe Ala Asp Pro Lys Gln Lys Ala Asp
                195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
                260

<210> SEQ ID NO 20
<211> LENGTH: 363
<212> TYPE: PRT
<213> ORGANISM: Pseudomonas putida

<400> SEQUENCE: 20

Met Ser Ala Leu Phe Glu Pro Tyr Thr Leu Lys Asp Val Thr Leu Arg
1               5                   10                  15

Asn Arg Ile Ala Ile Pro Pro Met Cys Gln Tyr Met Ala Glu Asp Gly
                20                  25                  30

Leu Ile Asn Asp Trp His Gln Val His Tyr Ala Ser Met Ala Arg Gly
                35                  40                  45

Gly Ala Gly Leu Leu Val Val Glu Ala Thr Ala Val Ala Pro Glu Gly
    50                  55                  60

Arg Ile Thr Pro Gly Cys Ala Gly Ile Trp Ser Asp Ala His Ala Gln
65                  70                  75                  80

Ala Phe Val Pro Val Val Gln Ala Ile Lys Ala Ala Gly Ser Val Pro
                85                  90                  95

Gly Ile Gln Ile Ala His Ala Gly Arg Lys Ala Ser Ala Asn Arg Pro
                100                 105                 110

Trp Glu Gly Asp Asp His Ile Gly Ala Asp Asp Ala Arg Gly Trp Glu
                115                 120                 125

Thr Ile Ala Pro Ser Ala Ile Ala Phe Gly Ala His Leu Pro Asn Val
    130                 135                 140
```

-continued

```
Pro Arg Ala Met Thr Leu Asp Asp Ile Ala Arg Val Lys Gln Asp Phe
145                 150                 155                 160

Val Asp Ala Ala Arg Arg Ala Arg Asp Ala Gly Phe Glu Trp Ile Glu
                165                 170                 175

Leu His Phe Ala His Gly Tyr Leu Gly Gln Ser Phe Phe Ser Glu His
                180                 185                 190

Ser Asn Lys Arg Thr Asp Ala Tyr Gly Gly Ser Phe Asp Asn Arg Ser
            195                 200                 205

Arg Phe Leu Leu Glu Thr Leu Ala Ala Val Arg Glu Val Trp Pro Glu
        210                 215                 220

Asn Leu Pro Leu Thr Ala Arg Phe Gly Val Leu Glu Tyr Asp Gly Arg
225                 230                 235                 240

Asp Glu Gln Thr Leu Glu Glu Ser Ile Glu Leu Ala Arg Arg Phe Lys
                245                 250                 255

Ala Gly Gly Leu Asp Leu Leu Ser Val Ser Val Gly Phe Thr Ile Pro
                260                 265                 270

Glu Thr Asn Ile Pro Trp Gly Pro Ala Phe Met Gly Pro Ile Ala Glu
                275                 280                 285

Arg Val Arg Arg Glu Ala Lys Leu Pro Val Thr Ser Ala Trp Gly Phe
        290                 295                 300

Gly Thr Pro Gln Leu Ala Glu Ala Ala Leu Gln Ala Asn Gln Leu Asp
305                 310                 315                 320

Leu Val Ser Val Gly Arg Ala His Leu Ala Asp Pro His Trp Ala Tyr
                325                 330                 335

Phe Ala Ala Lys Glu Leu Gly Val Glu Lys Ala Ser Trp Thr Leu Pro
                340                 345                 350

Ala Pro Tyr Ala His Trp Leu Glu Arg Tyr Arg
            355                 360
```

```
<210> SEQ ID NO 21
<211> LENGTH: 267
<212> TYPE: PRT
<213> ORGANISM: Corynebacterium aquaticum

<400> SEQUENCE: 21

Met Thr Ala Thr Ser Ser Pro Thr Thr Arg Phe Thr Asp Arg Val Val
1               5                   10                  15

Leu Ile Thr Gly Gly Gly Ser Gly Leu Gly Arg Ala Thr Ala Val Arg
                20                  25                  30

Leu Ala Ala Glu Gly Ala Lys Leu Ser Leu Val Asp Val Ser Ser Glu
            35                  40                  45

Gly Leu Glu Ala Ser Lys Ala Ala Val Leu Glu Thr Ala Pro Asp Ala
    50                  55                  60

Glu Val Leu Thr Thr Val Ala Asp Val Ser Asp Glu Ala Gln Val Glu
65                  70                  75                  80

Ala Tyr Val Thr Ala Thr Thr Glu Arg Phe Gly Arg Ile Asp Gly Phe
                85                  90                  95

Phe Asn Asn Ala Gly Ile Glu Gly Lys Gln Asn Pro Thr Glu Ser Phe
                100                 105                 110

Thr Ala Ala Glu Phe Asp Lys Val Val Ser Ile Asn Leu Arg Gly Val
            115                 120                 125

Phe Leu Gly Leu Glu Lys Val Leu Lys Ile Met Arg Glu Gln Gly Ser
        130                 135                 140

Gly Met Val Val Asn Thr Ala Ser Val Gly Gly Ile Arg Gly Ile Gly
145                 150                 155                 160
```

-continued

```
Asn Gln Ser Gly Tyr Ala Ala Ala Lys His Gly Val Val Gly Leu Thr
                165                 170                 175

Arg Asn Ser Ala Val Glu Tyr Gly Arg Tyr Gly Ile Arg Ile Asn Ala
                180                 185                 190

Ile Ala Pro Gly Ala Ile Trp Thr Pro Met Val Glu Asn Ser Met Lys
                195                 200                 205

Gln Leu Asp Pro Glu Asn Pro Arg Lys Ala Ala Glu Glu Phe Ile Gln
        210                 215                 220

Val Asn Pro Ser Lys Arg Tyr Gly Glu Ala Pro Glu Ile Ala Ala Val
225                 230                 235                 240

Val Ala Phe Leu Leu Ser Asp Asp Ala Ser Tyr Val Asn Ala Thr Val
                245                 250                 255

Val Pro Ile Asp Gly Gly Gln Ser Ala Ala Tyr
                260                 265
```

```
<210> SEQ ID NO 22
<211> LENGTH: 249
<212> TYPE: PRT
<213> ORGANISM: Ralstonia solanacearum

<400> SEQUENCE: 22

Met Tyr Arg Leu Leu Asn Lys Thr Ala Val Ile Thr Gly Gly Asn Ser
1               5                   10                  15

Gly Ile Gly Leu Ala Thr Ala Lys Arg Phe Val Ala Glu Gly Ala Tyr
                20                  25                  30

Val Phe Ile Val Gly Arg Arg Arg Lys Glu Leu Glu Gln Ala Ala Ala
            35                  40                  45

Glu Ile Gly Arg Asn Val Thr Ala Val Lys Ala Asp Val Thr Lys Leu
    50                  55                  60

Glu Asp Leu Asp Arg Leu Tyr Ala Ile Val Arg Glu Gln Arg Gly Ser
65                  70                  75                  80

Ile Asp Val Leu Phe Ala Asn Ser Gly Ala Ile Glu Gln Lys Thr Leu
                85                  90                  95

Glu Glu Ile Thr Pro Glu His Tyr Asp Arg Thr Phe Asp Val Asn Val
                100                 105                 110

Arg Gly Leu Ile Phe Thr Val Gln Lys Ala Leu Pro Leu Leu Arg Asp
            115                 120                 125

Gly Gly Ser Val Ile Leu Thr Ser Ser Val Ala Gly Val Leu Gly Leu
        130                 135                 140

Gln Ala His Asp Thr Tyr Ser Ala Ala Lys Ala Ala Val Arg Ser Leu
145                 150                 155                 160

Ala Arg Thr Trp Thr Thr Glu Leu Lys Gly Arg Ser Ile Arg Val Asn
                165                 170                 175

Ala Val Ser Pro Gly Ala Ile Asp Thr Pro Ile Ile Glu Asn Gln Val
                180                 185                 190

Ser Thr Gln Glu Glu Ala Asp Glu Leu Arg Ala Lys Phe Ala Ala Ala
            195                 200                 205

Thr Pro Leu Gly Arg Val Gly Arg Pro Glu Glu Leu Ala Ala Ala Val
        210                 215                 220

Leu Phe Leu Ala Ser Asp Asp Ser Ser Tyr Val Ala Gly Ile Glu Leu
225                 230                 235                 240

Phe Val Asp Gly Gly Leu Thr Gln Val
                245
```

```
<210> SEQ ID NO 23
<211> LENGTH: 1048
<212> TYPE: PRT
<213> ORGANISM: Bacillus megaterium

<400> SEQUENCE: 23

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
            35                  40                  45

Thr Arg Tyr Leu Ser Ser Gln Arg Leu Ile Lys Glu Ala Cys Asp Glu
        50                  55                  60

Ser Arg Phe Asp Lys Asn Leu Ser Gln Gly Leu Lys Phe Val Arg Asp
65                  70                  75                  80

Phe Ala Gly Asp Gly Leu Phe Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
            115                 120                 125

Lys Trp Glu Arg Leu Asn Ala Asp Glu His Ile Glu Val Pro Glu Asp
        130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
            195                 200                 205

Ile Lys Val Met Asn Asp Leu Val Asp Lys Ile Ile Ala Asp Arg Lys
        210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
                260                 265                 270

Leu Ser Phe Ala Leu Tyr Phe Leu Val Lys Asn Pro His Val Leu Gln
            275                 280                 285

Lys Ala Ala Glu Glu Ala Ala Arg Val Leu Val Asp Pro Val Pro Ser
        290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Leu Met Val Leu Ile Pro Gln Leu His Arg Asp Lys Thr Ile Trp Gly
            355                 360                 365

Asp Asp Val Glu Glu Phe Arg Pro Glu Arg Phe Glu Asn Pro Ser Ala
        370                 375                 380
```

-continued

```
Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
                420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr Glu
        450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
        530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
        610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
                660                 665                 670

Gln Gln Pro Gly Ser Ala Arg Ser Thr Arg His Leu Glu Ile Glu Leu
            675                 680                 685

Pro Lys Glu Ala Ser Tyr Gln Glu Gly Asp His Leu Gly Val Ile Pro
            690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Glu Lys Leu Ala
                725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
        755                 760                 765

Ala Lys Thr Val Ser Pro Pro His Lys Val Glu Leu Glu Ala Leu Leu
        770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Ser Glu Met Lys Phe Ser Glu
```

-continued

```
                    805              810              815

Phe Ile Ala Leu Leu Pro Ser Ile Arg Pro Arg Tyr Tyr Ser Ile Ser
             820              825              830

Ser Ser Pro Arg Val Asp Glu Lys Gln Ala Ser Ile Thr Val Ser Val
             835              840              845

Val Ser Gly Glu Ala Trp Ser Gly Tyr Gly Glu Tyr Lys Gly Ile Ala
         850              855              860

Ser Asn Tyr Leu Ala Glu Leu Gln Glu Gly Asp Thr Ile Thr Cys Phe
865              870              875              880

Ile Ser Thr Pro Gln Ser Glu Phe Thr Leu Pro Lys Asp Pro Glu Thr
             885              890              895

Pro Leu Ile Met Val Gly Pro Gly Thr Gly Val Ala Pro Phe Arg Gly
             900              905              910

Phe Val Gln Ala Arg Lys Gln Leu Lys Glu Gln Gly Gln Ser Leu Gly
             915              920              925

Glu Ala His Leu Tyr Phe Gly Cys Arg Ser Pro His Glu Asp Tyr Leu
         930              935              940

Tyr Gln Glu Glu Leu Glu Asn Ala Gln Ser Glu Gly Ile Ile Thr Leu
945              950              955              960

His Thr Ala Phe Ser Arg Met Pro Asn Gln Pro Lys Thr Tyr Val Gln
             965              970              975

His Val Met Glu Gln Asp Gly Lys Lys Leu Ile Glu Leu Leu Asp Gln
             980              985              990

Gly Ala His Phe Tyr Ile Cys Gly  Asp Gly Ser Gln Met  Ala Pro Ala
         995              1000             1005

Val Glu  Ala Thr Leu Met Lys  Ser Tyr Ala Asp Val  His Gln Val
    1010             1015             1020

Ser Glu  Ala Asp Ala Arg Leu  Trp Leu Gln Gln Leu  Glu Glu Lys
    1025             1030             1035

Gly Arg  Tyr Ala Lys Asp Val  Trp Ala Gly
    1040             1045
```

```
<210> SEQ ID NO 24
<211> LENGTH: 471
<212> TYPE: PRT
<213> ORGANISM: Francisella tularensis

<400> SEQUENCE: 24

Met Ser Phe Asp Asn Leu Leu Leu Met Thr Asp Ser Tyr Lys His Ser
1               5               10              15

His Arg Tyr Gln Tyr Pro Arg Asp Thr His Tyr Leu His Phe Tyr Leu
             20              25              30

Glu Ser Arg Gly Thr Ala Asn Lys Asp Leu Gly Asn Tyr Thr Lys Phe
         35              40              45

Phe Gly Leu Gln Tyr Tyr Val Lys Lys Tyr Leu Ser Gln Pro Ile Thr
     50              55              60

Gln Gln Met Ile Asp Asp Ala Glu Lys Ile Leu Leu Ala His Gly Leu
65              70              75              80

Pro Phe Tyr Arg Ser Gly Phe Glu Lys Ile Leu Asn Asn Tyr Asn Gly
             85              90              95

Tyr Leu Pro Ile Arg Ile Arg Ala Val Arg Glu Gly Ser Leu Ile Pro
             100             105             110

Leu His Asn Val Leu Met Thr Ile Glu Ser Thr Asp Glu Glu Leu Phe
             115             120             125
```

```
Trp Leu Pro Gly Phe Val Glu Thr Leu Leu Leu Lys Val Trp Tyr Pro
    130             135             140

Thr Thr Val Ala Thr Ile Ser Phe Asn Ile Lys Gln Leu Ile Lys Arg
145             150             155             160

Tyr Leu Leu Glu Thr Ala Asp Ser Leu Asp Lys Leu Asp Phe Met Leu
            165             170             175

His Asp Phe Gly Tyr Arg Gly Val Ser Ser Glu Glu Ser Ala Gly Ile
            180             185             190

Gly Gly Ala Ala His Leu Thr Asn Phe Leu Gly Thr Asp Thr Leu Ala
            195             200             205

Ala Leu His Val Cys Lys Glu Phe Tyr Ala Glu Asp Met Ala Gly Phe
    210             215             220

Ser Ile Pro Ala Ser Glu His Ser Thr Met Thr Ser Trp Gly Val Gly
225             230             235             240

Thr Glu Cys Glu Arg Glu Ala Phe Glu Asn Met Ile Ala Gln Phe Gly
            245             250             255

Asp Ser Ser Val Leu Tyr Ala Cys Val Ser Asp Ser Trp Asp Phe Lys
            260             265             270

Lys Ala Ile Gln Thr Trp Val Asp Leu Lys Asp Arg Val Thr Ala Lys
            275             280             285

Lys Ala Asn Leu Val Ile Arg Pro Asp Ser Gly Asp Ala Val Asp Asn
    290             295             300

Ile Leu Tyr Ala Leu Tyr Glu Leu Asp Lys Gly Tyr Gly Ser Arg Leu
305             310             315             320

Asn Ser Lys Gly Tyr Lys Val Leu Asn Asn Val Ala Leu Ile Gln Gly
            325             330             335

Asp Ser Val Ser Ile Ser Leu Ala Lys Lys Val Leu Glu Ala Met Lys
            340             345             350

Ile Gln Gly Tyr Ser Ala Glu Asn Ile Ala Phe Gly Met Gly Gly Ala
            355             360             365

Leu Leu Gln Gly Asn Tyr Glu Ser Ser Ile Asn Arg Asp Ser Phe Lys
    370             375             380

Phe Ala Ile Lys Cys Ser Ala Ile Met Arg Gly Asn Thr Leu Ile Gly
385             390             395             400

Val Lys Lys Glu Pro Ile Thr Asp Leu Ala Lys Lys Ser Lys Gln Gly
            405             410             415

Arg Leu Asp Leu Ile Lys Asp Ala Lys Gly Asn Tyr Lys Thr Ile Val
            420             425             430

Leu Asp Asp Ser Tyr Ala Leu Gly Glu Tyr His Pro Glu Ser Gln Leu
            435             440             445

Gln Thr Tyr Tyr Asp Asn Gly Glu Ile Lys Phe Glu Gln Ser Leu Ala
    450             455             460

Gln Ile Arg Asn Tyr Thr Asn
465             470
```

<210> SEQ ID NO 25
<211> LENGTH: 783
<212> TYPE: DNA
<213> ORGANISM: Bacillus subtilis

<400> SEQUENCE: 25

```
atgtatccgg atctgaaagg taaggtggtg gcaatcaccg gtgcagcaag cggcctgggc        60
aaagctatgg ctatccgctt tggtaaagag caggcaaaag tggtgatcaa ttactattct       120
aataaacagg acccgaacga agtgaaagaa gaagtgatta aagccggcgg cgaagcagtg       180
```

-continued

```
gttgttcagg gtgacgtgac caaagaagaa gacgtgaaga acattgtgca gaccgccatc    240
aaggagtttg gcacactgga tatcatgatc aacaacgccg gtctggagaa tccggtgccg    300
agccatgaaa tgccgctgaa ggactgggac aaagtgatcg gcaccaatct gacaggcgca    360
tttctgggca gccgcgaggc aatcaaatat tttgttgaaa atgatatcaa aggtaatgtt    420
attaatatga gcagcgtgca cgaagtgatt ccgtggccgc tgtttgtgca ttatgcagcc    480
agcaaaggcg gcattaaact gatgaccgag accctggccc tggaatatgc cccgaaaggc    540
attcgcgtga acaatattgg tccgggtgcc atcaataccc cgatcaacgc cgaaaagttt    600
gccgacccga aacagaaagc cgatgtggag agcatgattc cgatgggcta catcggcgaa    660
ccggaagaaa ttgcagcagt ggccgcctgg ctggccagta aggaagcaag ctatgtgacc    720
ggcattaccc tgtttgccga tggcggcatg acacagtatc cgagctttca ggcaggccgc    780
ggt                                                                  783
```